US010183921B2

(12) United States Patent
Reddell et al.

(10) Patent No.: US 10,183,921 B2
(45) Date of Patent: Jan. 22, 2019

(54) METHODS AND COMPOSITIONS FOR WOUND HEALING

(71) Applicant: QBiotics Limited, Yungaburra (AU)

(72) Inventors: Paul Warren Reddell, Yungaburra (AU); Victoria Anne Gordon, Yungaburra (AU); Ryan Moseley, Bridgend (GB); Robert Steadman, Caerphilly (GB); Rachael Louise Moses, Milton Keynes (GB); Glen Mathew Boyle, Taringa (AU); Peter Gordon Parsons, St. Lucia (AU)

(73) Assignee: QBiotics Limited, Yungaburra (AU)

( * ) Notice: Subject to any disclaimer, the term of this patent is extended or adjusted under 35 U.S.C. 154(b) by 0 days.

(21) Appl. No.: 14/785,127

(22) PCT Filed: Apr. 17, 2014

(86) PCT No.: PCT/AU2014/050018
§ 371 (c)(1),
(2) Date: Oct. 16, 2015

(87) PCT Pub. No.: WO2014/169356
PCT Pub. Date: Oct. 23, 2014

(65) Prior Publication Data
US 2016/0068499 A1 Mar. 10, 2016

(30) Foreign Application Priority Data
Apr. 18, 2013 (AU) ................................ 2013901359

(51) Int. Cl.
| | | |
|---|---|---|
| A61K 31/12 | (2006.01) |
| A61K 31/336 | (2006.01) |
| C07D 303/40 | (2006.01) |
| C07D 303/32 | (2006.01) |
| A61K 31/122 | (2006.01) |
| A61K 36/47 | (2006.01) |
| A61K 8/49 | (2006.01) |
| A61Q 19/00 | (2006.01) |
| A61K 9/00 | (2006.01) |
| A61K 9/06 | (2006.01) |
| A61K 47/10 | (2017.01) |

(52) U.S. Cl.
CPC .......... *C07D 303/40* (2013.01); *A61K 8/4973* (2013.01); *A61K 9/0014* (2013.01); *A61K 9/0019* (2013.01); *A61K 9/06* (2013.01); *A61K 31/122* (2013.01); *A61K 31/336* (2013.01); *A61K 36/47* (2013.01); *A61K 47/10* (2013.01); *A61Q 19/00* (2013.01); *C07D 303/32* (2013.01); *A61K 2236/15* (2013.01); *A61K 2236/33* (2013.01); *A61K 2800/74* (2013.01)

(58) Field of Classification Search
CPC .. C07D 303/40; C07D 303/32; A61K 8/4973; A61K 9/0014; A61K 31/122; A61K 31/336
See application file for complete search history.

(56) References Cited

FOREIGN PATENT DOCUMENTS

| | | |
|---|---|---|
| AU | 2010200429 A1 | 8/2010 |
| JP | 2005-230051 A | 9/2005 |
| WO | 02/09639 A2 | 2/2002 |
| WO | 2006/026604 A2 | 3/2006 |
| WO | 2007/070985 A1 | 6/2007 |

OTHER PUBLICATIONS

Cable, "Proud Flesh", The Horse, May 1, 2000. http://www.thehorse.com/articles/10172/proud-flesh.*
Extended European Search Report, dated Feb. 29, 2016, for corresponding European Application No. 14784998.8-1466 / 2986615, 8 pages.
International Search Report, dated May 27, 2014, for corresponding International Application No. PCT/AU2014/050018, 3 pages.
Mali et al., "*Baliospermum montanum* (Danti): Ethnobotany, phytochemistry and pharmacology—A review," *International Journal of Green Pharmacy*, Oct.-Dec. 2008, pp. 194-199.
Written Opinion of the International Searching Authority, dated May 27, 2014, for corresponding International Application No. PCT/AU2014/050018, 4 pages.
Theoret et al., "Equine Exuberant Granulation Tissue and Human Keloids: A Comparative Histopathologic Study," *Veterinary Surgery*, 42: 783-789 (2013).
Wilmink et al., "Second-Intention Repair in the Horse and Pony and Management of Exuberant Granulation Tissue," *Vet Clin Equine*, 21: 15-32 (2005).

* cited by examiner

*Primary Examiner* — Sahar Javanmard
(74) *Attorney, Agent, or Firm* — Seed IP Law Group LLP

(57) ABSTRACT

The present invention relates to epoxy-tigliane compounds and their use in promoting wound healing. In particular embodiments, the epoxy-tigliane compounds are epoxy-tigliaen-3-one compounds. Methods of inducing or promoting wound healing as well as methods of reducing scarring and improving cosmetic outcomes upon healing of a wound are described. Compounds and compositions for use in wound healing are also described.

14 Claims, 3 Drawing Sheets

METHODS AND COMPOSITIONS FOR WOUND HEALING

FIELD OF THE INVENTION

The present invention relates to epoxy-tigliane compounds and their use in promoting wound healing. In particular embodiments, the epoxy-tigliane compounds are epoxy-tigliaen-3-one compounds. Methods of inducing or promoting wound healing as well as methods of reducing scarring and improving cosmetic outcomes upon healing of a wound are described. Compounds and compositions for use in wound healing are also described.

BACKGROUND OF THE INVENTION

Wound healing is an intricate process in which the skin or another organ or tissue, repairs itself after injury. In normal skin, the epidermis (outermost layer) and dermis (inner or deeper layer) exists in a steady-state equilibrium, forming a protective barrier against the external environment. Once the protective barrier is broken, the normal physiologic process of wound healing is immediately set in motion. The classic model of wound healing is divided into three sequential, yet overlapping phases, namely: inflammatory, proliferative and finally remodelling.

During the inflammatory phase of wound healing there is active recruitment of neutrophils and then monocytes from surrounding vasculature into the wound. Neutrophils are essential to the initial control and destruction of bacterial and fungal infections in the wound. Monocytes mature into macrophages as they enter the wound where they have numerous roles during the course of wound resolution including the initial phagocytosis and clean-up of matrix and cell debris. The release of enzymes, cytokines and growth factors by both neutrophils and macrophages in the wound can then exert a profound influence on other cells within the wound and surrounding tissue. For example, macrophages secrete collagenases which debride the wound; interleukins and tumor necrosis factor (TNF), which stimulate fibroblasts and promote angiogenesis; and transforming growth factor (TGF), which stimulates keratinocytes. They also secrete platelet-derived growth factor and vascular endothelial growth factor which initiate the formation of granulation tissue and thus initiate the transition into the proliferative and remodelling phases. A rapid and robust, but transient, inflammatory phase is often associated with good wound healing outcomes.

The second stage of wound healing involves cell proliferation and migration and wound contraction. This involves actions taken by cells within the wound to achieve closure of the wound gap and replenish lost tissue. Migration and proliferation of keratinocytes is fundamental to achieve re-epithelialisation of the wound, while reconstitution of the underlying dermis results from migration, proliferation and differentiation of fibroblasts which help draw the wound closed and contribute to the synthesis, bundling and alignment of collagen fibres.

In the final remodelling stage, migrating and proliferating keratinocytes at the wound edge re-stratify to seal the wound and form a continuous epidermis. During this stage many changes also occur in the dermis involving remodelling of the extracellular matrix to restore a normal dermal architecture and vasculature.

In certain cases, wounds may be slow to heal or not heal at all. Many factors affect the healing of a wound, for example, the general health of the wounded subject, the age of the wounded subject, diseases such as diabetes, or other diseases that may affect circulation, the presence of infection, foreign objects or necrotic tissue, or in some instances, medication may affect the rate of wound healing.

Furthermore, in some wounds imperfect regulation of wound resolution can result in fibrosis and excessive scar formation to leaving scar tissue that is functionally and cosmetically inferior to normal tissue.

There is much research into improving wound healing and reducing scar tissue. However, there is a need to find agents that are capable of promoting wound healing, for example, increasing the rate of wound healing, particularly in chronic wounds. There is also a need for agents that allow a wound to heal with reduced scarring than would occur naturally.

SUMMARY OF THE INVENTION

The present invention is predicated, at least in part, on the discovery that extracts from plants that contain epoxy-tigliane compounds are able to promote wound healing and also reduce scar tissue formed upon healing of the wound.

In a first aspect of the invention there is provided a method of promoting wound healing in a subject comprising administering to the subject an epoxy-tigliane compound or a pharmaceutically acceptable salt thereof.

In some embodiments, the epoxy-tigliane compound is in the form of a plant extract, especially an ethanolic extract. In some embodiments, the plant extract is obtainable from or obtained from a plant which is a *Fontainea* species or a *Hylandia* species. In some embodiments, the epoxy-tigliane compound is isolated from the plant extract. In other embodiments, the epoxy-tigliane compound is a synthetic or semi-synthetic derivative of an isolated tigliane compound.

In some embodiments, the promoting wound healing comprises increasing the rate of wound healing. In some embodiments, the promoting wound healing comprises reducing scarring in the wound tissue. In some embodiments, the promoting wound healing comprises both increasing the rate of wound healing and reducing scarring in wound tissue. In some embodiments, the wound is a chronic wound, acute wound or existing wound.

In yet another aspect of the invention, there is provided a method of treating or preventing excessive scarring comprising applying to the wound or scar an epoxy-tigliane compound or a pharmaceutically acceptable salt thereof.

In some embodiments, the excessive scarring is keloid or hypertrophic scarring.

In another aspect of the invention there is provided a use of an epoxy-tigliane compound or a pharmaceutically acceptable salt thereof in the manufacture of a medicament for promoting wound healing in a subject.

In yet another aspect of the invention, there is provided a use of an epoxy-tigliane compound or a pharmaceutically acceptable salt thereof for promoting wound healing in a subject.

DESCRIPTION OF THE INVENTION

Definitions

Unless defined otherwise, all technical, and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The term "alkyl" refers to optionally substituted linear and branched hydrocarbon groups having 1 to 20 carbon atoms. Where appropriate, the alkyl group may have a specified number of carbon atoms, for example, —$C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, 2-methylpentyl, 3-methylpentyl, 4-methylpentyl, 2-ethylbutyl, 3-ethylbutyl, heptyl, octyl, nonyl, decyl, undecyl, dodecyl, tridecyl, tetradecyl and pentadecyl.

The term "alkenyl" refers to optionally substituted, unsaturated linear or branched hydrocarbons, having 2 to 20 carbon atoms and having at least one double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-1,3-diene, hex-1,3-diene, non-1,3,5-triene and the like.

The term "alkynyl" refers to optionally substituted unsaturated linear or branched hydrocarbons, having 2 to 20 carbon atoms, having at least one triple bond. Where appropriate, the alkynyl group may have a specified number of carbon atoms, for example, $C_2$-$C_6$ alkynyl which includes alkynyl groups having 2, 3, 4, 5 or 6 carbon atoms in linear or branched arrangements. Non-limiting examples include ethynyl, propynyl, butynyl, pentynyl and hexynyl.

The terms "cycloalkyl" and "carbocyclic" refer to optionally substituted saturated or unsaturated mono-cyclic, bicyclic or tricyclic hydrocarbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

"Aryl" means a $C_6$-$C_{14}$ membered monocyclic, bicyclic or tricyclic carbocyclic ring system having up to 7 atoms in each ring, wherein at least one ring is aromatic. Examples of aryl groups include, but are not limited to, phenyl, naphthyl, tetrahydronaphthyl, indanyl and biphenyl. The aryl may comprise 1-3 benzene rings. If two or more aromatic rings are present, then the rings may be fused together, so that adjacent rings share a common bond.

Each alkyl, alkenyl, alkynyl, cycloalkyl and aryl, whether an individual entity or as part of a larger entity may be optionally substituted with one or more optional substituents selected from the group consisting of $C_{1-6}$alkyl, $C_{2-6}$alkenyl, $C_{3-6}$cycloalkyl, oxo (=O), —OH, —SH, $C_{1-6}$alkylO—, $C_{2-6}$alkenylO—, $C_{3-6}$cycloalkylO—, $C_{1-6}$alkylS—, $C_{2-6}$alkenylS—, $C_{3-6}$cycloalkylS—, —$CO_2$H, —$CO_2C_{1-6}$alkyl, —$NH_2$, —NH($C_{1-6}$alkyl), —N($C_{1-6}$alkyl)$_2$, —NH(phenyl), —N(phenyl)$_2$, —CN, —$NO_2$, -halogen, —$CF_3$, —$OCF_3$, —$SCF_3$, —$CHF_2$, —$OCHF_2$, —$SCHF_2$, -phenyl, -Ophenyl, —C(O)phenyl, —C(O)$C_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —$CO_2$H, —$CO_2CH_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be obtained by isolation from natural sources, by asymmetric synthesis, for example using chiral intermediates, or by chiral resolution. The compounds of the invention may exist as geometrical isomers. The invention also relates to compounds in substantially pure cis (Z) or trans (E) forms or mixtures thereof.

The compounds of the present invention may be obtained by isolation from a plant or plant part, or by derivatisation of the isolated compound, or by derivatisation of a related compound.

As used herein, the term "wound" refers to physical disruption of the continuity or integrity of tissue structure. Wounds include may be acute or chronic and include cuts and lacerations, surgical incisions or wounds, punctures, grazes, scratches, compression wounds, abrasions, friction wounds, decubitus ulcers (e.g. pressure or bed sores); thermal effect wounds (burns from cold and heat sources), chemical wounds (e.g. acid or alkali burns) or pathogenic infections (e.g. viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, eg psoriasis and eczema, stomach or intestinal ulcers, oral wounds, including a ulcers of the mouth, damaged cartilage or bone, amputation wounds and corneal lesions.

As used herein, the term "chronic wound" refers to a wound that has not healed within a normal time period for healing in an otherwise healthy subject. Chronic wounds may be those that do not heal because of the health of the subject, for example, where the subject has poor circulation or a disease such as diabetes, or where the subject is on a medication that inhibits the normal healing process. Healing may also be impaired by the presence of infection, such as a bacterial, fungal or parasitic infection. In some instances a chronic wound may remain unhealed for weeks, months or even years. Examples of chronic wounds include but are not limited to, diabetic ulcers, pressure sores and tropical ulcers.

The term "promoting wound healing" as used herein, refers to improving wound healing compared to the wound healing that would be observed in an untreated wound. Promoting wound healing includes increasing the rate of wound healing, for example, the wound may heal at a rate that is hours, days or weeks faster than if the wound was left untreated. Promoting wound healing may also encompass the reduction of scar tissue in the healing or healed wound compared to that expected when a wound is left untreated.

The term "wound healing" refers to the restoration of the tissue integrity, either in part or in full.

The term "reducing scarring" or "reducing scar tissue" as referred to herein relates to an improved cosmetic result and/or reduced abnormal tissue caused by the healing of the wound compared to if the wound was left untreated. In some embodiments, reducing scar tissue includes reducing or minimising abnormal tissue, reducing or minimising changes in skin pigmentation and/or improving hair regrowth compared to when the wound is left untreated.

The term "epoxy-tigliane compound" refers to a compound having one of the following basic carbon cyclic structures:

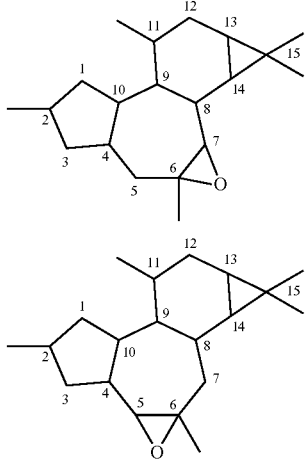

The compounds have a tricyclo[9.3.0.0]tetradecane system with a fused cyclopropane ring appended to the six membered ring. The epoxide is fused to the seven membered ring in the 5,6- or 6,7-position.

The term "epoxy-tiglien-3-one compound" refers to a compound having an epoxy-tigliane structure defined above where the five membered ring has a 1,2-ene-3-one structure:

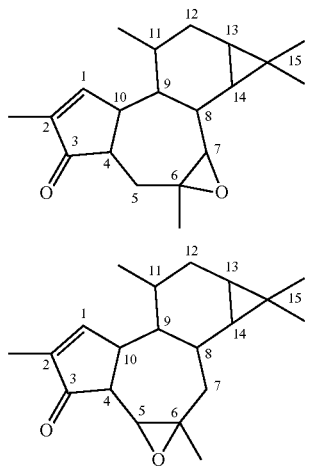

Methods of Wound Healing

In a first aspect of the invention there is provided a method of promoting wound healing in a subject comprising administering to the subject, an epoxy-tigliane compound or a pharmaceutically acceptable salt thereof.

The wound to be healed may be present in any organ or tissue, including internal organs or tissues or external tissues, such as skin. The wound may be the result of an injury, bite or burn. The organ or tissue may be any one or more of skin, muscle, liver, kidneys, lungs, heart, pancreas, spleen, stomach, intestines bladder, ovaries, testicles, uterus, cartilage, tendon, ligament, bone and the like. In particular embodiments, the wound is in the skin and/or muscle.

In some embodiments, the epoxy-tigliane compound is administered soon after the wound is incurred. In other embodiments, the wound is a chronic wound that has failed to heal over days, weeks, months or years. In yet other embodiments, the wound is an existing wound which has failed to heal at a normal rate or has failed to respond to other therapies.

The compounds of the invention may also be applied to a wound which is healing or has healed with excessive scarring. Examples of such wounds are those that are producing or have produced keloid scars or hypertrophic scars.

In some embodiments, the wound is infected with a bacterial infection. The bacterial infection may be caused by a Gram positive or Gram negative bacteria, especially a Gram positive bacteria. Non-limiting examples of bacteria that are controlled by the compounds of the invention include bacteria of the Genus *Bacillus*, such as *B. subtilis, B. anthracis, B. cereus, B. firmis, B. licheniformis, B. megaterium, B. pumilus, B. coagulans, B. pantothenticus, B. alvei, B. brevis, B. circubins, B. laterosporus, B. macerans, B. polymyxa, B. stearothermophilus, B. thuringiensis* and *B. sphaericus*; Staphlococcus such as *S. aureus, S. epidermidis, S. haemolyticus, S. saprophyticus*; Streptococcus, for example, *S. pyrogenes, S. pneumoniae, S. alagactiae, S. dysgalactiae, S. equisimilis, S. equi, S. zooepidemicus, S.*

*anginosus, S. salwarius, S. milleri, S. sanguis, S. mitior, S. mutans, S. faecalis, S. faecium, S. bovis, S. equinus, S. uberus* and *S. avium; Aerococcus* spp., *Gemella* spp., *Corynebacterium* spp., *Listeria* spp., *Kurthia* spp., *Lactobacillus* spp., *Erysipelothrix* spp., *Arachnia* spp., *Actinomyces* spp., *Propionibacterium* spp., *Rothia* spp., *Bifidobacterium* spp., *Clostridium* spp., *Eubacterium* spp., *Serratia* spp., *Klebsiella* spp., *Proteus* spp., *Enterococcus* spp., *Pseudomonas* spp., *Nocardia* spp. and *Mycobacterium* spp.

In some embodiments, the wound is infected with a fungal infection. The fungal infection may be caused by filamentous fungi or yeasts. Non-limiting examples of fungi that are controlled by the compounds of the invention include fungi of the Genus such as *Aspergillus* spp., *Mucor* spp., *Trichtophyton* spp., *Cladosporium* spp., *Ulocladium* spp., *Curvularia* spp., *Aureobasidium* spp., *Candida albicans, Candida* spp., *Cryptococcus* spp., *Malessezia pachydermatis, Malessezia* spp. and *Trichosporon* spp.

In some embodiments the wound is infected by both bacterial and fungal infections, including in biofilms.

The subject having a wound to be healed may be any subject including mammals, birds, fish and reptiles. In some embodiments, the subject is a human, a companion animal, a laboratory animal, a farming or working animal, a farmed bird, a racing animal or a captive wild animal such as those kept in zoos. Examples of suitable subjects include but are not limited to humans, dogs, cats, rabbits, hamsters, guinea pigs, mice, rats, horses, cattle, sheep, goats, deer, pigs, monkeys, marsupials, chickens, geese, canaries, budgies, crocodiles, snakes, lizards and the like. In particular embodiments, the subject is a mammalian subject such as a human, dog, cat, horse, cattle, sheep, goat, pig, deer, rat, guinea pig, kangaroo, rabbit or mouse.

In some embodiments, the administration of epoxy-tigliane compound promotes the healing of a wound by increasing the rate of healing of the wound. In some embodiments, the administration of the epoxy-tigliane compound promotes healing by reducing scarring or the amount of scar tissue that would form in the absence of treatment. In some embodiments, the treatment improves the cosmetic result or outcome or appearance of the wound once it has healed including improving skin pigmentation and improving hair regrowth compared to a wound that has not been treated.

In particular embodiments of the promotion of wound healing, the therapy is preferably topical at or around the site or administered intra-lesionally to provide a localised effect.

An "effective amount" means an amount necessary at least partly to attain the desired response, for example, to initiate healing of a wound or to increase the rate of healing of a wound. The amount varies depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 0.5 mg to 1 g per kg of body weight per dosage. In one embodiment, the dosage is in the range of 1 mg to 500 mg per dosage. In another embodiment, the dosage is in the range of 1 mg to 250 mg per dosage. In yet another embodiment, the dosage is in the range of 1 mg to 100 mg per dosage, such as up to 50 mg per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

In some embodiments, the epoxy-tigliane compound or a plant extract containing at least one epoxy-tigliane compound may be administered separately, either simultaneously or sequentially, or in the same composition as another pharmaceutically active agent that is useful in wound healing. For example, the epoxy-tigliane compounds may be administered in combination with an antibiotic and/or an anti-inflammatory agent. Suitable antibiotics include beta-lactam antibiotics such as penicillin, ampicillin, amoxycillin, flucloxacillin, dicloxacillin, methacillin, carbenicillin and norocillin; cephalosporins such as cephalexin, cefacetrile, cefadroxil, cefaloglycin, cefalonium, cefalordidine, cefatrizine, ceaclor, cefproxil, cefuzonam, cefmetozole, loracarbef, cefminox, cefdinir, cefpodoxime, and cefpirome; carbapenems such as imipenem, meropenem, ertapenem, daripenem, panipenem and biapenem; aminoglycosids such as gentamicin, streptomycin, neomycin, kanamycin, vancomycin, erythromycin and asithromycin; oxazolidinones such as linezolid and posizolid, lincosamides such as clindamycin, quinolines such as oxolinic acid, ciprofloxacin, enoxacin, ofloxacin, lomefloxacin, levofloxacin and difloxacin; and sulfonamides such as sulfamethoxazole, sulfoadiazine and sulfacetamide, or mixtures such as amoxyclav (amoxycillin and clavulinic acid). Suitable anti-inflammatory agents include non-steroidal anti-inflammatory drugs such as meloxicam, piroxicam, oxicam, aspirin, difunisal, ibuprofen, dexibuprofen, naproxen, ketoprofen, indomethacin, tolmetin, mefenamic acid, numisulide and the like and corticosteroids such as hydrocortisone, prednisolone, methylprednisolone, prednisone, budesonide, betamethasone and dexamethasone.

The epoxy-tigliane compounds can be used in combination with other wound healing therapies such as dressings and ointments, lotions and gels. For example, the epoxy-tigliane compounds may be used in combination with silver dressings and dressings, ointments, lotions and gels comprising therapeutic agents such as iodine, aloe vera, paw paw, or medically active honeys such as manuka honey or other biologically or physiologically active agents such as antiviral agents, antibacterial agents, antifungal agents, and vitamins, such as A, C, D and E and their esters. The epoxy-tigliane compounds may also be used in combination with dressings that provide molecular structure for the wound. Such dressings may include polymeric films and cross-linked polymeric films, such as hyaluronic acid and related structures, including cross-linked hyaluronic acid.

In some embodiments, the epoxy-tigliane compound is a compound of formula (I):

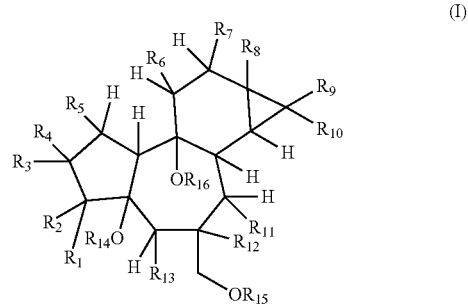

(I)

wherein $R_1$ is hydrogen and $R_2$ is —$OR_{17}$; or $R_1$ and $R_2$ together form a carbonyl group (=O);

$R_3$ is hydrogen or $C_{1-6}$alkyl;

$R_4$ and $R_5$ are independently hydrogen or —$OR_{17}$; or $R_4$ and $R_5$ together form a double bond or an epoxide (—O—);

$R_6$ is hydrogen or $C_{1-6}$alkyl;

$R_7$ is —OH or —$OR_{18}$;

$R_8$ is —OH or —$OR_{18}$; provided that $R_7$ and $R_8$ are not both —OH;

$R_9$ and $R_{10}$ are independently selected from hydrogen and $C_{1-6}$alkyl;

$R_{11}$ and $R_{12}$ or $R_{12}$ and $R_{13}$ together form an epoxide and the remaining group of $R_{11}$ and $R_{13}$ is hydrogen, —OH or —$OR_{17}$;

$R_{14}$ is hydrogen or —$R_{17}$;

$R_{15}$ is hydrogen or —$R_{17}$;

$R_{16}$ is hydrogen or —$R_{17}$;

$R_{17}$ is hydrogen, —$C_{1-6}$alkyl, —$C_{2-6}$alkenyl, —$C_{2-6}$alkynyl, —C(O)$C_{1-6}$alkyl, —C(O)$C_{2-6}$alkenyl or —C(O)$C_{2-6}$alkynyl;

$R_{18}$ is $C_{1-20}$alkyl, —$C_{2-20}$alkenyl, —$C_{2-20}$alkynyl, —C(O)$C_{1-20}$alkyl, —C(O)$C_{2-20}$alkenyl, —C(O)$C_{2-20}$alkynyl, —C(O)cycloalkyl, —C(O)$C_{1-10}$alkylcycloalkyl, —C(O)$C_{2-10}$alkenylcycloalkyl, —C(O)$C_{2-10}$alkynylcycloalkyl, —C(O)aryl, —C(O)$C_{1-10}$alkylaryl, —C(O)$C_{2-10}$alkenylaryl, —C(O)$C_{2-10}$alkynylaryl, —C(O)$C_{1-10}$alkylC(O)$R_{19}$, —C(O)$C_{2-10}$alkenylC(O)$R_{19}$, —C(O)$C_{2-10}$alkynylC(O)$R_{19}$, —C(O)$C_{1-10}$alkylCH(O$R_{19}$)(O$R_{19}$), —C(O)$C_{2-10}$alkenylCH(O$R_{19}$)(O$R_{19}$), —C(O)$C_{2-10}$alkynylCH(O$R_{19}$)(O$R_{19}$), —C(O)$C_{1-10}$alkylS$R_{19}$, —C(O)$C_{2-10}$alkenylS$R_{19}$, —C(O)$C_{2-10}$alkynylS$R_{19}$, —C(O)$C_{1-10}$alkylC(O)O$R_{19}$, —C(O)$C_{2-10}$alkenylC(O)O$R_{19}$, —C(O)$C_{2-10}$-alkynylC(O)O$R_{19}$, —C(O)$C_{1-10}$alkylC(O)S$R_{19}$, —C(O)$C_{2-10}$alkenylC(O)S$R_{19}$, —C(O)$C_{2-10}$alkynylC(O)S$R_{19}$.

—C(O)$C_{1-10}$alkyl—△—$R_{19}$,

—C(O)$C_{2-10}$alkenyl—△—$R_{19}$ or

—C(O)$C_{2-10}$alkynyl—△—$R_{19}$;

and $R_{19}$ is hydrogen, —$C_{1-10}$alkyl, —$C_{2-10}$alkenyl, —$C_{2-10}$alkynyl, cycloalkyl or aryl;

wherein each alkyl, alkenyl, alkynyl, cycloalkyl or aryl group is optionally substituted; or a geometric isomer or stereoisomer or a pharmaceutically acceptable salt thereof.

In some embodiments, the compound of formula (I) is an epoxy-tigliaen-3-one compound of formula (II):

(II)

wherein $R_3$, $R_6$, $R_7$, $R_8$, $R_9$, $R_{10}$, $R_{11}$, $R_{12}$, $R_{13}$ and $R_{15}$ are as defined for formula (I).

In some embodiments, the compound of formula (I) or (II) is a compound of formula (III):

wherein $R_7$, $R_8$, $R_{11}$, $R_{12}$, $R_{13}$ and $R_{15}$ are as defined for formula (I).

In particular embodiments of formula (I), formula (II) or formula (III), one or more of the following applies:

$R_1$ is hydrogen and $R_2$ is OH or —OC(O)$C_{1-6}$alkyl, —OC(O)$C_{2-6}$alkenyl or —OC(O)$C_{2-6}$alkynyl, or $R_1$ and $R_2$ together form a carbonyl group; especially where $R_1$ and $R_2$ together form a carbonyl group;

$R_3$ is hydrogen or —$C_{1-3}$alkyl, especially —$C_{1-3}$alkyl, more especially methyl;

$R_4$ is hydrogen or —OH, —OC(O)$C_{1-6}$alkyl, —OC(O)$C_{2-6}$alkenyl or —OC(O)$C_{2-6}$alkynyl and $R_5$ is hydrogen or —OH, —OC(O)$C_{1-6}$alkyl, —OC(O)$C_{2-6}$alkenyl or —OC(O)$C_{2-6}$alkynyl; or $R_4$ and $R_5$ together form a double bond or an epoxide; especially where $R_4$ and $R_5$ together form a double bond;

$R_6$ is hydrogen or —$C_{1-3}$-alkyl, especially —$C_{1-3}$-alkyl, more especially methyl;

$R_7$ is —OH, —OC(O)$C_{1-5}$alkyl, —OC(O)$C_{2-15}$alkenyl, —OC(O)$C_{2-15}$alkynyl, —OC(O)aryl wherein the aryl group is optionally substituted, —OC(O)$C_{1-15}$alkylaryl, —OC(O)$C_{1-10}$alkylC(O)H, —OC(O)$C_{2-10}$alkenylC(O)H, —OC(O)$C_{1-10}$alkylC(O)$C_{1-6}$alkyl, —OC(O)$C_{2-10}$alkenylC(O)$C_{1-6}$alkyl, —OC(O)$C_{1-10}$alkylCH(O$C_{1-3}$alkyl)(O$C_{1-3}$alkyl), —OC(O)$C_{2-10}$alkenylCH(O$C_{1-3}$alkyl)(O$C_{1-3}$alkyl, —OC(O)$C_{1-10}$alkylS$C_{1-6}$alkyl, —OC(O)$C_{2-10}$alkenylS$C_{1-6}$alkyl, —OC(O)$C_{1-10}$alkylC(O)O$C_{1-6}$alkyl or —OC(O)$C_{2-10}$alkylC(O)O$C_{1-6}$alkyl; especially —OH, —OC(O)$C_{1-15}$alkyl, —OC(O)$C_{2-12}$alkenyl, —OC(O)$C_{2-12}$alkynyl, —OC(O)aryl wherein the aryl group is optionally substituted, —OC(O)$C_{1-12}$alkylaryl, —OC(O)$C_{1-6}$alkylC(O)H, —OC(O)$C_{2-6}$alkenylC(O)H, —OC(O)$C_{1-6}$alkylC(O)$C_{1-6}$alkyl, —OC(O)$C_{2-6}$alkenylC(O)$C_{1-6}$alkyl, —OC(O)$C_{1-6}$alkylCH(O$C_{1-3}$alkyl)(O$C_{1-3}$alkyl), —OC(O)$C_{2-6}$alkenylCH (OC$_{1-3}$alkyl)(OC$_{1-3}$alkyl), —OC(O)C$_{1-6}$alkylSC$_{1-3}$alkyl, —OC(O)C$_{2-6}$alkenylSC$_{1-3}$alkyl, —OC(O)C$_{1-6}$alkylC(O)OC$_{1-3}$alkyl or —OC(O)C$_{2-6}$alkylC(O)OC$_{1-3}$alkyl;

R$_8$ is —OC(O)C$_{1-15}$alkyl, —OC(O)C$_{2-15}$alkenyl, —OC(O)C$_{2-15}$alkynyl, or —OC(O)aryl where the aryl group is optionally substituted, especially —OC(O)C$_{1-10}$alkyl, —OC(O)C$_{2-10}$alkenyl, —OC(O)C$_{2-10}$alkynyl or —OC(O)aryl where the aryl group is optionally substituted; more especially —OC(O)C$_{1-10}$alkyl, —C(O)C$_{2-10}$alkenyl and —OC(O)aryl where the aryl group is optionally substituted;

R$_9$ and R$_{10}$ are independently —C$_{1-3}$alkyl, especially where R$_9$ and R$_{10}$ are both methyl;

R$_{11}$ and R$_{12}$ together form an epoxide and R$_{13}$ is —OH, —OC(O)C$_{1-6}$alkyl, —OC(O)C$_{2-6}$alkenyl or —OC(O)C$_{2-6}$alkynyl, especially —OH or —C(O)C$_{1-3}$alkyl; or R$_{12}$ and R$_{13}$ together form an epoxide and R$_{11}$ is —OH, —OC(O)C$_{1-6}$alkyl, —OC(O)C$_{2-6}$alkenyl or —OC(O)C$_{2-6}$alkynyl, especially —OH; and R$_{14}$ is hydrogen, —C(O)C$_{1-6}$alkyl, —C(O)C$_{2-6}$alkenyl or —C(O)C$_{2-6}$alkynyl, especially hydrogen;

R$_{15}$ is hydrogen, —C(O)C$_{1-6}$alkyl, —C(O)C$_{2-6}$alkenyl or —C(O)C$_{2-6}$alkynyl, especially hydrogen or —C(O)C$_{1-3}$alkyl; and R$_{16}$ is hydrogen, —C(O)C$_{1-6}$alkyl, —C(O)C$_{2-6}$alkenyl or —C(O)C$_{2-6}$alkynyl, especially hydrogen.

In particular embodiments, the epoxy-tigliane compound is selected from one of the following compounds in Tables 1 to 6;

TABLE 1

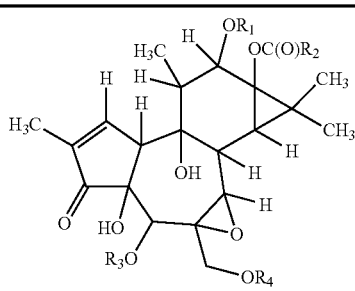

| Compound | R$_1$ | R$_2$ | R$_3$ | R$_4$ |
|---|---|---|---|---|
| 1 | CH$_3$-C(O)-C(CH$_3$)=CH-CH$_3$ | isobutyl | H | H |
| 2 | CH$_3$-C(O)-CH(CH$_3$)-CH$_2$-CH$_3$ | isobutyl | H | H |
| 3 | CH$_3$-C(O)-CH=CH-CH=CH-CH=CH-(CH$_2$)$_3$-CH$_3$ | isobutyl | H | H |
| 4 | CH$_3$-C(O)-CH=CH-CH=CH-(CH$_2$)$_4$-CH$_3$ | isobutyl | H | H |
| 5 | CH$_3$-C(O)-(CH$_2$)$_4$-CH$_3$ | isobutyl | H | H |
| 6 | CH$_3$-C(O)-CH$_3$ | isobutyl | H | H |
| 7 | CH$_3$-CH$_2$-C(O)-CH$_3$ | isobutyl | H | H |
| 8 | CH$_3$-C(O)-CH$_2$-CH$_2$-CH$_3$ | isobutyl | H | H |

TABLE 1-continued

[Core structure: diterpene scaffold with substituents OR₁, OC(O)R₂, OR₃, OR₄]

| Compound | R₁ | R₂ | R₃ | R₄ |
|---|---|---|---|---|
| 9 | CH₃-C(O)-CH=CH-CH=CH-CH(OCH₃)₂ | isobutyl (CH(CH₃)₂CH₃) | H | H |
| 10 | CH₃-C(O)-CH=CH-CH=CH-CHO | isobutyl | H | H |
| 11 | CH₃-C(O)-CH=CH-CH=CH-CH(OH)-CH(OH)-(CH₂)₄-CH₃ | isobutyl | H | H |
| 12 | CH₃-C(O)-CH=CH-CH(OH)-CH(OH)-(CH₂)₄-CH₃ | isobutyl | H | H |
| 13 | CH₃-C(O)-C(CH₃)=CH-CH₃ (with extra CH₃) | isopropyl (CH(CH₃)₂) | H | H |
| 14 | CH₃-C(O)-CH=CH-S-CH₃ | isobutyl | H | H |
| 15 | CH₃-C(O)-C(CH₃)=CH₂ | isobutyl | H | H |
| 16 | CH₃-C(O)-CH=CH-CH=CH-CH₃ | isobutyl | H | H |
| 17 | CH₃-C(O)-CH=CH-CH=CH-(CH₂)₂-C(O)-(CH₂)₃-CH₃ | isobutyl | H | H |

TABLE 1-continued
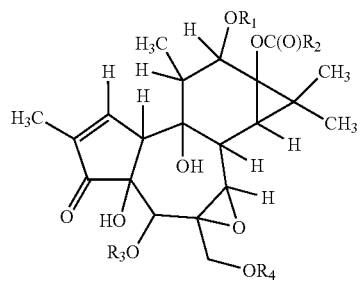
| Compound | R₁ | R₂ | R₃ | R₄ |
|---|---|---|---|---|
| 18 | (2-oxo-3,5-dodecadienyl group) | isobutyl (CH(CH₃)₂) | H | H |
| 19 | —H | isobutyl | H | H |
| 20 | CH₃C(O)CH=CHCH₃ | isobutyl | H | H |
| 21 | CH₃C(O)C(CH₃)=CHCH₃ | n-butyl | H | H |
| 22 | CH₃C(O)CH₂CH=CH₂ | n-octyl | H | H |
| 23 | C₆H₅C(O)— | isobutyl | H | H |
| 25 | (long-chain dienone) | isobutyl | H | H |
| 26 | (dienone with epoxide and pentyl chain) | isobutyl | H | H |

TABLE 1-continued
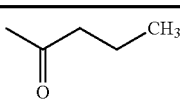
| Compound | R₁ | R₂ | R₃ | R₄ |
|---|---|---|---|---|
| 27 | 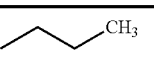 | 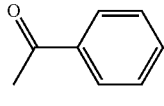 | H | H |
| 28 | 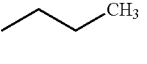 | 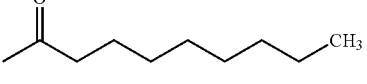 | H | H |
| 41 | 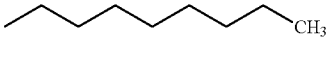 | 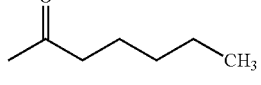 | H | H |
| 42 | 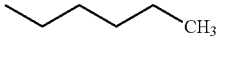 | 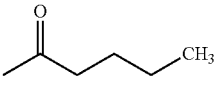 | H | H |
| 43 | 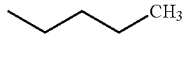 | 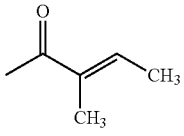 | H | H |
| 44 | 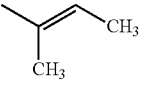 | 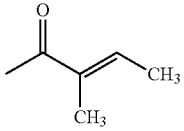 | H | H |
| 45 | 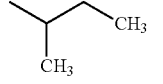 |  | 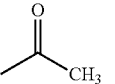 | 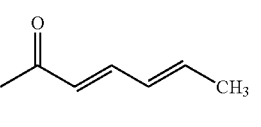 |
| 46 | 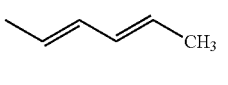 | 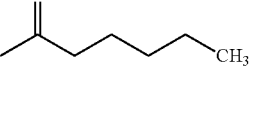 | H | H |
| 47 | 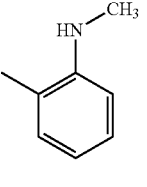 | 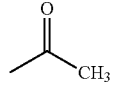 | H | H |
| 48 | 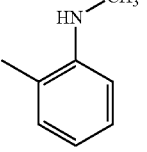 | 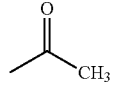 | H | H |

TABLE 1-continued

[Structure: diterpene core with substituents OR₁, OC(O)R₂, OR₃, OR₄, with OH, HO, epoxide, cyclopropane and cyclopentenone groups]

| Compound | R₁ | R₂ | R₃ | R₄ |
|---|---|---|---|---|
| 49 | –C(O)–(CH₂)₅–CH₃ | –(CH₂)₅–CH₃ | H | H |
| 50 | –C(O)–(CH₂)₁₂CH₃ | –CH₃ | H | H |
| 51 | –C(O)–(CH₂)₁₂CH₃ | –CH(CH₃)–CH₂–CH₃ (isobutyl) | H | H |
| 52 | –C(O)–CH(CH₃)–CH₂CH₃ | –CH₃ | H | H |
| 53 | –H | –(CH₂)₃–CH₃ | H | H |
| 60 | –C(O)–CH₂–CH(CH₃)₂ | –CH(CH₃)–CH₂CH₃ | H | H |

TABLE 2

[Structure: related diterpene core with OR₁, OC(O)R₂ substituents, free OH, HO, and CH₂OH groups]

| Compound | R₁ | R₂ |
|---|---|---|
| 24 | –C(O)–CH=CH–CH=CH–(CH₂)₃–CH₃ | –CH(CH₃)–CH₂CH₃ |

TABLE 3
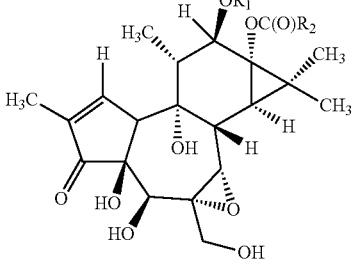
| Compound | R₁ | R₂ |
|---|---|---|
| 54 |  | 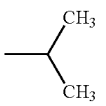 |
| 55 | 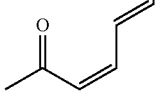 | 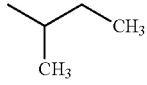 |
| 56 | 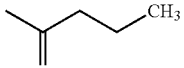 | 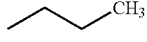 |
| 57 | 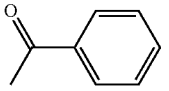 | 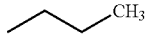 |
TABLE 4
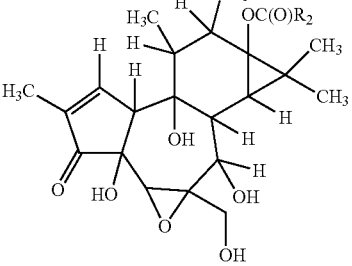
| Compound | R₁ | R₂ |
|---|---|---|
| 29 | 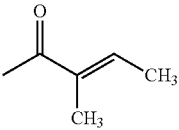 | 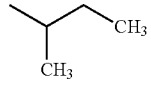 |
| 30 | —H | 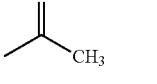 |
TABLE 4-continued
| Compound | R₁ | R₂ |
|---|---|---|
| 31 |  | 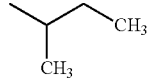 |
| 32 | 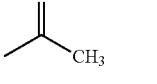 |  |

TABLE 4-continued

[Structure: tigliane/daphnane-type diterpene core with OR₁ and OC(O)R₂ substituents]

| Compound | R₁ | R₂ |
|---|---|---|
| 33 | C(O)CH₂CH₃ (propanoyl) | CH(CH₃)CH₂CH₃ (sec-butyl / 2-methylpropyl) |
| 34 | C(O)CH₂CH₂CH₂CH₂CH₃ (hexanoyl) | CH₂CH(CH₃)₂ (isobutyl) |
| 35 | C(O)C(CH₃)=CHCH₃ (tiglyl-type, 2-methyl-2-butenoyl) | CH(CH₃)₂ (isopropyl) |
| 36 | C(O)CH=CH-SCH₃ | CH₂CH(CH₃)₂ |
| 39 | C(O)CH₂C(O)SCH₃ | CH₂CH(CH₃)₂ |
| 40 | C(O)CH₂C(O)OCH₃ | CH₂CH(CH₃)₂ |

TABLE 5

[Structure: related diterpene core with OR₁ and OC(O)R₂ substituents]

| Compound | R₁ | R₂ |
|---|---|---|
| 37 | C(O)C(CH₃)=CHCH₃ | CH(CH₃)CH₂CH₃ |

TABLE 6

[Structure: related diterpene core with OR₁ and OC(O)R₂ substituents]

| Compound | R₁ | R₂ |
|---|---|---|
| 38 | C(O)CH(CH₃)CH₂CH₃ (2-methylbutanoyl) | CH(CH₃)CH₂CH₃ |
| 58 | C(O)CH₂C(O)SCH₃ | CH₂CH(CH₃)₂ |
| 59 | C(O)CH₂C(O)OCH₃ | CH₂CH(CH₃)₂ |

The compounds of the present invention may be in the form of a pure compound or in the form of a plant extract.

Where the compounds are depicted as having stereochemistry, the stereochemistry depicted is relative stereochemistry and is based on knowledge of biosynthesis pathways and chemical analysis.

In some embodiments, the plant extract is from a plant of the genus *Fontainea* or *Hylandia*, especially the species is *Fontainea pancheri*, *Fontainea australis*, *Fontainea borealis*, *Fontainea fugax*, *Fontainea oraria*, *Fontainea picrosperma*, *Fontainea rostrata*, *Fontainea subpapuana*, *Fontainea venosa* of *Hylandia dockrillii*, especially *Fontainea picrosperma*, *Fontainea australis*, *Fontainea rostrata* or *Hylandia dockrillii*.

The parts of the plant may include fruit, seed, bark, stem, leaf, flower, roots, endosperm, exocarp and wood, especially where the extract is obtained from the seed.

Extracts of the plants may be obtained by standard methods, for example, the biomass obtained from seeds, leaves, fruit, endosperm, exocarp, stem or bark of the plant is subject to initial solvent extraction, such as with a polar solvent for example, ethanol. The initial extraction is then concentrated and diluted with water and subject to extraction with a second solvent, for example, ethyl acetate. The solvent samples from the second extraction are pooled and subject to separation by preparative HPLC fractionation. The fractions are analysed by analytical HPLC and pooled according to the retention time of compounds found in the samples. The pooled fractions are weighed, bioassayed and analysed by analytical HPLC. Further fractionation using one or more preparative HPLC is performed to isolate specific compounds. Each compound is bioassayed and its structure identified by UV, NMR and mass spectrometric techniques.

Other compounds of the invention may be obtained by derivatising compounds isolated from plants or parts of plants, especially from the genus *Fontainea*, especially from the species *Fontainea picrosperma*, especially the seeds of *Fontainea picrosperma*.

Derivatives of the natural compounds can be obtained by techniques known in the art. For example, hydroxy groups may be oxidised to ketones, aldehydes or carboxylic acids by exposure to oxidising agents such as chromic acid, Jones' reagent, $KMnO_4$, peracids such as mCPBA (metachloroperbenzoic acid) or dioxiranes such as dimethyldioxirane (DMDO) and methyl(trifluoromethyl)dioxirane (TFDO). Oxidising agents may be chosen such that other functional groups in the molecule are or are not also oxidised. For example, a primary alcohol may be selectively oxidised to an aldehyde or carboxylic acid in the presence of secondary alcohols using reagents such as $RuCl_2(PPh_3)_3$-benzene. Secondary alcohols may be selectively oxidised to ketones in the presence of a primary alcohol using $Cl_2$-pyridine or $NaBrO_3$-ceric-ammonium nitrate. Alcohols may be oxidised in the presence of double and triple bonds and without epimerisation at adjacent stereocentres using Jones' reagent with or without Celite (or ammonium chloride). Alternatively, reagents chosen may be less selective resulting in oxidation at more than one functional group.

Hydroxy groups may also be derivatised by etherification or acylation. For example, ethers may be prepared by formation of an alkoxide ion in the presence of base and reacting the alkoxide with an appropriate alkylhalide, alkenylhalide, alkynylhalide or arylhalide. Similarly acylation may be achieved by formation of an alkoxide ion and reaction with an appropriate carboxylic acid or activated carboxylic acid (such as an anhydride or acylchloride).

Acyl groups may be hydrolysed to provide alcohols by acid or base hydrolysis as known in the art and those alcohols can be derivatised further as above.

Ketones may be reduced to secondary alcohols by reducing agents such as lithium aluminium hydride and other metal hydrides without reducing double bonds, including $\alpha$-unsaturated ketones.

Double bonds and triple bonds may be reduced to single bonds using catalytic reduction, for example, $H_2$/Pd. Double bonds may also be oxidised to epoxides using oxidising agents such as peracids, for example mCPBA or dioxiranes, such as DMDO and TFDO. Double bonds may also be subject to addition reactions to introduce substituents such as halo groups, hydroxy or alkoxy groups.

A person skilled in the art would be able to determine suitable conditions for obtaining derivatives of isolated compounds, for example, by reference to texts relating to synthetic methodology, examples of which are Smith M. B. and March J., March's Advanced Organic Chemistry, Fifth Edition, John Wiley & Sons Inc., 2001 and Larock R. C., Comprehensive Organic Transformations, VCH Publishers Ltd., 1989. Furthermore, selective manipulations of functional groups may require protection of other functional groups. Suitable protecting groups to prevent unwanted side reactions are provided in Green and Wuts, Protective Groups in Organic Synthesis, John Wiley & Sons Inc., 3rd Edition, 1999.

Compounds of the Invention

In another aspect of the invention, there are novel compounds including:

12-hexanoyl-13-(2-methylbutanoyl)-6,7-epoxy-4,5,9,12,13,20-hexahydroxy-1-tigliaen-3-one (Compound 5);

12-acetyl-13-(2-methylbutanoyl)-6,7-epoxy-4,5,9,12,13,20-hexahydroxy-1-tigliaen-3-one (Compound 6);

12-propanoyl-13-(2-methylbutanoyl)-6,7-epoxy-4,5,9,12,13,20-hexahydroxy-1-tigliaen-3-one (Compound 7);

12-butanoyl-13-(2-methylbutanoyl)-6,7-epoxy-4,5,9,12,13,20-hexahydroxy-1-tigliaen-3-one (Compound 8);

12-[(2E,4E)-(6,6-dimethoxyhexa-2,4-dienoyl]-13-(2-methylbutanoyl)-6,7-epoxy-4,5,9,12,13,20-hexahydroxy-1-tigliaen-3-one (Compound 9);

12-[(2E,4E)-6-oxohexa-2,4-dienoyl]-13-(2-methylbutanoyl)-6,7-epoxy-4,5,9,12,13,20-hexahydroxy-1-tigliaen-3-one (Compound 10);

12-[(2E,4E)-6,7-dihydroxydodeca-2,4-dienoyl]-13-(2-methylbutanoyl)-6,7-epoxy-4,5,9,12,13,20-hexahydroxy-1-tigliaen-3-one (Compound 11);

12-[(2E)-4,5-dihydroxy-deca-2-enoyl]-13-(2-methylbutanoyl)-6,7-epoxy-4,5,9,12,13,20-hexahydroxy-1-tigliaen-3-one (Compound 12);

12-tigloyl-13-(2-methylpropanoyl)-6,7-epoxy-4,5,9,12,13,20-hexahydroxy-1-tigliaen-3-one (Compound 13);

12-[(2E)-3-methylthioprop-2-enoyl]-13-(2-methylbutanoyl)-6,7-epoxy-4,5,9,12,13,20-hexahydroxy-1-tigliaen-3-one (Compound 14);

12-(2-methylprop-2-enoyl-13-methylbutanoyl)-6,7-epoxy-4,5,9,12,13,20-hexahydroxy-1-tigliaen-3-one (Compound 15);

12-[(2E,4E)-hexa-2,4-dienoyl]-13-(2-methylbutanoyl)-6,7-epoxy-4,5,9,12,13,20-hexahydroxy-1-tigliaen-3-one (Compound 16);

12-[(2E,4E)-8-oxododeca-2,4-dienoyl]-13-(2-methylbutanoyl)-6,7-epoxy-4,5,9,12,13,20-hexahydroxy-1-tigliaen-3-one (Compound 17);

12-[(2Z,4E)-deca-2,4-dienoyl]-13-(2-methylbutanoyl)-6,7-epoxy-4,5,9,12,13,20-hexahydroxy-1-tigliaen-3-one (Compound 18);

13-(2-methylbutanoyl)-6,7-epoxy-4,5,9,12,13,20-hexahydroxy-1-tigliaen-3-one (Compound 19);

12-[(2E)-but-2-enoyl]-13-(2-methylbutanoyl)-6,7-epoxy-4,5,9,12,13,20-hexahydroxy-1-tigliaen-3-one (Compound 20);

12-tigloyl-13-butanoyl-6,7-epoxy-4,5,9,12,13,20-hexahydroxy-1-tigliaen-3-one (Compound 21);

12-(3-butenoyl)-13-nonanoyl-6,7-epoxy-4,5,9,12,13,20-hexahydroxy-1-tigliaen-3-one (Compound 22);

12-benzoyl-13-(2-methylbutanoyl)-6,7-epoxy-4,5,9,12,13,20-hexahydroxy-1-tigliaen-3-one (Compound 23);

12-[(2Z,4E)-deca-2,4-dienoyl]-13-(2-methylpropanoyl)-6,7-epoxy-4,5,9,12,13,20-hexahydroxy-1-tigliaen-3-one (Compound 25);

12-[(2E,4E)-6,7-(anti)-epoxy-dodeca-2,4-dienoyl]-13-(2-methylbutanoyl)-6,7-epoxy-4,5,9,12,13,20-hexahydroxy-1-tigliaen-3-one (Compound 26);

12,13-dibutanoyl-6,7-epoxy-4,5,9,12,13,20-hexahydroxy-1-tigliaen-3-one (Compound 27);

12-benzoyl-13-butanoyl-6,7-epoxy-4,5,9,12,13,20-hexahydroxy-1-tigliaen-3-one (Compound 28);

12-tigloyl-13-(2-methylbutanoyl)-5,6-epoxy-4,7,9,12,13,20-hexahydroxy-1-tigliaen-3-one (Compound 29);

13-(2-methylbutanoyl)-5,6-epoxy-4,7,9,12,13,20-hexahydroxy-1-tigliaen-3-one (Compound 30);

12-acetyl-13-(2-methylbutanoyl)-5,6-epoxy-4,7,9,13,20-hexahydroxy-1-tigliaen-3-one (Compound 31);

12,13-di-(2-methylbutanoyl)-5,6-epoxy-4,7,9,13,20-hexahydroxy-1-tigliaen-3-one (Compound 32);

12-propanoyl-13-(2-methylbutanoyl)-5,6-epoxy-4,7,9,12,13,20-hexahydroxy-1-tigliaen-3-one (Compound 33);

12-hexanoyl-13-(2-methylbutanoyl)-5,6-epoxy-4,7,9,12,13,20-hexahydroxy-1-tigliaen-3-one (Compound 34);

12-tigloyl-13-(2-methylpropanoyl)-5,6-epoxy-4,7,9,12,13, 20-hexahydroxy-1-tigliaen-3-one (Compound 35);

12-[(2E)-3-methylthioprop-2-enoyl]-13-(2-methylbutanoyl)-5,6-epoxy-4,7,9,12,13,20-hexahydroxy-1-tigliaen-3-one (Compound 36);

12-{[2-(methylsulfanyl)carbonyl]-acetoyl}-13-(2-methylbutanoyl)-5,6-epoxy-4,7,9,12,13,20-hexahydroxy-1-tigliaen-3-one (Compound 39);

12-[(2-methoxycarbonyl)-acetoyl]-13-(2-methylbutanoyl)-5,6-epoxy-4,7,9,12,13,20-hexahydroxy-1-tigliaen-3-one (Compound 40);

12,13-di-nonoyl-6,7-epoxy-4,5,9,12,13,20-hexahydroxy-1-tigliaen-3-one (Compound 41);

12,13-di-hexanoyl-6,7-epoxy-4,5,9,12,13,20-hexahydroxy-1-tigliaen-3-one (Compound 42);

12,13-di-pentanoyl-6,7-epoxy-4,5,9,12,13,20-hexahydroxy-1-tigliaen-3-one (Compound 43);

12,13-di-tigloyl-6,7-epoxy-4,5,9,12,13,20-hexahydroxy-1-tigliaen-3-one (Compound 44)

5,20-diacetyl-12-tigloyl-13-(2-methylbutanoyl)-6,7-epoxy-4,5,9,12,13,20-hexahydroxy-1-tigliaen-3-one (Compound 45);

12,13-di-(2E,4E)-hex-2,4-enoyl-6,7-epoxy-4,5,9,12,13,20-hexahydroxy-1-tigliaen-3-one (Compound 46);

12-hexanoyl-13-[2-(N-methylanthraniloyl)]-6,7-epoxy-4,5,9,12,13,20-hexahydroxy-1-tigliaen-3-one (Compound 47)

12-acetyl-13-[2-(N-methylanthraniloyl)]-6,7-epoxy-4,5,9,12,13,20-hexahydroxy-1-tigliaen-3-one (Compound 48);

12,13-di-heptanoyl-6,7-epoxy-4,5,9,12,13,20-hexahydroxy-1-tigliaen-3-one (Compound 49);

12-myristoyl-13-acetyl-6,7-epoxy-4,5,9,12,13,20-hexahydroxy-1-tigliaen-3-one (Compound 50);

12-myristoyl-13-(2-methylbutanoyl)-6,7-epoxy-4,5,9,12, 13,20-hexahydroxy-1-tigliaen-3-one (Compound 51);

12-(2-methylbutanoyl)-13-acetyl-6,7-epoxy-4,5,9,12,13,20-hexahydroxy-1-tigliaen-3-one (Compound 52); and 13-hexanoyl-6,7-epoxy-4,5,9,12,13,20-hexahydroxy-1-tigliaen-3-one (Compound 53);

12,13-di-(3-methylbutanoyl)-6,7-epoxy-4,5,9,12,13,20-hexahydroxy-1-tigliaen-3one (Compound 60)

or a pharmaceutically acceptable salt thereof.

In yet another aspect of the invention, any one of the compounds 5 to 53 or 60 or a pharmaceutically acceptable salt thereof may be in the form of a pharmaceutical composition together with a pharmaceutically acceptable carrier, diluent and/or excipient.

Compositions

While the epoxy-tigliane compounds or a pharmaceutically acceptable salts thereof, may be administered neat, it may be more convenient to administer the epoxy-tigliane compounds in the form of a pharmaceutical composition together with a pharmaceutically acceptable carrier, diluent and/or excipient.

Dosage form and rates for pharmaceutical use and compositions are readily determinable by a person of skill in the art.

Dosage forms include tablets, dispersions, suspensions, injections, solutions, syrups, troches, capsules, suppositories, aerosols, transdermal patches, impregnated (occlusive) dressing, creams, gels and the like. These dosage forms may also include injecting or implanting devices designed specifically for, or modified to, controlled release of the pharmaceutical composition. Controlled release of the therapeutic agent may be effected by coating the same, for example, with hydrophobic polymers including acrylic resins, waxes, higher aliphatic alcohols, polyactic and polyglycolic acids and certain cellulose derivates such as hydroxypropylmethyl cellulose. In addition, the controlled release may be affected by using other polymer matrices, liposomes and/or microspheres.

Pharmaceutically acceptable carriers and acceptable carriers for systemic administration may also be incorporated into the compositions of this invention.

Suitably, the pharmaceutical composition comprises a pharmaceutically acceptable excipient or an acceptable excipient. By "pharmaceutically acceptable excipient" is meant a solid or liquid filler, diluent or encapsulating substance that may be safely used. Depending upon the particular route of administration, a variety of carriers, well known in the art may be used. These carriers or excipients may be selected from a group including sugars, starches, cellulose and its derivates, malt, gelatine or other gelling agents, talc, calcium sulphate, vegetable oils, synthetic oils, alcohols and/or polyols, alginic acid, phosphate buffered solutions, emulsifiers, isotonic saline, and pyrogen-free water.

Any suitable route of administration may be employed for providing a human or non-human patient with the pharmaceutical composition of the invention. For example, oral, topical, rectal, parenteral, sublingual, buccal, intravenous, intraarticular, intra-muscular, intra-dermal, subcutaneous, inhalational, intraocular, intraperitoneal, intracerebroventricular, transdermal and the like may be employed.

Pharmaceutical compositions of the present invention suitable for administration may be presented in discrete units such as syringes, vials, tubes, capsules, sachets or tablets each containing a predetermined amount of one or more pharmaceutically active compounds or extracts of the invention, as a powder or granules or as a solution or a suspension in an aqueous liquid, a cyclodextrin solution, a non-aqueous liquid, an oil-in-water emulsion or a water-in-oil emulsion or as a solution or suspension in a cream or gel or as a suspension of micro- or nano-particles incorporating a compound of the invention, including but not limited to silica or polylactide micro- or nano-particles. Such compositions may be prepared by any of the method of pharmacy but all methods include the step of bringing into association one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

In powders, the carrier is a finely divided solid which is in a mixture with the finely divided active component.

In tablets, the active component is mixed with the carrier having the necessary binding capacity in suitable proportions and compacted in the shape and size desired.

Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous 1,2-propanediol, dimethylsulfoxide (DMSO), aqueous solutions of gamma cyclodextrin or 2-hydroxypropyl-beta-cyclodextrin, saline solution or polyethylene glycol solution, with or without buffer. A preferred range of pH is 3.5-4.5. Suitable buffers buffer the preparation at pH 3.5-4.5 and include, but are not limited to, acetate buffer and citrate buffer.

The compounds according to the present invention may thus be formulated for parenteral administration (e.g. by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis or other organ, the compounds according to the invention may be formulated as gels, ointments, emulsions, pastes, creams or lotions, or as a transdermal patch. Gels may be prepared using suitable thickening agents and adding them to aqueous/alcoholic compositions of compound. Suitable thickening or gelling agents are known in the art, such as the polyvinyl carboxy polymer, Carbomer 940. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration also include solutions or suspensions that may be administered topically in the form of a bath or soak solution or a spray. These formulations may be suitably applied to combat skin irritations, insect bites and foot wounds.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarhon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

The invention will now be described with reference to the following Examples which illustrate some preferred aspects of the present invention. However, it is to be understood that the particularity of the following description of the invention is not to supersede the generality of the preceding description of the invention.

EXAMPLES

Example 1: Plant Extracts

Figure 1:
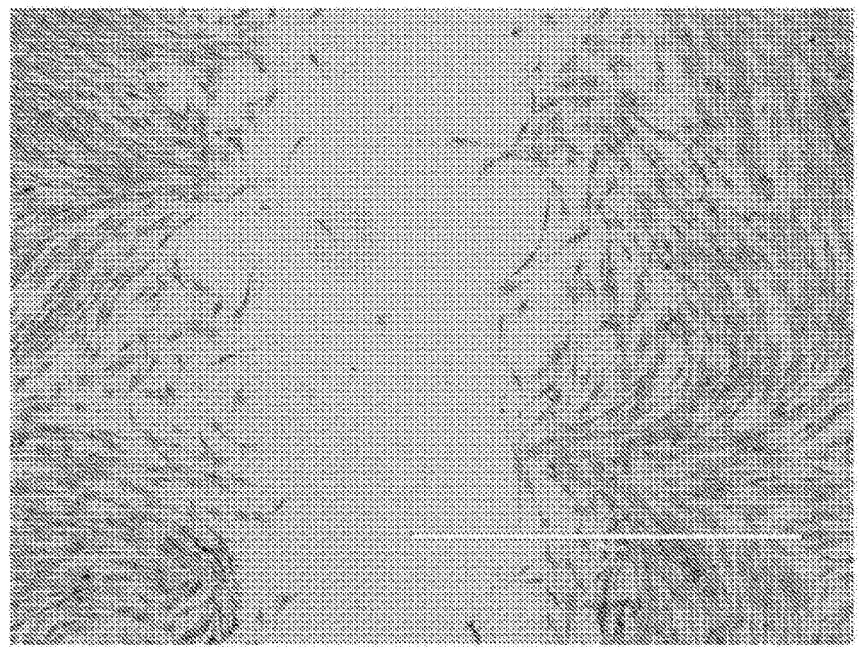
FIG. 1 is a photographic representation of scratch closure in human neonatal fibroblast cells treated with the vehicle-only control, 24 hours post scratch.

All plant extracts were prepared by chopping the plant material and extracting with ethanol in an approximate ratio of 1 part plant material to between 2 to 5 parts of ethanol (w/w). The extract was allowed to stand overnight at 4° C. and then the supernatant as decanted and stored at 4° C. until use.

The presence of epoxy-tigliane compounds in the plant extracts was confirmed by LCMSMS using a Shimadzu HPLC coupled to an ABI3200 triple quadrupole mass spectrometer. A halo amide C18 column was employed to separate the compounds in the mixtures, using acetonitrile/water mixtures as the solvent system.

Most of the samples were run with the KinC18Gen method, using a C18 Kinetix 4.6 mm×100 mm 2.6 micron C18 column:

| | | Acetonitrile: | | | |
|---|---|---|---|---|---|
| 55% | 60% | 75% | 100% | 100% | 55% |
| Minutes: 0 | 2.5 | 15 | 15.1 | 17.5 | 17.6 |

Some of the samples were run with the Amide Long method using a Halo amide column RP 4.6 mm×150 mm, 2.7 micron, from Advanced Materials Technology:

| | | Acetonitrile: | | | |
|---|---|---|---|---|---|
| 45% | 58% | 95% | 95% | 45% | 45% |
| Minutes: 0 | 13 | 20 | 24 | 24.1 | 27 |

Example 2: Isolation and Elucidation of Epoxy-Tigliane Compounds

Compounds were purified from the seeds of *Fontainea picrosperma* by extraction, and chromatography on silica gel followed by preparative HPLC (C18 Column, methanol/water solvent combinations) using the general methods described below.

Approximately 1-2 kg of plant material (leaves, fruit, seed, stems, roots flowers, bark or wood) is finely chopped, extracted with 2 parts of ethanol (w/v) three times, the extracts combined, evaporated and the residue partitioned between water and an immiscible organic solvent (typically petroleum spirit bp 40-60 (PE) or ethyl acetate EtOAc). The residue from evaporation of the organic solvent is chromatographed on silica gel in solvent mixtures of increasing polarity, commencing with PE or heptane and progressing to EtOAc and then methanol. The fractions from silica gel are then further purified by preparative HPLC on C18 columns typically using methanol-water gradients. The latter fractions are analysed for bioactivity, pooled according to the retention time of compounds found by analytical HPLC, and subjected to further preparative HPLC to obtain pure compounds. Each compound is bioassayed and its structure confirmed by UV, NMR and mass spectrometric techniques.

Compound 1: 12-tigloyl-13-(2-methylbutanoyl)-6,7-epoxy-4,5,9,12,13,20-hexahydroxy-1-tigliaen-3-one

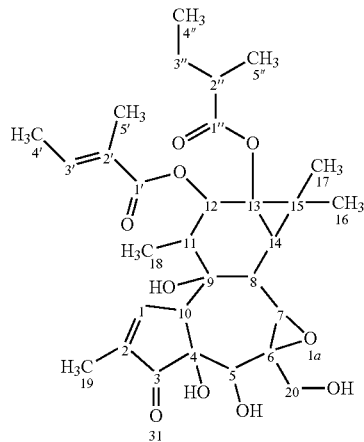

$^1$H NMR (500 MHz, CDCl$_3$) δ ppm: 0.84 (3H (18), d, J=6.4 Hz), 0.92 (3H (4"), t, J=7.3 Hz), 1.11 (3H (5"), d, J=6.8 Hz), 1.21 (3H (16), s), 1.24 (3H (17), s), 1.26 (1H (14), d, J=6.8 Hz), 1.43 (1H (3"), m, J=14.1, 7.3, 7.2 Hz), 1.69 (1H (3"), m), 1.73 (3H (19), dd, J=2.9, 1.5 Hz), 1.77 (3H (4'), dd, J=7.1, 1.2 Hz), 1.8 (3H (5'), d, J=1.5 Hz), 1.94 (1H (11), m), 2.37 (1H (2"), qt, J=7.0, 6.8 Hz), 3.17 (1H (8), d), 3.26 (1H (7), s), 3.69 (1H, OH, br.s), 3.80, (1H (20), d, J=12.7 Hz), 3.83 (1H (20), d, J=12.2 Hz), 4.06 (1H (10), t, J=2.7 Hz), 4.22 (1H (5), s), 5.42 (1H (12), d, J=9.8 Hz), 6.02 (1H, OH, br.s), 6.79 (1H (3'), m, J=7.2, 7.0, 1.2 Hz), 7.71 (1H (1), dd).

$^{13}$C NMR (125 MHz, CDCl$_3$) δ ppm: 9.7 (19), 11.6 (4"), 12.2 (5'), 14.4 (4'), 15.1 (18), 16.1 (5"), 17.2 (16), 23.6 (17), 26.1 (3"), 26.6 (15), 36.0 (8), 36.1 (14), 41.2 (2"), 45.9 (11), 48.9 (10,) 61.8 (6), 64.6 (20), 65.2 (7), 65.5 (13), 71.3 (5), 72.4 (4), 76.7 (12), 77.2 (9), 128.4 (2'), 133.4 (2), 137.6 (3'), 164.7 (1), 167.4 (1'), 178.9 (1"), 209.9 (3).

Compound 2: 12,13-di-(2-methylbutanoyl)-6,7-epoxy-4,5,9,12,13,20-hexahydroxy-1-tigliaen-3-one

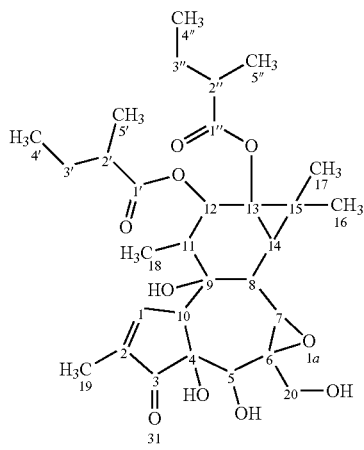

$^{1}$H NMR (500 MHz, CDCl$_3$) δ ppm: 0.85 (3H (18), d, J=6.4 Hz), 0.89 (3H (4"), J=7.3 Hz), 0.91 (3H (4'), t, J=7.8 Hz), 1.11 (3H (5"), d, J=6.8 Hz), 1.12 (3H (5'), d, J=6.8 Hz), 1.21 (3H (17), s), 1.22 (3H (16), s), 1.26 (1H (14), d, J=6.8 Hz), 1.44 (1H (3'), td, J=13.9, 7.3 Hz), 1.44 (1H (3"), td, J=13.9, 7.3 Hz), 1.63 (1H (3'), dd, J=7.8, 5.9 Hz), 1.69 (1H (3"), dd, J=13.9, 7.1 Hz), 1.74 (3H (19), dd, J=2.7, 1.2 Hz), 1.90 (1H (11), dd, J=10.0, 6.6 Hz), 2.36 (1H (2'), q, J=7.0 Hz), 2.36 (1H (2"), q, J=7.0 Hz), 3.16 (1H (8), d, J=6.8 Hz), 3.26 (1H (7), s), 3.61 (1H (OH), m), 3.78 (1H (20), m, J=12.7 Hz), 3.85 (1H (20), d, J=12.2 Hz), 4.06 (1H (10), t, J=2.7 Hz), 4.22 (1H (5), s), 5.40 (1H (12), d, J=10.3 Hz), 5.98 (1H (9-OH), m), 7.71 (1H (1), dd, J=2.4, 1.5 Hz).

$^{13}$C NMR (125 MHz, CDCl$_3$) δ ppm: 9.7 (19), 11.6 (4'), 11.6 (4"), 15.0 (18), 16.1 (5"), 17.0 (5'), 17.2 (17), 23.7 (16), 26.2 (3"), 26.5 (15), 26.7 (3'), 36.0 (8), 36.0 (14), 41.2 (2"), 41.8 (2'), 45.5 (11), 48.9 (10), 61.7 (6), 64.5 (20), 65.2 (7), 65.5 (13), 71.5 (5), 72.4 (4), 76.2 (12), 77.2 (9), 133.5 (2), 164.7 (1), 175.9 (1'), 178.8 (1"), 209.9 (3), Compound 3: 12-[(2E,4E,6E)-dodeca-2,4,6-trienoyl]-13-(2-methylbutanoyl)-6,7-epoxy-4,5,9,12,13,20-hexahydroxy-1-tigliaen-3-one

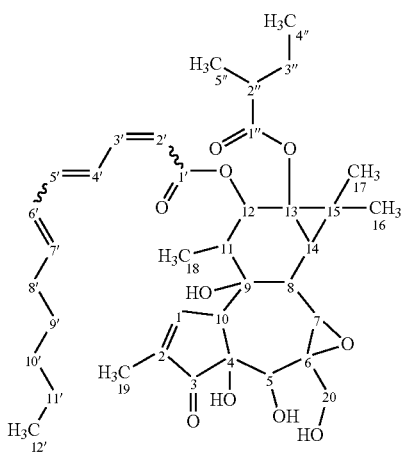

$^{1}$H NMR (500 MHz, CDCl$_3$) δ ppm: 0.86 (3H (18), d, J=7.0 Hz), 0.87 (3H (12'), m, J=7.0 Hz), 0.92 (3H (4"), t, J=7.5 Hz), 1.12 (3H (5"), d, J=7.5 Hz), 1.22 (3H (17), s), 1.24 (3H (16), s), 1.26 (2H (10'), m), 1.27 (1H (14), m), 1.29 (2H (11'), m), 1.39 (2H (9'), m), 1.45 (1H (3"), dd, J=14.1, 7.0 Hz), 1.71 (1H (3"), m), 1.74 (3H (19), dd, J=2.8, 1.2 Hz), 1.95 (1H (11), dq), 2.12 (2H (8'), q), 2.38 (1H (2"), sxt, J=7.0 Hz), 3.17 (1H (8), d, J=6.7 Hz), 3.27 (1H (7), s), 3.57 (1H, (4-OH), s), (3.78 (1H (20), m), 3.86 (1H (20), m), 4.06 (1H (10), d, J=2.7 Hz), 4.22 (1H (5), s), 5.41 (1H (12), d), 5.79 (1H (2'), d, J=15.2 Hz), 5.92 (1H (7'), dt, J=15.2, 7.2 Hz), 6.04 (1H (OH), m), 6.11 (1H (6'), dd, J=15.1, 10.7 Hz), 6.19 (1H (4'), dd, J=14.8, 11.2 Hz), 6.51 (1H (5'), dd, J=14.9, 10.7 Hz), 7.23 (1H (3'), dd, J=15.5, 10.9 Hz), 7.72 (1H (1), dd, J=2.4, 1.3 Hz).

$^{13}$C NMR (125 MHz, CDCl$_3$) δ ppm: 9.7 (19), 11.6 (4"), 14.0 (12'), 15.1 (18), 16.2 (5"), 17.2 (16), 22.5 (11'), 23.6 (17), 26.2 (3"), 26.7 (15), 28.6 (9'), 31.4 (10'), 33.0 (8'), 36.0 (8), 36.2 (14), 41.2 (2"), 45.9 (11), 48.9 (10), 61.6 (6), 64.5 (20), 65.3 (7), 65.5 (13), 71.6 (5), 72.4 (4), 76.7 (9), 77.1 (12), 119.5 (2'), 127.5 (4'), 129.7 (6'), 133.5 (2), 141.1 (7'), 141.7 (5'), 145.3 (3'), 164.8 (1), 166.6 (1'), 170.0 (1"), 210.0 (3).

Compound 4: 12-[(2E,4Z)-deca-2,4-dienoyl]-13-(2-methylbutanoyl)-6,7-epoxy-4,5,9,12,13,20-hexahydroxy-1-tigliaen-3-one

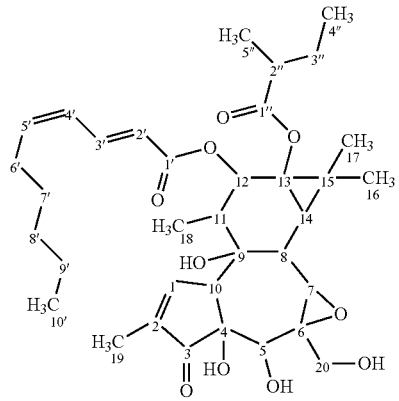

$^{1}$H NMR (500 MHz, CDCl$_3$) δ ppm: 0.87 (3H (18), d, J=6.4 Hz), 0.87 (3H (10'), s), 0.93 (3H (4"), t, J=7.5 Hz), 1.13 (3H (5"), d, J=7.1. Hz), 1.23 (3H (16), s), 1.25 (3H (17), s), 1.27 (1H (14), d, J=1.6 Hz), 1.27 (2H (9'), m), 1.30 (2H (8'), m), 1.40 (2H (7'), m), 1.46 (1H (3"), dd, J=14.2, 6.9 Hz), 1.71 (1H (3"), m), 1.75 (3H (19), dd, J=2.9, 1.3 Hz), 1.95 (1H (11), d, J=3.3 Hz), 2.11 (1H (20-OH), m), 2.26 (2H (6'), m), 2.38 (1H (2"), q, J=7.0 Hz), 3.18 (1H (8), d, J=6.6 Hz), 3.28 (1H (7), s), 3.53 (1H (4-OH), d, J=0.9 Hz), 3.77 (1H (20), m), 3.81 (1H (5-OH), d, J=2.8 Hz), 3.87 (1H (20), dd, J=12.4, 7.6 Hz), 4.06 (1H (10), d, J=2.7 Hz), 4.22 (1H (5), d, J=1.7 Hz), 5.43 (1H (12), d, J=9.9 Hz), 5.83 (1H (2'), d, J=15.2 Hz), 5.86 (1H (5'), ddd, J=10.8, 7.9, 7.8 Hz), 6.03 (1H (9-OH), m), 6.10 (1H (4'), td, J=11.2, 0.7 Hz), 7.56 (1H (3'), ddd, J=15.3, 11.7, 1.1 Hz), 7.72 (1H (1), dd, J=2.5, 1.4 Hz).

$^{13}$C NMR (125 MHz, CDCl$_3$) δ ppm: 9.7 (19), 11.6 (4"), 14.0 (10'), 15.2 (18), 16.2 (5"), 17.2 (17), 22.5 (9'), 23.7 (16), 26.2 (3"), 26.7 (15), 28.3 (6'), 29.0 (7'), 31.4 (8'), 36.1 (8), 36.2 (14), 41.2 (2"), 45.9 (11), 49.0 (10), 61.6 (6), 64.5 (20), 65.3 (7), 65.5 (13), 71.7 (5), 72.3 (4), 76.8 (12), 77.1 (9), 120.8 (2'), 126.4 (4'), 133.5 (2), 140.0 (3'), 142.2 (5'), 164.8 (1), 166.6 (1'), 179.0 (1"), 210.0 (3).

Compound 5: 12-hexanoyl-13-(2-methylbutanoyl)-6,7-epoxy-4,5,9,12,13,20-hexahydroxy-1-tigliaen-3-one

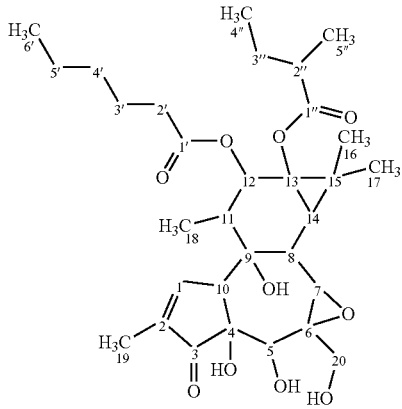

¹H NMR (500 MHz, CDCl₃) δ ppm: 0.84 (3H (18), d, J=6.5 Hz), 0.87 (3H (6'), t, J=7.0 Hz), 0.91 (3H (4"), t, J=7.5 Hz), 1.11 (3H (5"), d, J=7.0 Hz), 1.21, (3H (16), s), 1.21, (3H (17), s), 1.25 (1H (14), d, J=6.6 Hz), 1.43 (1H (3"), m, J=14.1, 7.4, 7.1 Hz), 1.60 (2H (3'), quin, J=7.4 Hz), 1.70 (1H (3"), ddd, J=13.9, 7.3, 7.1 Hz), 1.74 (3H (19), dd, J=2.9, 1.3 Hz), 1.9 (1H (11), dq, J=10.0, 6.5 Hz), 2.27 (2H (2'), dt, J=7.4, 3.7 Hz), 1.29 (2H (4'), m, J=7.5, 7.2, 3.9 Hz), 1.29 (2H (5'), m, J=7.5, 7.2, 3.9 Hz), 2.36 (1H (2"), sxt, J=7.0 Hz), 3.14 (1H (8), d, J=6.6 Hz), 3.25 (1H (7), s), 3.64 (1H, (OH), s), 3.83 (1H (OH), dd, J=12.5, 7.9 Hz), 3.79 (2H (20), dd, J=12.5, 5.7 Hz), 3.94, (1H (OH), d, J=2.5 Hz), 4.06 (1H (10), t, J=2.6 Hz), 4.22 (1H (5), s), 5.37 (1H (12), d, J=10.0 Hz), 5.95 (1H (OH), br.s.) 7.7 (1H (1), dd, J=2.4, 1.3 Hz).

¹³C NMR (125 MHz, CDCl₃) δ ppm: 9.7 (19), 11.6 (4"), 13.9 (6'), 15.0 (18), 16.1 (5"), 17.1 (16), 22.3 (5'), 23.6 (17), 24.9 (3'), 26.2 (3"), 26.6 (15), 31.1 (4'), 34.5 (2'), 35.96 (8), 36.04 (14), 41.2 (2"), 45.6 (11), 48.9 (10), 61.8 (6), 64.6 (20), 65.2 (7), 65.5 (13), 71.4 (5), 72.4 (4), 76.5 (12), 77.1 (9), 133.4 (2), 164.6 (1), 173.3 (1'), 178.8 (1"), 209.9 (3),

Compound 6: 12-acetyl-13-(2-methylbutanoyl)-6,7-epoxy-4,5,9,12,13,20-hexahydroxy-1-tigliaen-3-one

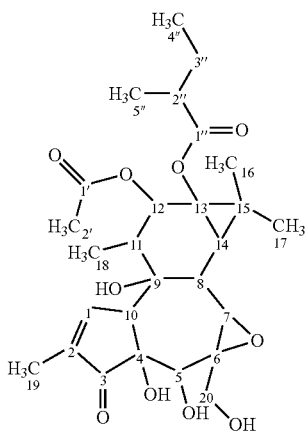

¹H NMR (500 MHz, CDCl₃) δ ppm: 0.85 (3H (18), d, J=6.4 Hz), 0.92 (3H (4"), t, J=7.6 Hz), 1.12 (3H (5"), d, J=6.8 Hz), 1.21 (3H (16), s), 1.23 (3H (17), s), 1.25 (1H (14), d, J=6.8 Hz), 1.44 (1H (3"), m, J=14.1, 7.3, 7.2 Hz), 1.71 (1H (3"), dd), 1.75 (3H (19), dd, J=2.9, 1.0 Hz), 1.91 (1H (11), m), 2.04 (3H (2'), s), 2.36 (1H (2"), m, J=7.0, 6.8 Hz), 3.14 (1H (8), d, J=6.8 Hz), 3.26 (1H (7), s), 3.78 (1H (20), d, J=12.7 Hz), 3.85 (1H (20), d, J=12.7 Hz), 4.04 (1H (10), t, J=2.7 Hz), 4.21 (1H (5), s), 5.33 (1H (12), d, J=9.8 Hz), 7.7 (1H (1), s).

¹³C NMR (125 MHz, CDCl₃) δ ppm: 9.7 (19), 11.6 (4"), 15.1 (18), 16.2 (5"), 17.1 (16), 21.0 (2'), 23.7 (17), 26.2 (3"), 26.7 (15), 36.0 (8), 36.1 (14), 41.2 (2"), 45.7 (11), 48.9 (10), 61.7 (6), 64.5 (20), 65.2 (7), 65.4 (13), 71.5 (5), 72.4 (4), 76.8 (9), 77.1 (12), 133.5 (2), 164.6 (1), 170.6 (1'), 178.9 (1"), 209.9 (3).

Compound 7: 12-propanoyl-13-(2-methylbutanoyl)-6,7-epoxy-4,5,9,12,13,20-hexahydroxy-1-tigliaen-3-one

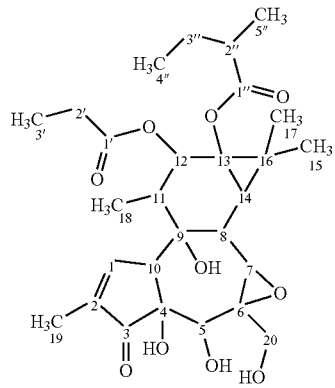

¹H NMR (500 MHz, CDCl₃) δ ppm: 0.85 (3H (18), d, J=6.8 Hz), 0.92 (3H (4"), t, J=7.6 Hz), 1.12 (3H (5"), d, J=7.3 Hz), 1.13 (3H (3'), t), 1.21 (3H (16), s), 1.22 (3H (17), s), 1.25 (1H (14), dd, J=10.3, 6.8 Hz), 1.44 (1H (3"), m J=14.0, 7.0, 6.6 Hz), 1.70 (1H (3"), dd, J=14.2, 6.8 Hz), 1.74 (3H (19), dd, J=2.9, 1.5 Hz), 1.91 (1H (11), m), 2.31 (2H (2'), m), 2.37 (1H (2"), dd, J=13.7, 6.8 Hz), 3.15 (1H (8), d, J=6.8 Hz), 3.26 (1H (7), s), 3.78 (1H (20), d, J=12.2 Hz), 3.84 (1H (20), d, J=12.7 Hz), 4.05 (1H (10), m), 4.21 (1H (5), s), 5.35 (1H (12), d, J=9.8 Hz), 5.92 (1H (OH), br.s.), 7.71 (1H (1), m).

¹³C NMR (125 MHz, CDCl₃) δ ppm: 9.3 (3'), 9.7 (19), 11.6 (4"), 15.1 (18), 16.1 (5"), 17.1 (16), 23.7 (17), 26.2 (3"), 26.7 (15), 27.8 (2'), 36.0 (8), 36.1 (14), 41.2 (2"), 45.7 (11), 48.9 (10), 61.7 (6), 64.6 (20), 65.2 (7), 65.4 (13), 71.5 (5), 72.4 (4), 76.8 (12), 77.1 (9), 133.5 (2), 164.6 (1), 173.9 (1'), 178.9 (1"), 209.9 (3).

Compound 8: 12-butanoyl-13-(2-methylbutanoyl)-6,7-epoxy-4,5,9,12,13,20-hexahydroxy-1-tigliaen-3-one

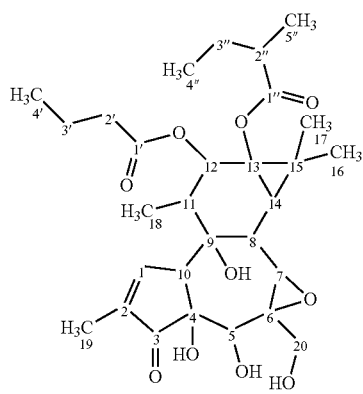

$^1$H NMR (500 MHz, CDCl$_3$) δ ppm: 0.85 (3H (18), d, J=6.4 Hz), 0.92 (3H (4"), t, J=7.6 Hz), 0.94 (3H (4'), t, J=7.3 Hz), 1.12 (3H (5"), d), 1.22 (3H (16), s), 1.23 (3H (17), s), 1.26 (1H (14), d, J=6.8 Hz), 1.45 (1H (3"), dq, J=14.0, 7.1 Hz) 1.64 (2H (3'), m, J=14.6, 7.2, 7.1 Hz), 1.71 (1H (3"), dd, J=13.7, 6.8 Hz), 1.75 (3H (19), d, J=2.9 Hz), 1.90 (1H (11), dd, J=10.0, 6.6 Hz), 2.27 (2H (2'), m), 2.37 (1H (2"), qt, J=7.0, 6.8 Hz), 3.1.5 (1H (8), d, J=6.4 Hz), 3.27 (1H (7), s), 3.77 (1H (20), m, J=12.2 Hz), 3.86 (1H (20), m, J=12.7 Hz), 4.05 (1H (10), d, J=2.4 Hz), 4.21 (1H (5), s), 7.71 (1H (1), dd, J=2.4, 1.0 Hz).

$^{13}$C NMR (125 MHz, CDCl$_3$) δ ppm: 9.7 (19), 11.6 (4"), 13.5 (4'), 15.1 (18), 16.1 (5"), 17.1 (16), 18.7 (3'), 23.7 (17), 26.2 (3"), 26.6 (15), 36.0 (8), 36.1 (14), 36.4 (2'), 41.2 (2"), 45.6. (11), 48.9 (10), 61.6 (6), 64.5 (20), 65.2 (7), 65.5 (13), 71.7 (5), 72.3 (4), 76.6 (12), 77.1 (9), 133.5 (2), 164.7 (1), 173.1 (1'), 178.8 (1"), 209.9 (3).

Compound 9: 12-[(2E,4E)-(6,6-dimethoxyhexa-2,4-dienoyl]-13-(2-methylbutanoyl)-6,7-epoxy-4,5,9,12,13,20-hexahydroxy-1-tigliaen-3-one

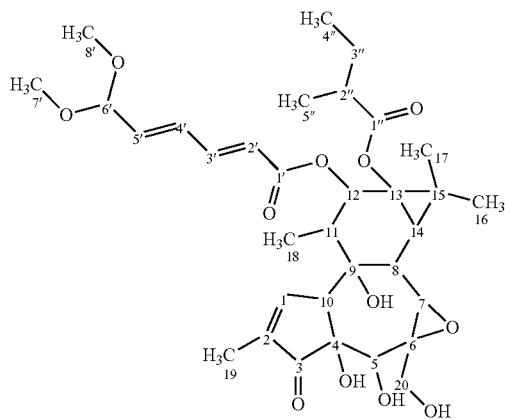

$^1$H NMR (500 MHz, CDCl$_3$) δ ppm: 0.86 (3H (18), d, J=6.4 Hz), 0.92 (3H (4"), t, J=7.3 Hz), 1.12 (3H (5"), d, J=6.8 Hz), 1.22 (3H (17), s), 1.24 (3H (16), s), 1.27 (1H (14), dd, J=11.2, 6.8 Hz), 1.44 (1H, (3"), m), 1.72 (1H (3"), m), 1.75 (3H (19), dd, J=2.9, 1.5 Hz), 1.96 (1H (11), dd, J=10.0, 6.6 Hz), 2.37 (1H (2"), m), 3.17 (1H (8), d, J=6.8 Hz), 3.27 (1H (7), s), 3.31 (3H (7'), s), 3.31 (3H (8'), s), 3.79, (1H (20), m, J=12.2 Hz), 3.86 (1H (20), m), 4.06 (1H (10), br.s.), 4.22 (1H (5), d, J=2.4 Hz), 4.89 (1H (6'), dd, J=4.4, 1.0 Hz), 5.42 (1H (12), d, J=9.8 Hz), 5.91 (1H (2'), d, J=15.7 Hz), 5.98 (1H (5'), dd, J=15.7, 4.4 Hz), 6.47 (1H (4'), dd, 15.6, 11.2 Hz), 7.21 (1H (3'), dd, J=15.6, 11.2 Hz), 7.71 (1H (1), s).

$^{13}$C NMR (125 MHz, CDCl$_3$) δ ppm: 9.7 (19), 11.6 (4"), 15.1 (18), 16.2 (5"), 17.2 (17), 23.6 (16), 26.2 (3"), 26.8 (15), 36.0 (8), 36.2 (14), 41.2 (2"), 45.8 (11), 48.9 (10), 52.7 (7'), 52.7 (8'), 61.7 (6), 64.5 (20), 65.2 (7), 65.4 (13), 71.6 (5), 72.4 (4), 77.1 (9), 77.1 (12), 101.3 (6'), 122.8 (2'), 131.0 (4'), 133.5 (2), 137.9 (5'), 143.4 (3'), 164.7 (1), 166.1 (1'), 178.9 (1"), 209.9 (3).

Compound 10: 12-[(2E,4E)-6-oxohexa-2,4-dienoyl]-13-(2-methylbutanoyl)-6,7-epoxy-4,5,9,12,13,20-hexahydroxy-1-tigliaen-3-one

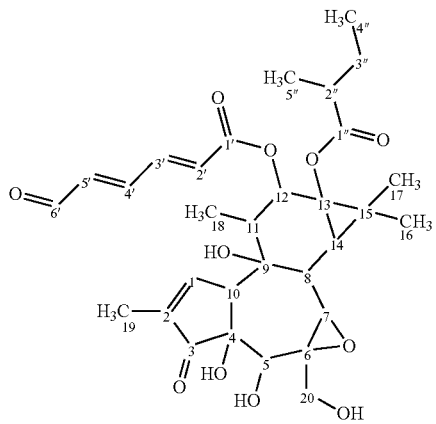

$^1$H NMR (500 MHz, CDCl$_3$) δ ppm: 0.88 (3H (18), d, J=6.4 Hz), 0.93 (3H (4"), t, J=7.5 Hz), 1.13 (3H (5"), d, J=7.1 Hz), 1.24 (3H (17), s), 1.25 (3H (16), s), 1.28 (1H (14), m), 1.46 (1H (3"), td, J=14.1, 7.3 Hz), 1.70 (1H (3"), m), 1.75 (3H (19), dd, J=2.9, 1.2 Hz), 1.99 (1H (11), dddd, J=9.8, 6.5, 6.4, 6.1 Hz), 2.38 (1H (2"), d, J=6.8 Hz), 3.19 (1H (8), d, J=6.8 Hz), 3.28 (1H (7), s), 3.77 (1H (20), m, J=12.5 Hz), 3.87 (1H (20), d, J=13.0 Hz), 4.06 (1H (10), d, J=2.7 Hz), 4.22 (1H (5), s), 5.46 (1H (12), d, J=9.8 Hz), 6.28 (1H (2'), d, J=15.4 Hz), 6.40 (1H (5'), dd, J=15.4, 7.8 Hz), 7.14 (1H (4'), dd, J=14.9, 11.2 Hz), 7.36 (1H (3"), dd, J=15.4, 11.2 Hz), 7.71 (1H (1), dd, J=2.6, 1.3 Hz), 9.66 (1H (6'), d, J=7.6 Hz).

$^{13}$C NMR (125 MHz, CDCl$_3$) δ ppm: 9.7 (19), 11.6 (4"), 15.2 (18), 16.2 (5"), 17.2 (16), 23.6 (17), 26.2 (3"), 26.9 (15), 36.0 (8), 36.3 (14), 41.2 (2"), 45.8 (11), 48.9 (10), 61.7 (6), 64.5 (20), 65.1 (7), 65.3 (13), 71.6 (5), 72.3 (4), 77.1 (9), 78.2 (12), 129.4 (2'), 133.6 (2), 137.2 (5'), 140.8 (3'), 146.9 (4'), 164.4 (1), 165.0 (1'), 178.9 (1"), 192.8 (6'), 209.9 (3).

Compound 11: 12-[(2E,4E)-6,7-dihydroxydodeca-2,4-dienoyl]-13-(2-methylbutanoyl)-6,7-epoxy-4,5,9,12,13,20-hexahydroxy-1-tigliaen-3-one

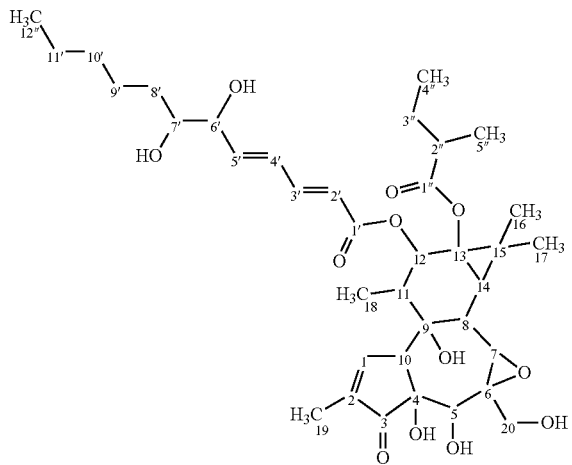

$^1$H NMR (500 MHz, CDCl$_3$) δ ppm: 0.87 (3H (18), d, J=2.0 Hz), 0.87 (3H (12'), d, J=2.0 Hz), 0.92 (3H (4"), t, J=7.3 Hz), 1.12 (3H (5"), d, J=6.8 Hz), 1.22 (3H (17), s), 1.24 (3H (16), s), 1.28 (1H (14), d, J=6.4 Hz), 1.28 (2H (11'), d, J=6.4 Hz), 1.44 (2H (8'), d, J=6.8 Hz), 1.46 (1H (3"), d, J=6.8 Hz), 1.47 (2H (9'), d, J=2.9 Hz), 1.69 (1H (3"), m), 1.76 (3H (19), m), 1.95 (1H (11), dd, J=9.5, 6.6 Hz), 2.38 (1H (2"), dq, J=13.7, 6.8 Hz), 3.17 (1H (8), d, J=6.4 Hz), 3.27 (1H (7), s), 3.49 (1H (7'), br.s.), 3.60 (1H (OH), s), 3.82 (2H (20),), 4.03 (1H (6'), m), 4.06 (1H (10), br.s.), 4.22 (1H (5), d, J=2.9 Hz), 5.42 (1H (12), d, J=9.8 Hz), 5.88 (1H (2'), d, J=15.2 Hz), 6.08 (1H (OH), t, J=6.1 Hz), 6.11 (1H (5'), t, J=6.1 Hz), 6.43 (1H (OH), m), 6.47 (1H (4'), m), 7.21 (1H (OH), dd, J=13.2, 2.0 Hz), 7.24 (1H (3'), s), 7.71 (1H (1), s),
$^{13}$C NMR (125 MHz, CDCl$_3$) δ ppm: 9.7 (19), 11.6 (4"), 14.0 (12'), 15.1 (18), 16.2 (5"), 17.2 (16), 22.6 (11'), 23.6 (17), 25.3 (9'), 26.2 (3"), 26.8 (15), 31.7 (10'), 33.1 (8'), 36.0 (8), 36.2 (14), 41.2 (2"), 45.8 (11), 48.9 (10), 61.7 (6), 64.5 (20), 65.2 (7), 65.4 (13), 71.6 (5), 72.4 (4), 74.5 (7), 75.1 (6'), 77.1 (9), 77.1 (12), 133.5 (2), 121.8 (2'), 129.7 (4'), 141.6 (5'), 143.8 (3'), 164.6 (1), 166.2 (1'), 178.9 (1"), 209.9 (3).

Compound 12: 12-[(2E)-4,5-dihydroxy-deca-2-enoyl]-13-(2-methylbutanoyl)-6,7-epoxy-4,5,9,12,13,20-hexahydroxy-1-tigliaen-3-one

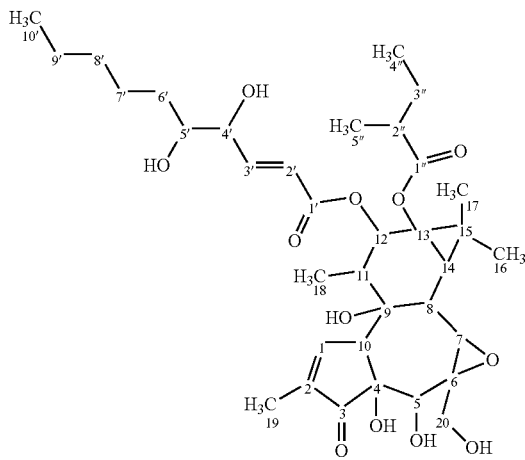

$^1$H NMR (500 MHz, CDCl$_3$) δ ppm: 0.86 (3H (18), d), 0.87 (3H (10'), t), 0.93 (3H (4"), t, J=7.5 Hz), 1.12 (3H (5"), d, J=7.0 Hz), 1.22 (3H (17), s), 1.23 (3H (16), s), 1.26 (2H (9'), m), 1.27 (1H (14), m), 1.28 (2H (8'), m), 1.30 (1H (7'), m), 1.42 (2H (6'), m), 1.44 (1H (3"), m), 1.46 (1H (7'), m), 1.70 (1H (3"), m), 1.74 (3H (19), d, J=1.6 Hz), 1.95 (1H (11), m), 2.37 (1H (2"), m), 3.16 (1H (8), d, J=6.5 Hz), 3.27 (1H (7), s), 3.75 (1H (5'), m), 3.77 (1H (20), m), 3.85 (1H (20), d, J=19.3 Hz), 4.05 (1H (10), br.s.), 4.21 (1H (5), s), 4.32 (1H (4'), m), 5.41 (1H (12), d, J=9.5 Hz), 6.11 (1H (2'), dd, J=8.8, 1.8 Hz), 6.92 (1H (3'), dd, J=4.9, 1.6 Hz), 7.71 (1H (1), dd).
$^{13}$C NMR (125 MHz, CDCl$_3$) δ ppm: 9.7 (19), 11.6 (4"), 14 (10'), 15.1 (18), 16.2 (5"), 17.2 (16), 22.5 (9'), 23.7 (17), 25.5 (7'), 26.2 (3"), 26.8 (15), 31.7 (8'), 32.0 (6'), 36.0 (8), 36.2 (14), 41.2 (2"), 45.8 (11), 48.9 (10), 61.7 (6), 64.5 (20), 65.2 (7), 65.4 (13), 71.6 (5), 72.3 (4), 73.9 (4'), 74.1 (5'), 77.1 (12), 77.3 (9), 122.5 (2'), 133.6 (2), 145.9 (3'), 164.6 (1), 165.5 (1'), 179 (1"), 209.9 (3).

Compound 13: 12-tigloyl-13-(2-methylpropanoyl)-6,7-epoxy-4,5,9,12,13,20-hexahydroxy-1-tigliaen-3-one

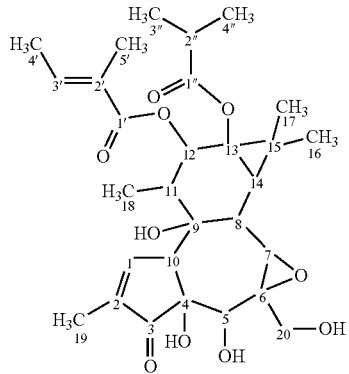

$^1$H NMR (500 MHz, CDCl$_3$) δ ppm: 0.84 (3H (18), d, J=6.4 Hz), 1.14 (3H (4") d, J=7.3 Hz), 1.17 (3H (3"), d, J=6.8 Hz), 1.22 (3H (16), s), 1.24 (3H (17), s), 1.28 (1H (8), m), 1.74 (3H (19), s), 1.77 (3H (4'), d, J=7.3 Hz), 1.95 (1H (11), dd, J=10.0, 6.6 Hz), 2.56 (1H, (2"), m, J=7.3, 7.1, 7.0 Hz), 3.16 (1H (14), d, J=6.4 Hz), 3.26 (1H (7), s), 3.82 (2H (20), m), 4.06 (1H (10), br.s.), 4.22 (1H (5), d, J=2.4 Hz), 5.41 (1H (12), d, J=9.8 Hz), 6.80 (1H (3'), m), 7.71 (1H (1), s).

$^{13}$C NMR (125 MHz, CDCl$_3$) δ ppm: 9.7 (19), 12.2 (5'), 14.4 (4'), 15.1 (18), 17.2 (17), 18.5 (3"), 18.6 (4"), 23.7 (16), 26.5 (15), 34.1 (2"), 36.0 (8), 36.1 (14), 45.8 (11), 48.9 (10), 61.7 (6), 64.6 (20), 65.2 (7), 65.5 (13), 71.4 (5), 72.4 (4), 76.6 (12), 77.2 (9), 128.4 (2'), 133.4 (2), 137.6 (3'), 164.7 (1), 167.5 (1'), 179.3 (1"), 209.9 (3).

Compound 14: 12-[(2E)-3-methylthioprop-2-enoyl]-13-(2-methylbutanoyl)-6,7-epoxy-4,5,9,12,13,20-hexahydroxy-1-tigliaen-3-one

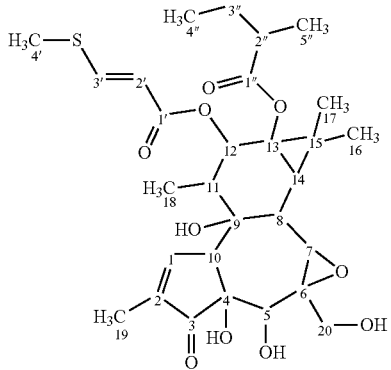

$^1$H NMR (500 MHz, CDCl$_3$) δ ppm: 0.86 (3H (18), d, J=6.4 Hz), 0.92 (3H (4″), t, J=7.3 Hz), 1.12 (3H (5″), d, J=6.8 Hz), 1.23 (3H (17), s), 1.24 (3H (16), s), 1.27 (1H (14), d, J=6.8 Hz), 1.44 (1H (3″), m), 1.71 (1H (3″), m), 1.75 (3H (19), s), 1.94 (1H (11), m), 2.14 (1H (OH), t, J=5.9 Hz), 2.32 (3H (4′), s), 2.38 (1H (2″), m), 3.16 (1H (8), d, J=6.8 Hz), 3.27 (1H (7), s), 3.55 (1H (4-OH), s), 3.78 (1H (20), dd, J=12.7, 5.9 Hz), 3.84 (1H (5-OH), s), 3.85 (1H (20), s), 4.05 (1H (10), m), 4.21 (1H (5), d, J=2.4 Hz), 5.41 (1H (12), d, J=9.8 Hz), 5.61 (1H (2′), d, J=14.7 Hz), 6.02 (1H (9-OH), m), 7.69 (1H (3′), d, J=14.7 Hz), 7.71 (1H (1), s).

$^{13}$C NMR (125 MHz, CDCl$_3$) δ ppm: 9.7 (19), 11.6 (4″), 14.3 (4′), 15.1 (18), 16.2 (5″), 17.2 (16), 23.7 (17), 26.2 (3″), 26.7 (15), 36.1 (8), 36.2 (14), 41.2 (2″), 45.9 (11), 49.0 (10), 61.6 (6), 64.5 (20), 65.2 (7), 65.5 (13), 71.7 (5), 72.4 (4), 76.8 (12), 77.1 (9), 112.8 (2′), 133.5 (2), 147.5 (3′), 164.5 (1′), 164.8 (1), 178.9 (1″), 210.0 (3).

Compound 15: 12-(2-methylprop-2-enoyl-13-(2-methylbutanoyl)-6,7-epoxy-4,5,9,12,13,20-hexahydroxy-1-tigliaen-3-one

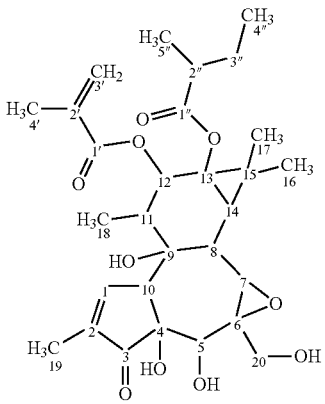

$^1$H NMR (500 MHz, CDCl$_3$) δ ppm: 0.86 (3H (18), d), 0.92 (3H (4″), t, J=7.3 Hz), 1.12 (3H (5″), d, J=6.8 Hz), 1.23 (3H (17), br.s.), 1.25 (3H (16), s), 1.27 (1H (14), dd, J=11.2, 6.4 Hz), 1.45 (1H (3″), m), 1.72 (1H (3″), m), 1.75 (3H (19), dd, J=2.9, 1.0 Hz), 1.92 (3H (4′), s), 1.95 (1H (11), m), 2.38 (1H (2″), m), 3.18 (1H (8), d), 3.28 (1H (7), s), 3.54 (1H (OH), d, J=1.0 Hz), 3.78 (1H (20), m), 3.87 (1H (20), dd), 4.06 (1H (10), m), 4.22 (1H (5), d, J=2.0 Hz), 5.42 (1H (12), s), 5.56 (1H (3′), dt, J=2.9, 1.5 Hz), 6.05 (1H (3′), m), 7.72 (1H (1), dd, J=2.4, 1.5 Hz).

$^{13}$C NMR (125 MHz, CDCl$_3$) δ ppm: 9.7 (19), 11.6 (4″), 15.1 (18), 16.2 (5″), 17.2 (17), 18.5 (4′), 23.7 (16), 26.2 (3″), 26.7 (15), 36.1 (8), 36.2 (14), 41.2 (2″), 45.9 (11), 49.0 (10), 61.6 (6), 64.5 (20), 65.2 (7), 65.5 (13), 71.7 (5), 72.3 (4), 77.1 (9), 77.3 (12), 125.8 (3′), 133.5 (2), 136.2 (2′), 164.7 (1), 166.8 (1′), 178.9 (1″), 209.9 (3),

Compound 16: 12-[(2E,4E)-hexa-2,4-dienoyl]-13-(2-methylbutanoyl)-6,7-epoxy-4,5,9,12,13,20-hexahydroxy-1-tigliaen-3-one

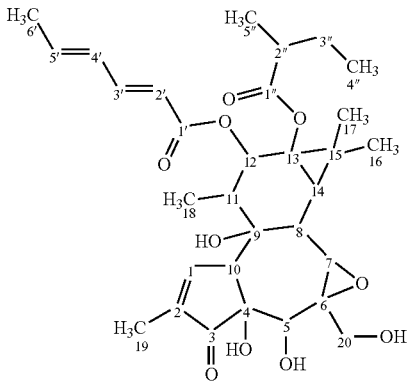

$^1$H NMR (500 MHz, CDCl$_3$) δ ppm: 0.87 (3H (18), d, J=6.5 Hz), 0.93 (3H (4″), t), 1.13 (3H (5″), m, J=6.8 Hz), 1.23 (3H (16), br.s.), 1.26 (3H (17), s), 1.27 (1H (14), m), 1.45 (1H (3″), s), 1.70 (1H (3″), m), 1.75 (3H (19), dd, J=2.8, 1.2 Hz), 1.86 (3H (6′), dd, J=7.3, 1.7 Hz), 1.96 (1H (11), dd, J=9.8, 6.2 Hz), 2.37 (1H (2″), m), 3.18 (1H (8), d, J=6.7 Hz), 3.28 (1H (7), s), 3.78 (1H (20), m), 3.87 (1H (20), m), 4.06 (1H (10), br.s.), 4.21 (1H (5), br.s.), 5.44 (1H (12), d, J=10.1 Hz), 5.83 (1H (2′), d, J=15.0 Hz), 5.94 (1H (5′), m), 6.14 (1H (4′), m), 7.59 (1H (3′), ddd, J=15.3, 11.7, 1.2 Hz), 7.72 (1H (1), dd, J=2.2, 1.3 Hz).

$^{13}$C NMR (125 MHz, CDCl$_3$) δ ppm: 9.7 (19), 11.6 (4″), 14.1 (6′), 15.2 (18), 16.2 (5″), 17.2 (17), 23.7 (16), 26.2 (3″), 26.7 (15), 36.1 (8), 36.2 (14), 41.2 (2″), 45.9 (11), 49.0 (10), 61.6 (6), 64.5 (20), 65.3 (7), 65.5 (13), 71.7 (5), 72.4 (4), 76.8 (12), 77.1 (9), 120.7 (2′), 127.3 (4′), 133.5 (2), 136.2 (5′), 139.6 (3′), 164.8 (1), 166.6 (1′), 179.0 (1″), 210.0 (3).

Compound 17: 12-[(2E,4E)-8-oxododeca-2,4-dienoyl]-13-(2-methylbutanoyl)-6,7-epoxy-4,5,9,12,13,20-hexahydroxy-1-tigliaen-3-one

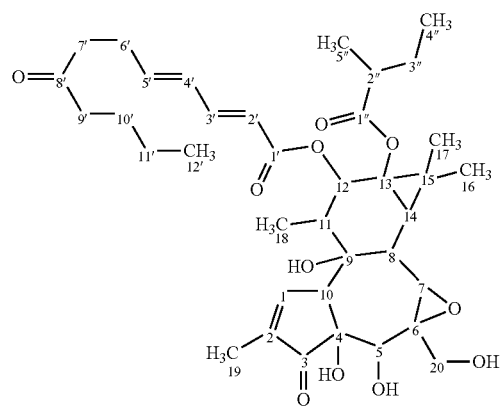

¹H NMR (500 MHz, CDCl₃) δ ppm: 0.85 (3H (18), d, J=5.3 Hz), 0.88 (3H (12'), t, J=7.3 Hz), 0.92 (3H (4"), t, J=7.4 Hz), 1.12 (3H (5"), d, J=7.0 Hz), 1.22 (3H (16), br.s.), 1.23 (3H (17), s), 1.26 (1H (14), d, J=5.4 Hz), 1.28 (2H (11'), d, J=2.8 Hz), 1.43 (1H (3"), br.s.), 1.53 (2H (10'), m), 1.71 (1H (3"), m), 1.75 (3H (19), dd, J=2.9, 1.3 Hz), 1.95 (1H (11), m), 2.37 (1H (2"), m), 2.38 (2H (9'), d, J=7.2 Hz), 2.42 (2H (6'), m), 2.52 (2H (7'), s), 3.17 (1H (8), d, J=6.6 Hz), 3.27 (1H (7), s), 3.53 (1H (OH), s), 3.81 (1H (20), br.s.), 3.86 (1H (20), m), 4.05 (1H (10), m), 4.22 (1H (5), d, J=2.4 Hz), 5.41 (1H (12), d, J=9.8 Hz), 5.76 (1H (2'), d, J=15.4 Hz), 6.09 (1H (5'), t, J=6.8 Hz), 6.15, (1H (4'), d, J=10.6 Hz), 7.16 (1H (3'), dd, J=15.4, 10.6 Hz), 7.71 (1H (1), dd, J=2.6, 1.3 Hz).

¹³C NMR (125 MHz, CDCl₃) δ ppm: 9.7 (19), 11.6 (4"), 13.8 (12'), 15.1 (18), 16.2 (5"), 17.2 (17), 22.3 (11'), 23.7 (16), 25.9 (10'), 26.2 (3"), 26.7 (15), 26.9 (6'), 36.1 (8), 36.1 (14), 41.2 (2"), 41.3 (7'), 42.7 (9'), 45.9 (11), 49.0 (10), 61.6 (6), 64.5 (20), 65.3 (7), 65.5 (13), 71.7 (5), 72.3 (4), 77.1 (12), 77.2 (9), 119.6 (2'), 129.1 (4'), 133.5 (2), 142.8 (5'), 145.0 (3'), 164.8 (1), 166.6 (1'), 179.0 (1"), 209.7 (8'), 210.1 (3).

Compound 18: 12-[(2Z,4E)-deca-2,4-dienoyl]-13-(2-methylbutanoyl)-6,7-epoxy-4,5,9,12,13,20-hexahydroxy-1-tigliaen-3-one

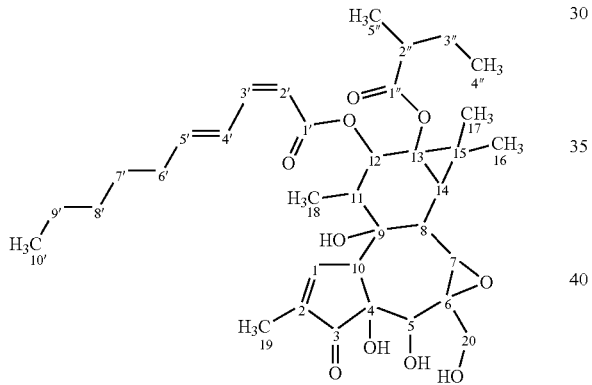

¹H NMR (500 MHz, CDCl₃) δ ppm: 0.86 (3H (10'), t, J=6.9 Hz), 0.87 (3H (18), d, J=6.6 Hz), 0.94 (3H (4"), t, J=7.5 Hz), 1.14 (3H (5"), d, J=7.1 Hz), 1.22 (3H (16), s), 1.23 (3H (17), s), 1.25 (1H (14), br.s.), 1.27 (2H (8'), br.s.), 1.28 (2H, (9'), br.s.), 1.41 (2H (7'), m), 1.46 (1H (3"), m), 1.71 (1H (3"), m), 1.75 (3H (19), dd, J=2.9, 1.3 Hz), 1.94 (1H (11), dd, J=10.0, 6.4 Hz), 2.16 (2H (6'), s), 2.39 (1H (2"), m, J=7.2, 7.0 Hz), 3.16 (1H (8), d, J=6.8 Hz), 3.27 (1H (7), s), 3.53 (1H (4-OH), d, J=0.6 Hz), 3.77 (1H (20), dd, J=12.7, 5.7 Hz), 3.83 (1H (5-OH), d, J=3.1 Hz), 3.86 (1H (20), m, J=12.6, 7.7 Hz), 4.05 (1H (10), t, J=2.7 Hz), 4.21 (1H (5), d, J=2.9 Hz), 5.43 (1H (12), d, J=9.9 Hz), 5.51 (1H (2'), d, J=11.4 Hz), 6.06 (1H (5'), ddd, J=15.1, 7.2, 6.8 Hz), 6.55 (1H (3'), t, J=11.6 Hz), 7.29 (1H (4'), ddd, J=15.1, 7.2, 6.8 Hz), 7.72 (1H (1), dd, J=2.3, 1.3 Hz).

¹³C NMR (125 MHz, CDCl₃) δ ppm: 9.7 (19), 11.6 (4"), 14.0 (10'), 15.1 (18), 16.2 (5"), 17.1 (16), 22.5 (9'), 23.7 (17), 26.2 (3"), 26.6 (15), 28.3 (7'), 31.4 (8'), 33.0 (6'), 36.0 (14), 36.1 (8), 41.2 (2"), 45.8 (11), 49.0 (10), 61.6 (6), 64.5 (20), 65.3 (7), 65.5 (13), 71.7 (5), 72.3 (4), 76.1 (12), 77.1 (9), 115.0 (2'), 126.9 (4'), 145.9 (3'), 146.1 (5'), 133.5 (2), 164.8 (1), 165.9 (1'), 178.9 (1"), 210.0 (3).

Compound 19: 13-(2-methylbutanoyl)-6,7-epoxy-4,5,9,12,13,20-hexahydroxy-1-tigliaen-3-one

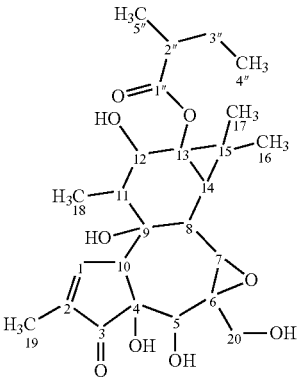

¹H NMR (500 MHz, CDCl₃) δ ppm: 0.92 (3H (4'), t, J=7.6 Hz), 1.07 (3H (18), d, J=6.4 Hz), 1.16 (3H (5'), d, J=6.8 Hz), 1.20 (3H (16), s), 1.24 (1H (14), m), 1.26 (3H (17), s), 1.45 (1H (3'), ddd, J=13.8, 7.1, 7.0 Hz), 1.71 (1H (3'), dt, J=13.7, 7.3 Hz), 1.76 (1H (11), d, J=15.7 Hz), 1.77 (3H (19), dd, J=2.7, 1.2 Hz), 2.41 (1H (2'), m, J=7.0, 6.8 Hz), 3.08 (1H (8), d, J=7.3 Hz), 3.27 (1H (7), s), 3.79 (1H (10), d, J=2.9 Hz), 3.81 (2H (20), m), 3.90 (1H (12), d, J=9.8 Hz), 4.20 (1H (5), s), 7.70 (1H (1), dd, J=2.4, 1.5 Hz).

¹³C NMR (125 MHz, CDCl₃) δ ppm: 9.8 (19), 11.7 (4'), 16.6 (5'), 16.2 (18), 17.2 (17), 23.4 (16), 26.5 (3'), 27.9 (15), 34.8 (14), 36.5 (8), 41.0 (2'), 47.3 (11), 50.7 (10), 62.4 (6), 65.0 (20), 66.0 (7), 68.4 (13), 71.5 (5), 72.1 (4), 77.6 (9), 78.3 (12), 133.9 (2), 163.8 (1), 180.1 (1'), 209.7 (3).

Compound 20: 12-[(2E)-but-2-enoyl]-13-(2-methylbutanoyl)-6,7-epoxy-4,5,9,12,13,20-hexahydroxy-1-tigliaen-3-one

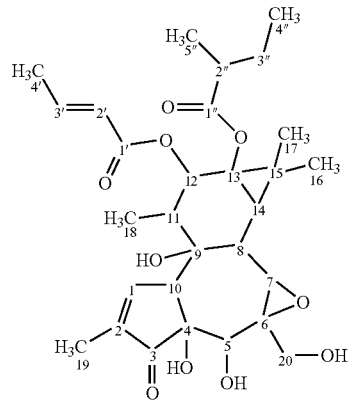

¹H NMR (500 MHz, CDCl₃) δ ppm: 0.85 (3H, (18), d, J=6.4 Hz), 0.92 (3H (4"), t, J=7.5 Hz), 1.12 (3H (5"), d, J=7.1 Hz), 1.22 (3H (17), s), 1.24 (3H (16), s), 1.26 (1H (14), d, J=6.7 Hz), 1.45 (1H (3"), dd, J=14.5, 6.4 Hz), 1.72 (1H (3"), dd, J=14.1, 6.8 Hz), 1.75 (3H (19), dd, J=2.8, 1.3 Hz), 1.87 (3H (4'), dd, J=6.9, 1.7 Hz), 1.94 (1H (11), dd, J=9.8, 6.4 Hz), 2.37 (1H (2"), dd, J=13.8, 6.8 Hz), 3.16 (1H (8), d, J=6.5 Hz), 3.27 (1H (7), s), 3.78 (1H (20), d, J=12.2 Hz), 3.87 (1H (20), m), 4.05 (1H (10), m), 4.21 (1H (5), s), 5.40

(1H (12), d, J=9.9 Hz), 5.81 (1H (2'), dddd, J=15.5, 1.6, 1.5, 1.2 Hz), 6.92 (1H (3'), dd, J=15.5, 7.0 Hz), 7.71 (1H (1), m).

<sup>13</sup>C NMR (125 MHz, CDCl<sub>3</sub>) δ ppm: 9.7 (19), 11.6 (4"), 15.1 (18), 16.2 (5"), 17.2 (17), 18.1 (4'), 23.7 (16), 26.2 (3"), 26.7 (15), 36.1 (8), 36.2 (14), 41.2 (2"), 45.9 (11), 49.0 (10), 61.6 (6), 64.5 (20), 65.3 (7), 65.5 (13), 71.7 (5), 72.3 (4), 76.7 (12), 77.1 (9), 122.6 (2'), 133.6 (2), 145.0 (3'), 164.8 (1), 166.1 (1'), 178.9 (1"), 210.2 (3).

Compound 24: 12-[(2E,4E)-deca-2,4-dienoyl]-13-(2-methylbutanoyl)-6,7-epoxy-4,5,9,12,13,20-hexahydroxy-1-tigliaen-3-one

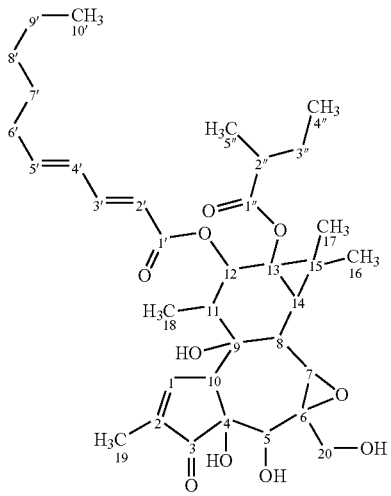

<sup>1</sup>H NMR (500 MHz, CDCl<sub>3</sub>) δ ppm: 0.86 (3H (18), d, J=5.6 Hz), 0.87 (3H (10'), d J=11.7 Hz), 0.93 (3H (4"), t, J=7.5 Hz), 1.12 (3H (5"), d, J=7.0 Hz), 1.22 (3H (16), s), 1.24 (3H (17), s), 1.26 (1H (14), m), 1.26 (2H (8'), br.s.), 1.29 (2H (9'), m), 1.45 (1H (3"), m), 1.41 (2H (7'), m), 1.73 (1H (3"), m), 1.75 (3H (19), dd, J=2.9, 1.3 Hz), 1.95 (1H (11), dd, J=9.7, 6.4 Hz), 2.15 (2H (6'), m), 2.38 (1H (2"), m), 3.17 (1H (8), d, J=6.6 Hz), 3.27 (1H (7), s), 3.55 (1H (OH), m), 3.78 (1H (20), dd, J=12.0, 4.6 Hz), 3.87 (1H (20), m), 4.05 (1H (10), m), 4.22 (1H (5), m), 5.41 (1H (12), d, J=9.9 Hz), 5.75 (1H (2'), d, J=15.4 Hz), 6.13 (1H (5'), dd, J=6.7, 6.2 Hz), 6.16 (1H (4'), s), 7.20 (1H (3'), dd, J=15.5, 9.9 Hz), 7.72 (1H (1), dt, J=2.5, 1.3 Hz).

<sup>13</sup>C NMR (125 MHz, CDCl<sub>3</sub>) δ ppm: 9.7 (19), 11.6 (4"), 14.0 (10'), 15.1 (18), 16.2 (5"), 17.2 (17), 22.4 (9'), 23.6 (16), 26.2 (3"), 26.7 (15), 28.4 (7'), 31.3 (8'), 33.0 (6'), 36.1 (8), 36.2 (14), 41.2 (2"), 45.9 (11), 49.0 (10), 61.6 (6), 64.5 (20), 65.3 (7), 65.5 (13), 71.7 (5), 72.3 (4), 76.7 (12), 77.1 (9), 118.8 (2'), 128.3 (4'), 133.5 (2), 145.3 (5'), 145.6 (3'), 164.8 (1), 166.6 (1'), 178.9 (1"), 210.0 (3).

Compound 25: 12-[(2Z,4E)-deca-2,4-dienoyl]-13-(2-methylpropanoyl)-6,7-epoxy-4,5,9,12,13,20-hexahydroxy-1-tigliaen-3-one

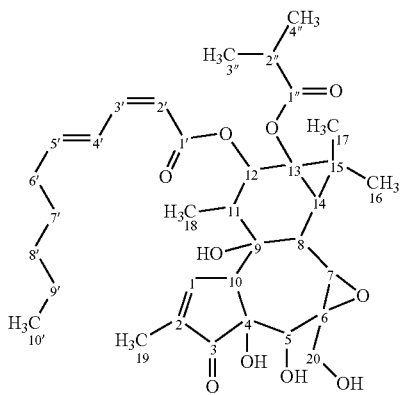

<sup>1</sup>H NMR (500 MHz, CDCl<sub>3</sub>) δ ppm: 0.85 (3H (18), d), 0.86 (3H (10'), t), 1.16 (3H (4"), d), 1.19 (3H (3"), d, J=7.0 Hz), 1.22 (3H (16), s), 1.22 (3H (17), s), 1.25 (2H (8'), m), 1.27 (1H (14), d, J=3.1 Hz), 1.29 (2H (9'), m), 1.41 (2H (7'), br.s.), 1.75 (3H (19), dd, J=1.3 Hz), 1.94 (1H (11), dd, J=10.0, 6.4 Hz), 2.16 (2H (6'), s), 2.58 (1H (2"), dt, J=14.0, 7.0 Hz), 3.16 (1H (8), d, J=6.7 Hz), 3.27 (1H (7), s), 3.55 (1H (OH), br.s), 3.78 (1H (20), d, J=12.5 Hz), 3.86 (1H (20), d, J=13.1 Hz), 4.05 (1H (10), d, J=5.4 Hz), 4.21 (1H (5), s), 5.41 (1H (12), d, J=9.9 Hz), 5.51 (1H (2'), d, J=11.2 Hz), 6.06 (1H (5'), dd, J=15.3, 7.0 Hz), 6.55 (1H (3'), t, J=11.4 Hz), 7.29 (1H (4'), dd, J=15.3, 7.0 Hz), 7.71 (1H (1), s).

<sup>13</sup>C NMR (125 MHz, CDCl<sub>3</sub>) δ ppm: 9.7 (19), 14.7 (10'), 15.1 (18), 17.1 (16), 18.6 (3"), 18.6 (4"), 22.5 (9'), 23.7 (17), 26.6 (15), 28.4 (7'), 31.4 (8'), 33.0 (6'), 34.2 (2"), 36.0 (14), 36.1 (8), 45.7 (11), 49.0 (10), 61.6 (6), 64.5 (20), 65.3 (7), 65.5 (13), 71.7 (5), 72.3 (4), 76.0 (12), 77.2 (9), 115.0 (2'), 126.9 (4'), 133.5 (2), 145.9 (3'), 146.2 (5'), 164.8 (1), 165.9 (1'), 179.3 (1"), 210.0 (3).

Compound 26: 12-[(2E,4E)-6,7-(anti)-epoxy-dodeca-2,4-dienoyl]-13-(2-methylbutanoyl)-6,7-epoxy-4,5,9,12,13,20-hexahydroxy-1-tigliaen-3-one

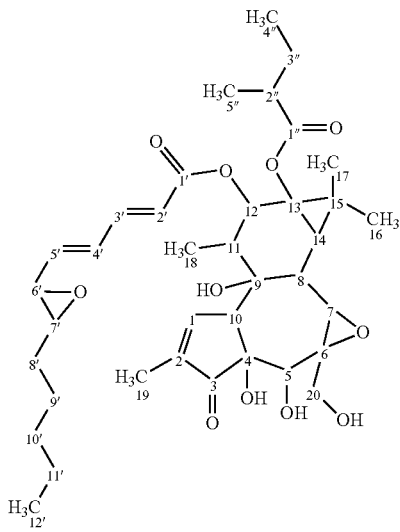

¹H NMR (500 MHz, CDCl₃) δ ppm: 0.87 (3H (18), d, J=4.4 Hz), 0.86 (3H (12'), br.s.), 0.92 (3H (4"), t, J=7.3 Hz), 1.12 (3H (5"), d, J=6.8 Hz), 1.22 (3H (17), br.s.), 1.24 (3H (16), s), 1.27 (1H (14), d, J=7.3 Hz), 1.28 (2H (11'), m), 1.29 (2H (10'), m), 1.44 (2H (9'), m), 1.57 (2H (8'), m), 1.72 (2H (3"), dd, J=13.9, 7.1 Hz), 1.75 (3H (19), d, J=1.5 Hz), 1.95 (1H (11), m), 2.37 (1H (2")·, m), 2.85 (1H (7"), tt, J=5.6, 2.0 Hz), 3.15 (1H (6'), d, J=7.8 Hz), 3.17 (1H (8), s), 3.28 (1H (7), s), 3.52 (1H (OH), d, J=2.9 Hz), 3.76 (1H (OH), m), 3.79 (1H (20), d, J=2.9 Hz), 3.87 (1H (20), m), 4.05 (1H (10), d, J=2.0 Hz), 4.22 (1H (5), d), 5.42 (1H (12), d, J=10.3 Hz), 5.83 (1H (5'), d, J=15.2, 7.8 Hz), 5.87 (1H (2') J=15.7 Hz), 6.00 (1H (OH), m), 6.47 (1H (4'), dd, J=14.7, 11.2 Hz), 7.20 (1H (3'), dd, J=15.2, 11.2 Hz), 7.71 (1H (1), br.s.).

¹³C NMR (125 MHz, CDCl₃) δ ppm: 9.7 (19), 11.6 (4"), 14.0 (12'), 15.1 (18), 16.2 (5"), 17.2 (16), 22.5 (11'), 23.7 (17), 25.5 (9'), 26.2 (3"), 26.8 (15), 31.5 (10'), 31.9 (8'), 36.1 (8), 36.2 (14), 41.2 (2"), 45.9 (11), 49.0 (10), 57.5 (6'), 61.6 (7), 61.7 (6), 64.5 (20), 65.2 (7), 65.4 (13), 71.7 (5), 72.3 (4), 77.1 (9), 77.1 (12), 121.6 (2'), 130.9 (4') 133.5 (2), 139.7 (5'), 143.3 (3'), 164.7 (1), 166.2 (1'), 179.0 (1"), 210.1 (3).

Compound 29: 12-tigloyl-13-(2-methylbutanoyl)-5,6-epoxy-4,5,9,12,13,20-hexahydroxy-1-tigliaen-3-one

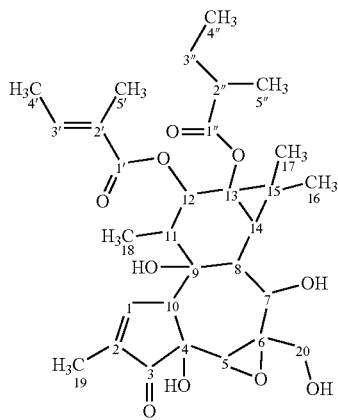

¹H NMR (500 MHz, CDCl₃) δ ppm: 0.83 (3H (18), d, J=6.8 Hz), 0.92 (3H (4"), t, J=7.6 Hz), 1.13 (3H (5"), d, J=6.8 Hz), 1.20 (1H (14), d, J=5.9 Hz), 1.22 (3H (17), s), 1.23 (3H (16), s), 1.45 (1H (3"), tt, J=14.2, 7.3 Hz), 1.72 (1H (3"), dd), 1.77 (3H (5'), dd, J=7.1, 1.2 Hz), 1.80 (3H (4'), d, J=1.5 Hz), 1.81 (3H (19), dd, J=2.9, 1.5 Hz), 2.11 (1H (11), dq), 2.29 (1H (8), d, J=5.4 Hz), 2.38 (1H (2"), m, J=7.0, 6.8 Hz), 2.47 (1H (20-OH), t, J=6.8 Hz), 2.98 (1H (4-OH), s), 3.53 (1H (10), m), 3.73 (1H (5), d, J=1.0 Hz), 3.81 (1H (20), dd, J=12.7, 6.8 Hz), 3.92 (1H (20), m, J=12.7, 6.8 Hz), 4.46 (1H (7), d, J=5.4 Hz), 5.10 (1H (7-OH), d, J=5.4 Hz), 5.39 (1H (12), d, J=10.3 Hz), 6.55 (1H (9-OH), m), 6.80 (1H (3'), m, J=7.1, 6.8, 1.5 Hz), 7.58 (1H (1), s), ¹³C NMR (125 MHz, CDCl₃) δ ppm: 10.3 (19), 11.6 (4"), 12.2 (4'), 14.0 (18), 14.4 (5'), 16.2 (5"), 17.0 (17), 23.5 (16), 26.2 (15), 26.2 (3"), 34.7 (14), 35.2 (8), 41.3 (2"), 43.7 (11), 57.3 (10), 62.6 (5), 64.2 (20), 67.0 (6), 67.0 (13), 71.3 (4), 75.8 (12), 77.3 (7), 79.1 (9), 128.3 (2'), 134.7 (2), 137.8 (3'), 159.7 (1), 167.4 (1'), 179.7 (1"), 205.7 (3).

Compound 30: 13-(2-methylbutanoyl)-5,6-epoxy-4,7,9,12,13,20-hexahydroxy-1-tigliaen-3-one

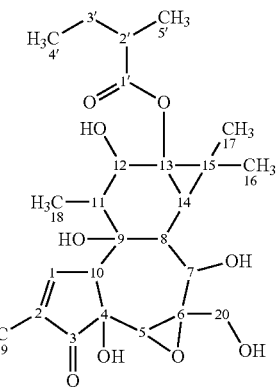

¹H NMR (500 MHz, CDCl₃) δ ppm: 0.91 (3H (4'), t, J=7.6 Hz), 1.02 (3H (18), d, J=6.4 Hz), 1.15 (1H (14), d, J=5.9 Hz), 1.15 (3H (5'), d, J=7.3 Hz), 1.19 (3H (16), s), 1.22 (3H (17), s), 1.46 (1H (3'), ddd, J=14.1, 7.0, 6.8 Hz), 1.70 (1H (3'), dt, J=13.7, 7.3 Hz), 1.81 (3H (19), dd, J=2.9, 1.5 Hz), 1.93 (1H (11), dq, J=9.8, 6.6, 6.5 Hz), 2.24 (1H (8), d, J=5.9 Hz), 2.40 (1H (2'), m, J=7.0, 6.8 Hz), 2.84 (1H (20-OH), br.s.), 3.44 (1H (4-OH), s), 3.50 (1H (10), t, J=2.4 Hz), 3.76 (1H (5), s), 3.84 (1H (20), dd, J=12.2, 3.9 Hz), 3.88 (1H (12), dd, J=10.0, 3.7 Hz), 3.92 (1H (20), d, J=12.2, 5.9 Hz), 4.46 (1H (7), d, J=4.4 Hz), 4.57 (1H (OH), m), 5.20 (1H (OH), m), 7.60 (1H (1), s).

¹³C NMR (125 MHz, CDCl₃) δ ppm: 10.3 (19), 11.7 (4'), 14.6 (18), 16.5 (5'), 16.7 (16), 23.6 (17), 26.4 (15), 26.5 (3'), 33.8 (14), 35.5 (8), 41.1 (2'), 45.5 (11), 57.8 (10), 62.6 (5), 64.1 (20), 66.9 (6), 68.0 (13), 71.3 (4), 76.8 (12), 77.3 (7), 78.8 (9), 134.4 (2), 160.2 (1), 180.0 (1'), 206.2 (3).

Compound 31: 12-acetyl-13-(2-methylbutanoyl)-5,6-epoxy-4,7,9,13,20-hexahydroxy-1-tigliaen-3-one

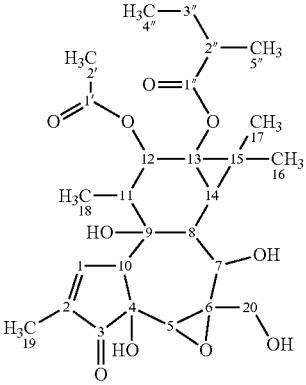

¹H NMR (500 MHz, CDCl₃) δ ppm: 0.84 (3H (18), d, J=6.6 Hz), 0.92 (3H (4"), t, J=7.5 Hz), 1.12 (3H (5"), d, J=7.0 Hz), 1.17 (3H (16), s), 1.18 (1H (14), s), 1.22 (3H (17), s), 1.44 (1H (3"), m, J=14.1, 7.3, 7.1 Hz), 1.81 (3H (19), dd, J=2.8, 1.2 Hz), 2.04 (3H (2'), s), 2.09 (1H (11), dq, J=10.2, 6.5 Hz), 2.31 (1H (8), d, J=5.6 Hz), 2.37 (1H (2"), sxt, J=7.0 Hz), 2.88 (1H (20-OH), m), 3.52 (1H (10), d, J=2.6 Hz), 3.59 (1H (4-OH), s), 3.81 (1H (5), d, J=0.9 Hz), 3.83 (1H (20), d, J=12.4 Hz), 3.96 (1H (20), d), 4.39 (1H (7), d, J=5.1 Hz), 5.04 (1H (7-OH), d, J=5.5 Hz), 5.3 (1H (12), d, J=10.1 Hz), 6.48 (1H (9-OH), br.s.), 7.58 (1H (1), s).

$^{13}$C NMR (125 MHz, CDCl$_3$) δ ppm: 10.3 (19), 11.6 (4″), 14.0 (18), 16.2 (5″), 16.7 (16), 20.9 (2′), 23.5 (17), 26.1 (3″), 26.2 (15), 34.6 (14), 35.1 (8), 41.3 (2″), 43.4 (11), 57.3 (10), 62.4 (5), 63.7 (20), 65.6 (13), 67.3 (6), 71.3 (4), 76.1 (12), 77.2 (7), 79.0 (9), 134.6 (2), 159.8 (1), 170.6 (1′), 179.7 (1″), 206.1 (3).

Compound 32: 12,13-di-(2-methylbutanoyl)-5,6-epoxy-4,7,9,13,20-hexahydroxy-1-tigliaen-3-one

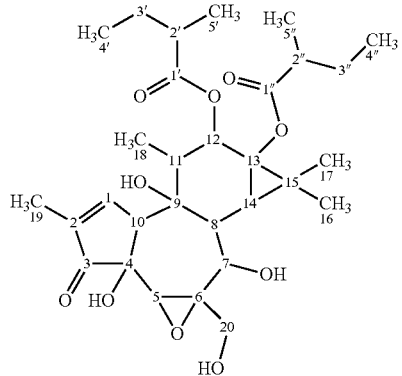

$^1$H NMR (500 MHz, CDCl$_3$) δ ppm: 0.84 (3H (18), d, J=6.6 Hz), 0.89 (3H (4′), m, J=7.6 Hz), 0.91 (3H (4″), d, J=7.5 Hz), 1.11 (3H (5″), d, J=7.0 Hz), 1.12 (3H (5′), d, J=7.0 Hz), 1.17 (3H (16), s), 1.18 (1H (14), d, J=5.7 Hz), 1.19 (3H (17), s), 1.42 (1H (3′), m), 1.46 (1H (3″), dt, J=6.8, 3.3 Hz), 1.62 (1H (3′), dt, J=8.2, 6.9 Hz), 1.68 (1H (3″), d, J=7.1 Hz), 1.80 (3H (19), dd, J=2.8, 1.3 Hz), 2.10 (1H (11), dd, J=10.2, 6. Hz), 2.33 (1H (8), d, J=5.4 Hz), 2.35 (1H (2′), m), 2.38 (1H (2″), d, J=4.3 Hz), 3.14 (1H (20-OH), br.s.), 3.54 (1H (10), dd, J=2.4, 2.2 Hz), 3.83 (1H (20), d, J=13.0 Hz), 3.85 (1H (5), d, J=1.0 Hz), 3.96 (1H (4-OH), s), 3.98 (1H (20), m, J=12.8 Hz), 4.37 (1H (7), d, J=5.3 Hz), 5.03 (1H (7-OH), d, J=5.5 Hz), 5.36 (1H (12), d, J=10.3 Hz), 6.46 (1H (9-OH), s), 7.59 (1H (1) s).

$^{13}$C NMR (125 MHz, CDCl$_3$) δ ppm: 10.3 (19), 11.6 (4″), 11.6 (4′), 13.9 (18), 16.1 (5″), 16.8 (5′), 16.9 (16), 23.5 (17), 26.0 (15), 26.2 (3″), 26.7 (3′), 34.6 (14), 35.1 (8), 41.3 (2″), 41.7 (2′), 43.3 (11), 57.2 (10), 62.5 (5), 63.2 (20), 65.6 (13), 67.6 (6), 71.3 (4), 75.4 (12), 77.2 (7), 79.1 (9), 134.6 (2), 160.0 (1), 175.9 (1′), 179.6 (1″), 206.3 (3).

Compound 33: 12-propanoyl-13-(2-methylbutanoyl)-5,6-epoxy-4,7,9,12,13,20-hexahydroxy-1-tigliaen-3-one

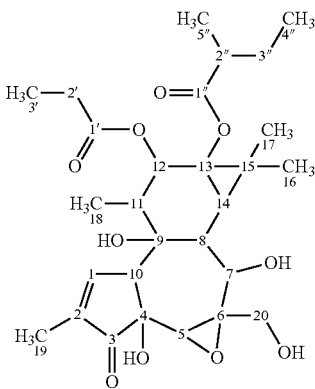

$^1$H NMR (500 MHz, CDCl$_3$) δ ppm: 0.83 (3H (18), d), 0.92 (3H (4″), t, J=7.5 Hz), 1.12 (3H (5″), d, J=7.0 Hz), 1.13 (3H (3′), t, J=7.6 Hz), 1.18 (3H (16), s), 1.19 (1H (14), s), 1.22 (3H (17), s), 1.44 (1H (3″), m, J=14.1, 7.5, 7.1 Hz), 1.71 (1H (3″), ddd, J=13.9, 7.3, 7.1 Hz), 1.81, (3H (19), dd, J=2.8, 1.3 Hz), 2.08 (1H (11), dd, J=10.2, 6.5 Hz), 2.29 (1H (8), m), 2.31 (2H (2′), m), 2.37 (1H (2″), d, J=7.0 Hz), 2.72 (1H (20-OH), t, J=6.7 Hz), 3.34 (1H (4-OH), s), 3.53 (1H (10), d, J=2.4 Hz), 3.78 (1H (5), d), 3.82 (1H (20), dd, J=12.7, 5.9 Hz), 3.94 (1H (20), dd, J=12.7, 5.9 Hz), 4.42 (1H (7), d, J=5.6 Hz), 5.06 (1H (7-OH), d, J=5.6 Hz), 5.32 (1H (12), d, J=10.3 Hz), 6.49 (1H (9-OH), s), 7.58 (1H (1), d, J=1.3 Hz).

$^{13}$C NMR (125 MHz, CDCl$_3$) δ ppm: 9.3 (3′), 10.3 (19), 11.6 (4″), 14.0 (18), 16.2 (5″), 16.8 (16), 23.5 (17), 26.1 (3″), 26.2 (15), 27.8 (2′), 34.6 (14), 35.1 (8), 41.3 (2″), 43.4 (11), 57.3 (10), 62.5 (5), 63.8 (20), 65.6 (13), 67.2 (6), 71.3 (4), 75.9 (12), 77.3 (7), 79.1 (9), 134.6 (2), 159.8 (1), 173.9 (1′), 179.7 (1″), 206.0 (3).

Compound 34: 12-hexanoyl-13-(2-methylbutanoyl)-5,6-epoxy-4,7,9,12,13,20-hexahydroxy-1-tigliaen-3-one

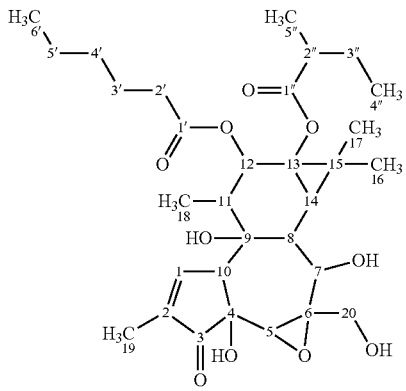

$^1$H NMR (500 MHz, CDCl$_3$) δ ppm: 0.83 (3H (18), d), 0.88 (3H (6′), t J=6.9 Hz), 0.92 (3H (4″), t, J=7.5 Hz), 1.12 (3H (5″), d, J=7.1 Hz), 1.18 (3H (16), s), 1.19 (1H (14), s), 1.21 (3H (17), s), 1.29 (2H (4′), m), 1.30 (2H (5′), m, J=7.6, 7.3, 3.6 Hz), 1.44 (1H, (3″), dt, J=14.1, 7.0 Hz), 1.61 (2H (3′), m), 1.70 (1H (3″), m, J=14.1, 7.3, 7.1 Hz), 1.81 (3H (19), dd, J=2.8, 1.3 Hz), 2.08 (1H (11), dq, J=10.3, 6.5 Hz), 2.3 (1H (8), d, J=3.8 Hz), 2.28 (2H (2′), m), 2.37 (1H (2″), q, J=7.0 Hz), 2.73 (1H (20-OH), m), 3.35 (1H (4-OH), br. s.), 3.53 (1H (10), t, J=2.5 Hz), 3.78 (1H (5), d, J=1.1 Hz), 3.82 (1H (20), d, J=12.6 Hz), 3.94 (1H (20), d, J=12.5 Hz), 4.42 (1H (7), d, J=3.9 Hz), 5.06 (1H (7-OH), d, J=5.4 Hz), 5.34 (1H (12), d, J=10.3 Hz), 6.48 (1H (9-OH), s), 7.58 (1H (1), d, J=1.5 Hz).

$^{13}$C NMR (125 MHz, CDCl$_3$) δ ppm: 10.3 (19), 11.6 (4″), 13.9 (18), 13.9 (6′), 16.1 (5″), 16.8 (16), 22.3 (5′), 23.5 (17), 24.9 (3″), 26.1 (15), 26.2 (3″), 31.1 (4′), 34.5 (2′), 34.6 (14), 35.2 (8), 41.3 (2″), 43.3 (11), 57.3 (10), 62.5 (5), 64.0 (20), 65.6 (13), 67.1 (6), 71.3 (4), 75.6 (12), 77.2 (7), 79.1 (9), 134.6 (2), 159.8 (1), 173.3 (1′), 179.6 (1″), 206.0 (3).

Compound 35: 12-tigloyl-13-(2-methylpropanoyl)-5,6-epoxy-4,7,9,12,13,20-hexahydroxy-1-tigliaen-3-one

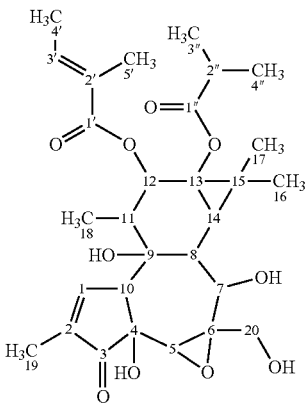

$^{1}$H NMR (500 MHz, CDCl$_3$) δ ppm: 0.84 (3H (18), d), 1.15 (3H (3''), d, J=7.0 Hz), 1.17 (3H (4''), d, J=7.0 Hz), 1.21 (1H (14), m), 1.21 (3H (16), s), 1.21 (3H (17), s), 1.77 (3H (4'), dd, J=7.1, 1.1 Hz), 1.80 (3H (5'), d, J=1.3 Hz), 1.81 (3H (19), dd, J=2.9, 1.4 Hz), 2.13 (1H (11), dd, J=9.6, 6.3 Hz), 2.32 (1H (8), d, J=6.1 Hz), 2.58 (1H (2''), spt, J=7.0 Hz), 3.46 (1H (4-OH), s), 3.54 (1H (10), d, J=2.5 Hz), 3.81 (1H (5), d, J=1.2 Hz), 3.82 (1H (20), m), 3.96 (1H (20), d, J=13.0 Hz), 4.42 (1H (7), d, J=4.9 Hz), 5.07 (1H (7-OH), d, J=5.5 Hz), 5.37 (1H (12), d, J=10.2 Hz), 6.52 (1H (9-OH), s), 6.80 (1H (3'), dq, J=7.0, 1.4 Hz), 7.58 (1H (1), dd, J=2.0, 1.4 Hz).

$^{13}$C NMR (125 MHz, CDCl$_3$) δ ppm: 10.3 (19), 12.2 (5'), 14.0 (18), 14.4 (4'), 16.9 (16), 18.5 (3''), 18.6 (4''), 23.5 (17), 26.0 (15), 34.2 (2''), 34.6 (14), 35.2 (8), 43.6 (11), 57.3 (10), 62.4 (5), 63.7 (20), 65.7 (13), 67.3 (6), 71.3 (4), 75.7 (12), 77.2 (7), 79.1 (9), 128.3 (2'), 134.6 (2), 137.8 (3'), 159.9 (1), 167.5 (1'), 180.1 (1''), 206.0 (3).

Compound 36: 12-[(2E)-3-methylthioprop-2-enoyl]-13-(2-methylbutanoyl)-5,6-epoxy-4,7,9,12,13,20-hexahydroxy-1-tigliaen-3-one

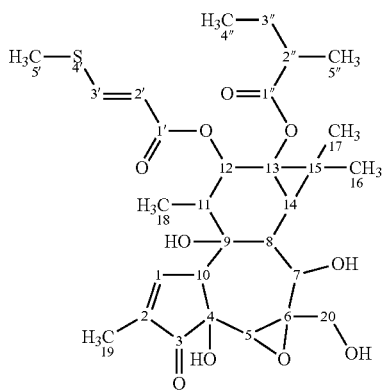

$^{1}$H NMR (500 MHz, CDCl$_3$) δ ppm: 0.92 (3H (4''), t, J=7.0 Hz), 0.84 (3H (18), d, J=6.5 Hz), 1.13 (3H (5'') d, J=7.0 Hz), 1.18 (1H (14), s), 1.20 (3H (16), s), 1.22 (3H (17), s), 1.44 (1H (3''), dt, J=13.9, 7.0 Hz), 1.72 (1H (3''), d, J=13.8 Hz), 1.81 (3H (19), dd, J=2.7, 1.2 Hz), 2.12 (1H (11), dd, J=9.4, 5.6 Hz), 2.31 (1H (8), d, J=6.0 Hz), 2.32 (3H (5'), s), 2.38 (1H (2''), q, J=7.0 Hz), 3.36 (1H (4-OH), s), 3.53 (1H (10), d, J=2.3 Hz), 3.78 (1H (5), d, J=0.9 Hz), 3.82 (1H (20), d, J=12.6 Hz), 3.94 (1H (20), d), 4.43 (1H (7), d, J=4.6 Hz), 5.08 (1H (7-OH), d), 5.37 (1H (12), d, J=10.2 Hz), 5.61 (1H (2'), d, J=14.9 Hz), 6.53 (1H (9-OH), s), 7.58 (1H (1), d, J=1.9 Hz), 7.68 (1H (3'), d, J=14.9 Hz).

$^{13}$C NMR (125 MHz, CDCl$_3$) δ ppm: 10.3 (19), 11.6 (4''), 14.0 (18), 14.3 (5'), 16.2 (5''), 16.9 (16), 23.5 (17), 26.2 (15), 26.2 (3''), 34.7 (14), 35.2 (8), 41.3 (2''), 43.6 (11), 57.3 (10), 62.5 (5), 64.0 (20), 65.6 (13), 67.1 (6), 71.3 (4), 75.8 (12), 77.3 (7), 79.1 (9), 112.7 (2'), 134.6 (2), 147.7 (3'), 159.8 (1), 164.5 (1'), 179.8 (1''), 206.0 (3).

Compound 37: 12-tigloyl-13-(2-methylbutanoyl)-5,6-epoxy-4,5,9,12,13,20-hexahydroxy-1-tigliaen-3-one

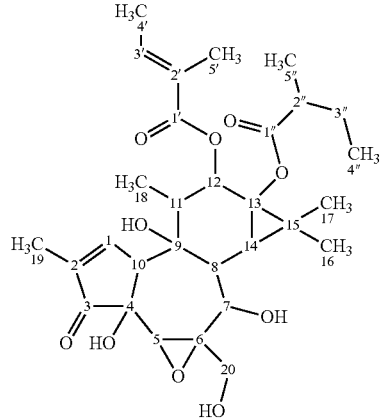

$^{1}$H NMR (500 MHz, CDCl$_3$) δ ppm: 0.84 (2H (18), d, J=6.6 Hz), 0.92 (3H (4''), t, J=7.5 Hz), 1.12 (3H (5''), d, J=6.9 Hz), 1.19 (1H (14), s), 1.20 (1H (16), s), 1.21 (1H (17), s), 1.44 (1H (3''), dt, J= 14.1, 7.0 Hz), 1.72 (1H (3''), dq), 1.77 (3H (4'), dd, J=7.1, 1.1 Hz), 1.8 (3H (5'), t, J=1.3 Hz), 1.81 (3H (19), dd, J=2.9, 1.5 Hz), 2.13 (1H (11), q, J=2.9 Hz), 2.33 (1H (8), d, J=5.7 Hz), 2.38 (1H (2''), q, J=7.0 Hz), 2.99 (1H (20-OH), br.s.), 3.55 (1H (10), t, J=2.6 Hz), 3.70 (1H (4-OH), br.s.), 3.83 (1H (20), dd, J=12.8, 4.9 Hz), 3.84 (1H (5), d, J=1.1 Hz), 3.98 (1H (20), dd, J=12.8, 7.3 Hz), 4.39 (1H (7), d, J=5.5 Hz), 5.06 (1H (7-OH), d, J=5.5 Hz), 5.39 (1H (12), d, J=10.2 Hz), 6.53 (1H (9-OH), br.s.), 6.8 (1H (3'), dd, J=7.1, 1.5 Hz), 7.59 (1H (1), dd, J=2.0, 1.5 Hz).

$^{13}$C NMR (125 MHz, CDCl$_3$) δ ppm: 10.3 (19), 11.6 (4''), 12.2 (5'), 14.0 (18), 14.4 (4'), 16.2 (5''), 17.0 (16), 23.5 (17), 26.1 (15), 26.1 (3''), 34.7 (14), 35.2 (8), 41.2 (2''), 43.7 (11), 57.2 (10), 62.3 (5), 63.5 (20), 65.7 (13), 67.5 (6), 71.3 (4), 75.9 (12), 77.2 (7), 79.1 (9), 128.3 (2'), 134.6 (2), 137.7 (3'), 159.9 (1), 167.4 (1'), 179.7 (1''), 206.1 (3).

Compound 38: 12,13-di-(2-methylbutanoyl)-5,6-epoxy-4,7,9,13,20-hexahydroxy-1-tigliaen-3-one

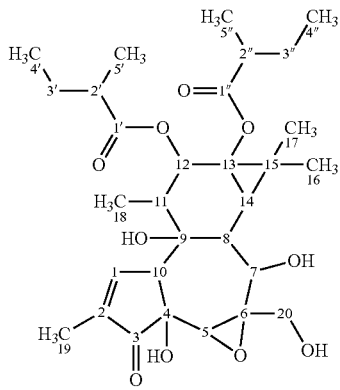

$^1$H NMR (500 MHz, CDCl$_3$) δ ppm: 0.84 (3H (18), d, J=6.6 Hz), 0.89 (3H (4'), t, J=7.4 Hz), 0.92 (3H (4"), t, J=7.5 Hz), 1.12 (3H (5'), d, J=7.0 Hz), 1.12 (3H (5"), d, J=7.0 Hz), 1.19 (1H (14), d, J=1.5 Hz), 1.20 (3H (16) s), 1.21 (3H (17), s), 1.45 (1H (3'), dd, J=14.1, 6.8 Hz), 1.45 (1H (3"), dd, J=14.1, 6.8 Hz), 1.62 (1H (3'), dd, J=8.3, 7.5 Hz), 1.68 (1H (3"), dd, J=14.1, 6.9 Hz), 1.81 (3H (19), dd, J=2.8, 1.3 Hz), 2.08 (1H (11), dd, J=10.3, 6.5 Hz), 2.30 (1H (8), d, J=5.5 Hz), 2.36 (1H (2'), m), 2.36 (1H (2"), m), 2.62 (1H (10-OH), t, J=6.8 Hz), 3.22 (1H (4-OH), s), 3.53 (1H (10), br.s.), 3.76 (1H (5), d, J=1.1 Hz), 3.82 (1H (20), dd, J=12.5, 6.3 Hz), 3.93 (1H (20), dd, J=12.6, 7.0 Hz), 4.44 (1H (7), d, J=5.5 Hz), 5.06 (1H (7-OH), d, J=5.6 Hz), 5.36 (1H (12), d, J=10.3 Hz). 6.48 (1H (9-OH), s), 7.58 (1H (1), d, J=2.0 Hz).

$^{13}$C NMR (125 MHz, CDCl$_3$) δ ppm: 10.3 (19), 11.6 (4'), 11.6 (4'), 13.9 (18), 16.1 (5"), 16.9 (5'), 17.0 (16), 23.5 (17), 26.0 (15), 26.2 (3"), 26.7 (3'), 34.6 (14), 35.2 (8), 41.3 (2'), 41.8 (2"), 43.3 (11), 57.3 (10), 62.5 (5), 63.9 (20), 65.6 (13), 67.2 (6), 71.3 (4), 75.4 (12), 77.3 (7), 79.1 (9), 134.7 (2), 159.8 (1), 175.9 (1'), 179.6 (1"), 205.9 (3).

Compound 39: 12-{[2-(methylsulfanyl)carbonyl]-acetoyl}-13-(2-methylbutanoyl)-5,6-epoxy-4,7,9,12,13,20-hexahydroxy-1-tigliaen-3-one

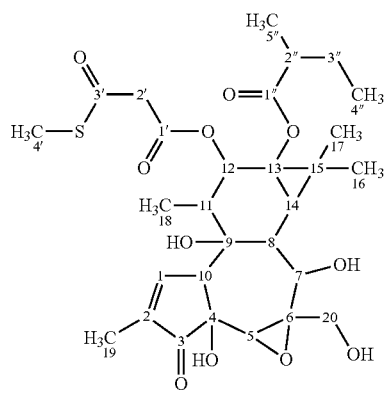

$^1$H NMR (500 MHz, CDCl$_3$) δ ppm: 0.87 (3H (18), d, J=6.6 Hz), 0.92 (3H (4"), t, J=7.5 Hz), 1.13 (3H (5"), d, J=7.0 Hz), 1.16 (3H (16), s), 1.20 (1H (14), d, J=5.9 Hz), 1.23 (17), br.s.), 1.45 (1H (3"), td, J=14.1, 7.2 Hz), 1.70 (1H (3"), td, J=14.0, 7.2 Hz), 1.82 (3H (19), dd, J=2.8, 1.3 Hz), 2.05 (1H (OH), d, J=3.40 Hz), 2.09 (1H (11), dd, J=10.3, 6.5 Hz), 2.27 (1H (8), d, J=5.9 Hz), 2.34 (3H (4'), s), 2.38 (1H (2"), t, J=7.0 Hz), 2.85 (1H (4-OH), s), 3.52 (1H (10), dd, J=2.6, 2.3 Hz), 3.57 (2H (2'), d, J=4.5 Hz), 3.70 (1H (5), d, J=1.1 Hz), 3.81 (1H (20), dd, J=12.2, 6.2 Hz), 3.89 (1H (20), m), 4.46 (1H (7), d, J=5.7 Hz), 5.02 (1H (7-OH), d, J=5.9 Hz), 5.35 (1H (12), d, J=10.3 Hz), 6.47 (1H (9-OH), m), 7.56 (1H (1), dd, J=2.0, 1.3 Hz).

$^{13}$C NMR (125 MHz, CDCl$_3$) δ ppm: 10.3 (19), 11.6 (4"), 12.1 (4'), 14.0 (18), 16.2 (5"), 16.6 (16), 23.5 (17), 26.2 (3"), 26.5 (15), 34.8 (14), 35.2 (8), 41.3 (2"), 43.3 (11), 49.5 (2'), 57.4 (10), 62.7 (5), 64.4 (20), 65.3 (13), 66.8 (6), 71.3 (4), 77.2 (7), 77.9 (12), 79.1 (9), 134.7 (2), 159.5 (1). 165.7 (1'), 179.8 (1"), 190.9 (3'), 205.6 (3).

Compound 40: 12-[(2-methoxycarbonyl)-acetoyl]-13-(2-methylbutanoyl)-5,6-epoxy-4,7,9,12,13,20-hexahydroxy-1-tigliaen-3-one

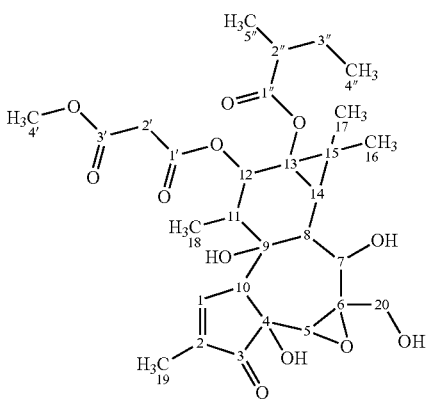

$^1$H NMR (500 MHz, CDCl$_3$) δ ppm: 0.88 (3H (18), d), 0.92 (3H (4"), t, J=7.6 Hz), 1.13 (3H (5"), d, J=6.8 Hz), 1.17 (3H (16), s), 1.21 (1H (14), d, J=5.9 Hz), 1.23 (3H (17), s), 1.45 (1H (3"), dt, J=14.2, 6.8 Hz), 1.70 (1H (3"), dd, J=14.2, 6.8 Hz), 1.82 (3H (19), dd, J=2.7, 1.2 Hz), 2.09 (1H (11), dd, J=10.3, 6.4 Hz), 2.27 (1H (8), d, J=4.9 Hz), 2.38 (1H (2"), m, J=14.1, 7.0, 6.8 Hz), 2.72 (1H (4-OH), s), 3.37 (2H (2'), s), 3.53 (1H (10), d, J=2.4 Hz), 3.70 (1H (5), d, J=1.0 Hz), 3.72 (3H (4'), s), 3.80 (1H (20), m), 3.90 (1H (20), m), 4.46 (1H (7), d, J=2.4 Hz), 5.02 (1H (7-OH), d, J=5.9 Hz), 6.49 (1H (9-OH), s), 7.56 (1H (1), d, J=2.0 Hz).

$^{13}$C NMR (125 MHz, CDCl$_3$) δ ppm: 10.3 (19), 11.6 (4"), 13.9 (18), 16.2 (5"), 16.7 (16), 23.5 (17), 26.2 (3"), 26.5 (15), 34.8 (14), 35.2 (8), 41.3 (2"), 41.4 (2'), 43.3 (11), 52.5 (4'), 57.4 (10), 62.7 (5), 64.7 (20), 65.3 (13), 66.6 (6), 71.3 (4), 77.2 (7), 77.7 (12), 79.1 (9), 134.8 (2), 159.4 (1), 166.1 (1'), 166.1 (3'), 179.8 (1"), 205.5 (3).

Example 3: Preparation of Tigliane Derivatives

A number of compounds were prepared semi-synthetically by hydrolysis of the C-12 and C-13 esters of a mixture of the 5,20-acetonides of tigliane compounds such as Compound 1 and related compounds, followed by re-esterification at C-12 and C-13 with standard reagents using the following methods.

The crude mixture of tigliane esters for synthesis of tigliane analogues was prepared by coarsely powdering 150 g of seed of *Fontainea picrosperma* which was then extracted by stirring with acetone in a 1 L flask. After 4 hr, this suspension was vacuum-filtered, and the filtration cake was washed with acetone until TLC (PE:EtOAc:4:6) showed the absence of tigliane esters. The pooled filtrates were evaporated, affording a crude mixture of esters. Fats were then removed by a short gravity column chromatography on silica gel (petroleum, ether/ethyl acetate; PE/EtOAc 8:2→4:6 as eluent) to yield 8.2 g (5.5%) of crude esters mixture.

The mixture of esters was then protected, de-esterified and re-esterified at the C-12 and C-13 positions as illustrated in the following reactions using varying acyl groups to provide Compounds 21, 22, 23, 27, 28, 41, 42, 43, 44, 45, 46, 47, 48, 49, 50, 51, 52, 53 and 60.

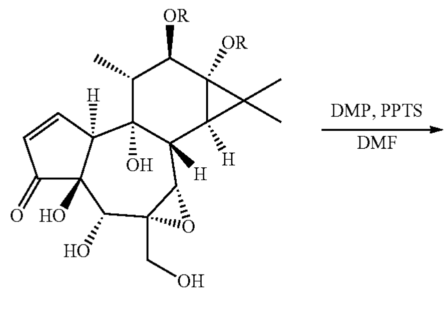

A

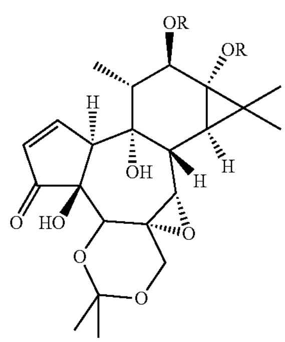

B

A 10 mL solution of the esters mixture A in dimethyl form amide (DMF) was added to a 50 mL solution of pyridinium-p-toluensulphonate (PPTS, 4.1 g, excess) in DMF (10 mL) and stirred at room temperature for 2 minutes. 120 mL of 2,2-dimethoxypropane (DMP) was then added and the solution stirred for 24 hr. The reaction was diluted with NaCl solution (150 mL) and washed with ethyl acetate (EtOAc, 50 mL). The organic phase was washed with NaCl solution, dried ($Na_2SO_4$), filtered and evaporated. The residue was purified by gravity column chromatography on silica gel (PE/EtOAc 8:2→6:4 as eluent) to afford 5.2 g (3.5%) of 5,20-acetonide esters mixture B. Unreacted starting material was reacted again under the same conditions to afford additional ester mixture B.

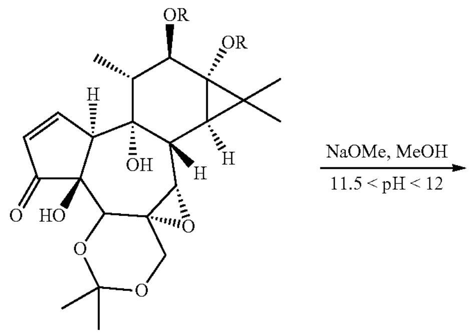

B

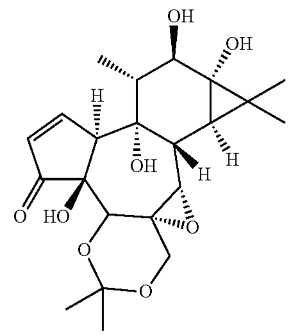

C

A 0.21N NaOMe solution was freshly prepared by slowly adding small pieces of sodium (9.7 g) to stirred methanol (HPLC grade, 2 L). Under vigorous stirring, 128 mL of this solution was then quickly added to 6.4 g of 5,20-acetonide esters mixture B. The pH of the resulting solution must be maintained in the range of 11.5-12.0 by judicious addition of 0.21 M NaOMe, taking care not to exceed pH 12.5. After stirring at room temperature for 24 hours, the reaction was neutralized with acetic acid, filtered and evaporated to ca. 1/20 of the original volume. EtOAc (20 mL) was added and the solution washed with 2N $H_2SO_4$ (100 mL). The acidic washing was counter-extracted with EtOAc, and the pooled EtOAc solutions were washed with NaCl solution (2×300 mL). After drying ($Na_2SO_4$), filtration and evaporation, the residue was purified by gravity column chromatography on silica gel (PE/EtOAc 6:4→4:6 as eluent) to afford 1.4 g of white powder.

Synthesis of Tigliane Analogues with Symetrical Esterification Pattern; Exemplary Methods Modified Steglich Esterification

1.

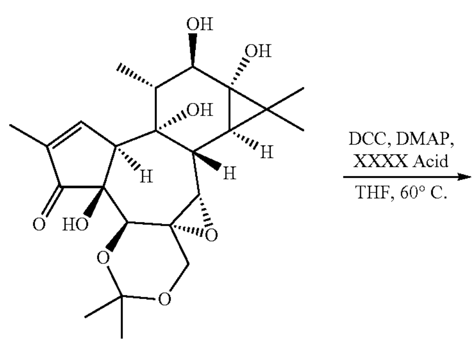

-continued

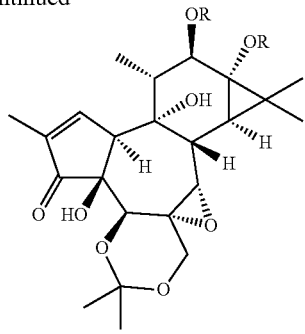

To a solution of deacyl-tigliane acetonide (100 mg; 0.23 mMol) in THF (5 mL), 4-dimethylaminopyridine (DMAP) (15 mg; 0.12 mMol) was added and the solution was heated to 60° C. (oil bath temperature). Separately, to a solution of the esterifying carboxylic acid (10 Eq) in THF (10 mL/g), N,N'-dicyclohexylcarbodiimide (DCC, 10 Eq) was added; after stirring for about 15 minutes, the suspension was filtered though a cotton wad, and added dropwise to the THF solution of deacyl-tigliane acetonide. After stirring 24 hours at 60° C., the reaction was worked up by dilution with EtOAe (≈200 mL) and washing with 2N $H_2SO_4$ (≈50 mL), brine (2×≈50 mL), and next with sat. $NaHCO_3$ (≈50 mL) and brine (2×≈50 mL). After drying ($Na_2SO_4$), filtration and evaporation, the residue was purified by gravity column chromatography on silica gel (PE/EtOAe 9:1→6:4 as eluent) to afford 111 mg (80%) of a white powder.

3.2 Deprotection

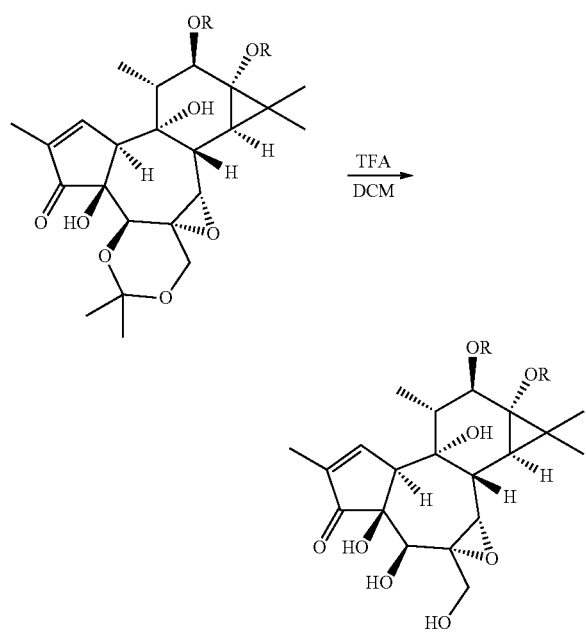

Method A (TFA in $CH_2Cl_2$)

The acetonide diester (100 mg) was added to a freshly prepared solution of trifloroacetic acid (TFA) in $CH_2Cl_2$ (2% V/V; 200 μL, 2 μL/mg). After stirring 6-12 h at room temp., the reaction was worked up by washing with a mixture of sat. $NaHCO_3$ (≈10 mL) and brine (≈40 mL), and next with brine alone (2×≈40 mL). After drying ($Na_2SO_4$), filtration and evaporation, the residue was purified by gravity column chromatography on silica gel (PE/EtOAc 8:2→2:8 as eluent) to afford the tigliane analogues (yield ca: 60-70%).

Method B ($HClO_4$ in MeOH)

The acetonide diester (100 mg) was added to a freshly prepared solution of $HClO_4$ in MeOH [pH range: 1.5-2.0]. After stirring at room temp. for 6-24 hours, the reaction was worked up by neutralization with sodium acetate, filtration and evaporation to ca. 1/20 of the original volume. EtOAc (10 mL) was next added, and the solution was washed with 2N $H_2SO_4$ (30 mL) and then with brine (30 mL). After drying ($Na_2SO_4$), filtration and evaporation, the residue was purified by gravity column chromatography on silica gel (PE/EtOAc-→4:6 as eluent) to afford the diester in ca. 60-70% yield.

This method was used to produce Compounds 27, 41, 42, 43, 44, 46, 49 and 60.

Synthesis of Unsymetrical Diesters, Exemplary Methods:
1.

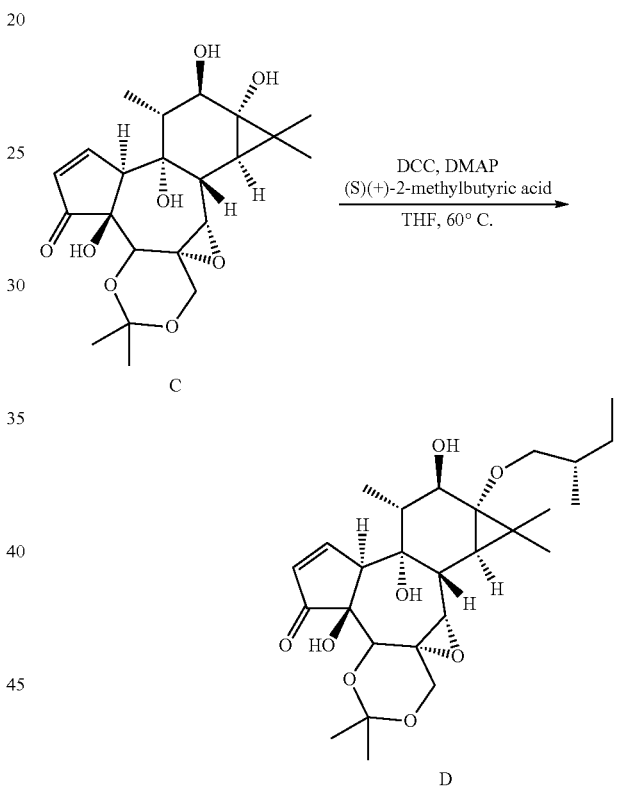

To a solution of 12,13-deacyl-5,20-acetonide (C) (1.4 g; 3.4 mMol) in 10 mL tetrahydrofuran (THF), 740 mL of 34 mMol triethylamine (TEA) was added and the solution was heated to 60° C. Separately, to a solution of (S)-(+)-2-methylbutyric acid (3.702 mL; 34 mMol) in THF (20 mL), N,N'-dicyclohexylcarbodiimide (DCC, 7,015 g; 34 mMol) was added. After stirring for about 15 minutes, the suspension was filtered and added to the warmed solution of the starting diol (C). After stirring 24 hours at 60° C., the reaction was diluted with EtOAc (≈200 mL) and washed with 2N $H_2SO_4$ (≈50 mL), NaCl solution (2×≈50 mL), and then with $NaHCO_3$ solution (≈50 mL) and NaCl solution (2×≈50 mL). After drying ($Na_2SO_4$), filtration and evaporation, the residue was purified by gravity column chromatography on silica gel (PE/EtOAc 9:1→6:4 as eluent) to afford 12-deacyl-5,20-acetonide-13-[(S)-(+)-2-methylbutyrate] (D) as white powder.

2.

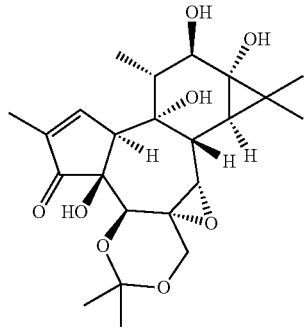

DCC, (DMAP)
2-methylbutyric acid
———————————→
THF, 60° C.

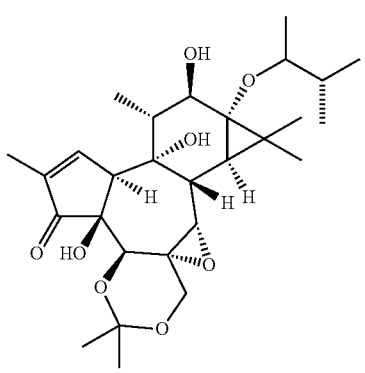

To a solution of 12,13-deacyl-5,20-acetonide C (100 mg; 0.25 mMol) in THF (5 mL), (S)-(+)-2-methylbutyric acid (109 µL; 1.00 mMol) and N,N'-dicyclohexylcarbodiimide (DCC, 206.33 mg; 1.00 mMol) were added. The solution was stirred at 60° C. (oil bath temperature) for 24 h, and then worked up by dilution with EtOAc (≈20 mL) and washing with 2N H$_2$SO$_4$ (≈50 mL), brine (2×≈50 mL), sat. NaHCO$_3$ (≈50 mL), and brine (2×≈50 mL). After drying (Na$_2$SO$_4$), filtration and evaporation, the residue was purified by gravity column chromatography on silica gel (PE/EtOAc 9:1→6:4 as eluent) to afford 106.2 mg (60%) of 12-deacyl-5,20-acetonide-13-((S)-2-methylbutyrate) D as white powder.

3.

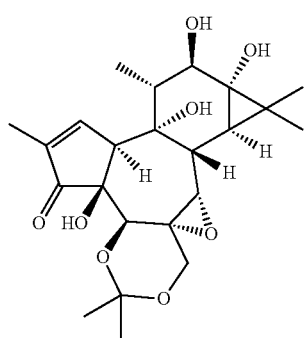

Acetic Anhydride, DIPEA
———————————→
THF, 50° C.

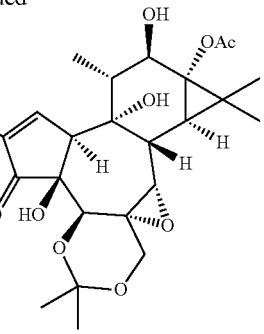

To a solution of 12,13-deacyl-5,20-acetonide C (100 mg; 0.25 mMol) in THF (5 mL), diisopropylethylamine (DIPEA) (131 µL; 0.75 mMol) and acetic anhydride (94 µL; 0.75 mMol) were added. After stirring for 72 h at room temp., EtOAc (10 mL) was added, and the solution was washed with 2N H$_2$SO$_4$ (2×20 mL) and brine (20 mL). After drying (Na$_2$SO$_4$), filtration and evaporation, the residue was purified by gravity column chromatography on silica gel (PE/EtOAc-→4:6 as eluent) to afford 12-deacyl-13-acetyl-5,20-acetonide 104 mg (87%) as a white powder.

4.

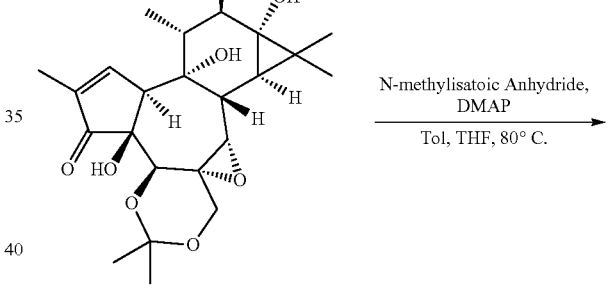

N-methylisatoic Anhydride, DMAP
———————————→
Tol, THF, 80° C.

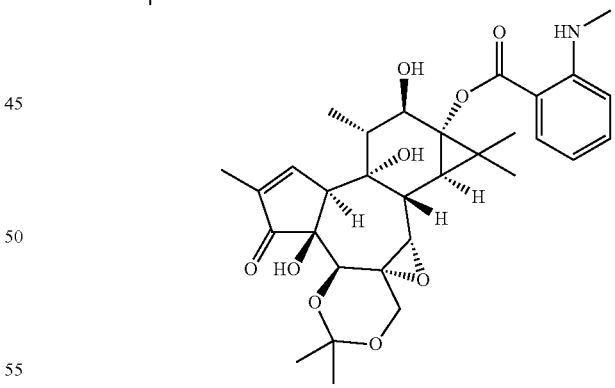

To a solution of deacyl-5,20-acetonide (100 mg; 0.25 mMol) in toluene (5 mL)/dimethylformamide (2 mL), N-methylisatoic anhydride (266 mg; 1.50 mMol) and dimethylaminopyridine (DMAP) (31 mg; 0.25 mMol) were added. After stirring 24 h at 80° C., the reaction was worked up by dilution with EtOAc (≈10 mL) and sequential washing with [2N H$_2$SO$_4$ (≈20 mL)+brine (≈60 mL)] (×2), and [sat. NaHCO$_3$ (≈20 mL)+brine (≈60 mL)] (×2). After drying (Na$_2$SO$_4$), filtration and evaporation, the residue was purified by gravity column chromatography on silica gel (PE/

EtOAc 9:1→7:3 as eluent) to afford 12-deacyl-13-[(N-methyl)-anthranilate-5,20-acetonide, 114 mg (80%) as a white powder.

Acylation of 13-Monoesters: Exemplary Methods

1.

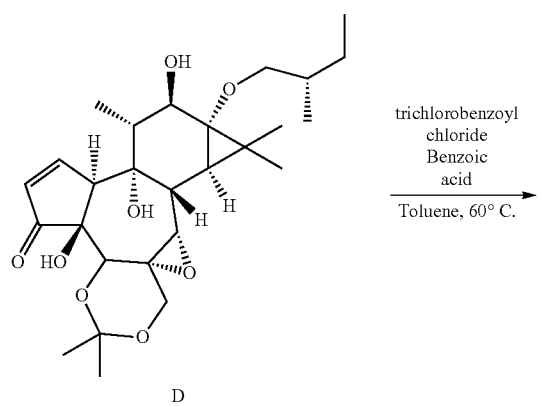

D

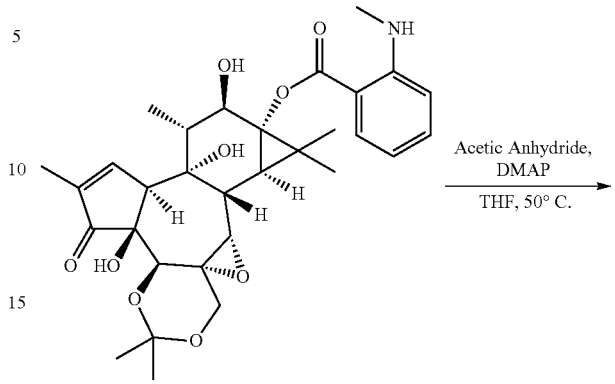

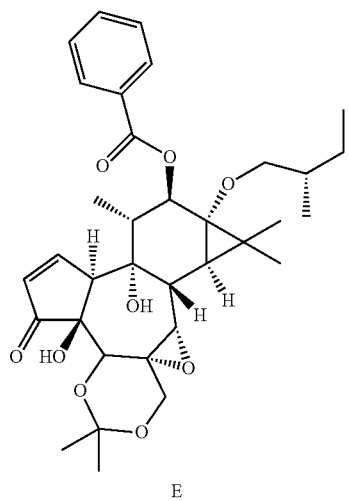

E

To a solution of 12-deacyl-5,20-acetonide-13-[(S)-(+)-2-methylbutyrate (D) (1062 mg; 2.04 mMol) in toluene (10 mL), dimethylaminopyridine (DMAP) (249 mg; 2.04 mMol) was added. Separately, to a solution of the benzoic acid 1224 mg; 10.02 mMol) in toluene (20 mL), triethylamine (1.397 mL; 10.02 mMol) was added and the solution stirred for about 2 minutes to complete dissolution; 2,4,6-trichlorobenzoyl chloride (1.566 mL; 10.02 mMol) was than added (Solution 1). After stirring the composition containing compound D for 6 hours, the suspension was filtered and poured into Solution 1. After stirring for 24 to 48 hours at 60° C., the reaction was diluted with EtOAc (≈10 mL) and washed with NH$_2$SO$_4$ solution (≈40 mL), NaCl solution (2×≈40 mL), and then with NaHCO$_3$ solution (≈40 mL) and NaCl solution (2×≈40 mL). After drying (Na$_2$SO$_4$), filtration and evaporation, the residue was purified by gravity column chromatography on silica gel (PE/EtOAc 9:1→7:3 as eluent) to afford, the 5,20-acetonide-12-benzoate-13-[(S)-(+)-2-methylbutyrate E as a white powder.

2.

To a solution of deacyl-13-(N-methyanthranoyl)-5,20-acetonide (100 mg; 0.18 mMol) in tetrahydrofuran (THF, 5 mL), acetic anhydride (51 mg; 0.54 mMol) and dimethylaminopyridine (DMAP) (2.2 mg; 0.018 mMol) were sequentially added. After stirring 6 h at 50° C., the reaction was worked up by dilution with EtOAc (ca. 10 mL) and sequential washing with 2N H$_2$SO$_4$ (2×ca. 40 mL), sat. NaHCO$_3$ (2×ca. 40 mL), and brine (2×ca. 40 mL). After drying (Na$_2$SO$_4$), filtration and evaporation, the residue was purified by gravity column chromatography on silica gel (PE/EtOAc 95:05→7:3 as eluent) to afford 12-acetyl-13-(N-methyl)anthranylate-5,20-acetonide, 105 mg (95%) as a white powder.

3.

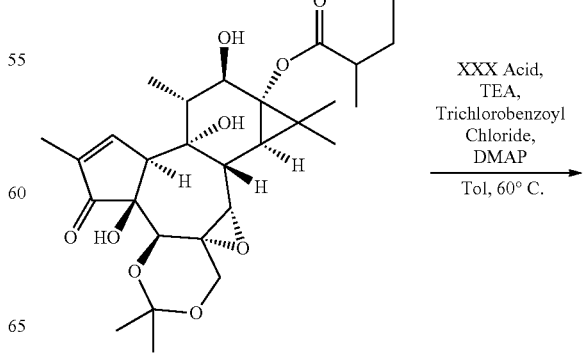

-continued

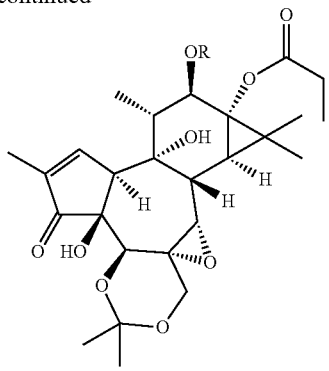

To a solution of 12-deacyl-5,20-acetonide-13-[(S)-2-methylbutyrate] (100 mg; 0.19 mMol) in toluene (5 mL), dimethylaminopyridine (DMAP) (23 mg; 0.19 mMol) was added. Separately, to a solution of tiglic acid (95 mg; 0.95 mMol) in toluene (5 mL), triethylamine (132 µL; 0.95 mMol) was added, and the solution stirred for about 2 min to complete solution; 2,4,6-trichlorobenzoyl chloride (148 µL; 0.95 mMol) was then added, and, after stirring for 6 h at room temp., the suspension was filtered (cotton wad) and added dropwise to the solution of the diterpenoid monoester in toluene. After stirring 24-48 h at 60° C., the reaction was worked up by dilution with EtOAc (ca. 10 mL) and washing with 2N $H_2SO_4$ (ca. 40 mL), brine (2×≈40 mL), and next with $NaHCO_3$ (ca. 40 mL) and brine (2×≈40 mL). After drying ($Na_2SO_4$), filtration and evaporation, the residue was purified by gravity column chromatography on silica gel (PE/EtOAc 9:1→7:3 as eluent) to afford 12-tigloyl-13-methylbutyryl-5,20-acetonide, 59 mg (50%) as a white powder.

4.

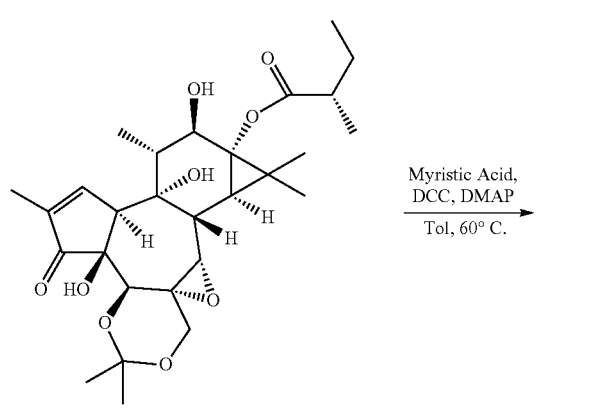

A solution of 12-deacyl-5,20-acetonide-13-(S)-2-methylbutyrate (100 mg; 0.19 mMol) in toluene (10 mL) was heated to 60° C., and myristic acid (217 mg; 0.95 mMol), N,N'-dicyclohexylcarbodiimide (DCC) (196 mg; 0.95 mMol) and dimethylaminopyridine (DMAP) (23 mg; 0.19 mMol) were sequentially added. After stirring 12 hours at 60° C., the reaction was worked up by dilution with EtOAc (≈10 mL) and washing with 2N $H_2SO_4$ (2×≈40 mL), sat. $NaHCO_3$ (2×≈40 mL), and brine (2×≈40 mL). After drying ($Na_2SO_4$), filtration and evaporation, the residue was purified by gravity column chromatography on silica gel (PE/EtOAc 9:1→7:3 as eluent) to afford 12-myristoyl-13-(2-methylbutanoyl)-5,20-acetonide, 121 mg (70%) as a white powder.

5.

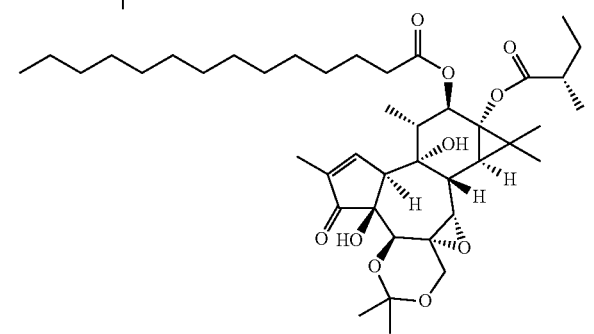

A solution of 12-deacyl-5,20-acetonide-13-acetate (100 mg; 0.25 mMol) in toluene (10 mL) was heated to 60° C. (oil bath temperature), and myristic acid (286 mg; 1.00 mMol), N,N'-dicyclohexylcarbodiimide (DCC) (206 mg; 1.00 mMol) and dimethylaminopyridine (DMAP) (31 mg; 0.25 mMol) were then added. After stirring 12 hours at 60° C., the reaction was worked up by dilution with EtOAe (ca. 10 mL) and washing with 2N $H_2SO_4$ (2×ca. 40 mL), sat. $NaHCO_3$ (2×ca. 40 mL), and brine (2×ca. 40 mL). After drying ($Na_2SO_4$), filtration and evaporation, the residue was purified by gravity column chromatography on silica gel (PE/EtOAc 9:1→7:3 as eluent) to afford 12-myristyl-13-acetyl-5,20-acetonide, 121 mg (70%) as a white powder.

6.

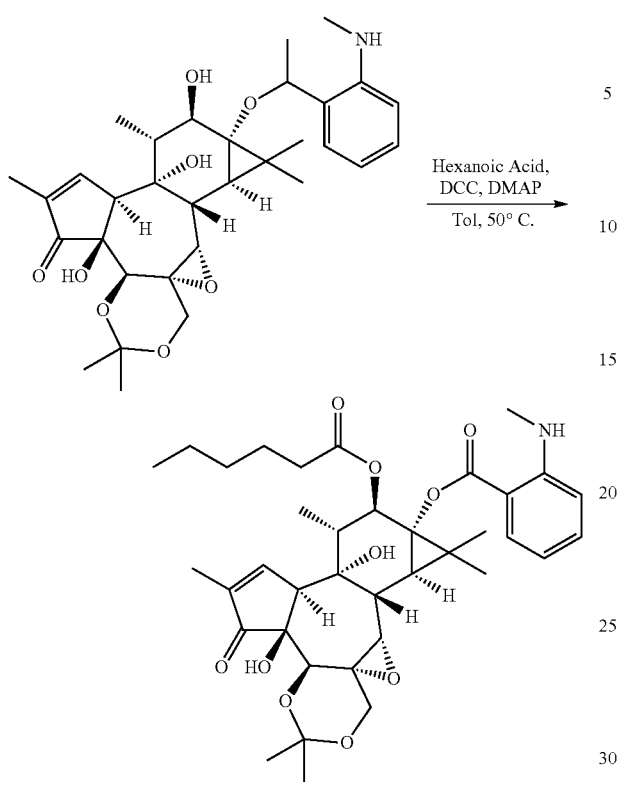

Hexanoic Acid, DCC, DMAP
Tol, 50° C.

To a heated (60° C., oil bath temperature) solution of deacyl-13-(N-methylanthranoyl)-5,20-acetonide (100 mg; 0.18 mMol) in toluene (10 mL), hexanoic acid (84 mg; 0.72 mMol), dicyclohexylcarbodiimide (DCC, 149 mg; 0.72 mMol), and dimethylaminopyridine (DMAP 22 mg; 0.18 mMol) were sequentially added. After stirring 12 h at 60° C., the reaction was worked up by dilution with EtOAc (ca. 10 mL) and sequential washing with 2N $H_2SO_4$ (2×ca. 40 mL), sat. $NaHCO_3$ (2×ca. 40 mL), and brine (2×ca. 40 mL). After drying ($Na_2SO_4$), filtration and evaporation, the residue was purified by gravity column chromatography on silica gel (PE/EtOAc 9:1→7:3 as eluent) to afford 12-hexanoyl-13-(N-methylanthranoyl)-5,20-acetonide, 108 mg (90%) as a white powder.

Deprotection
1.

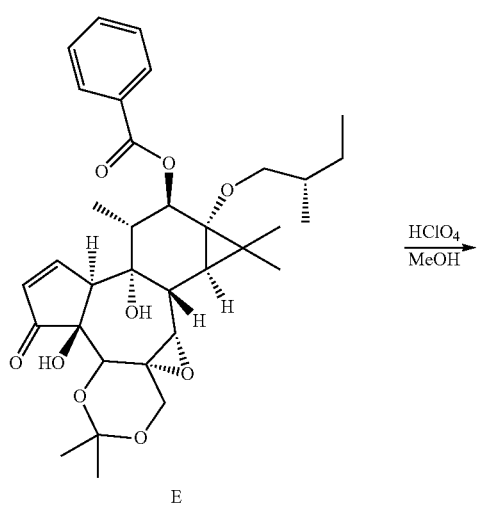

E

HClO₄ / MeOH

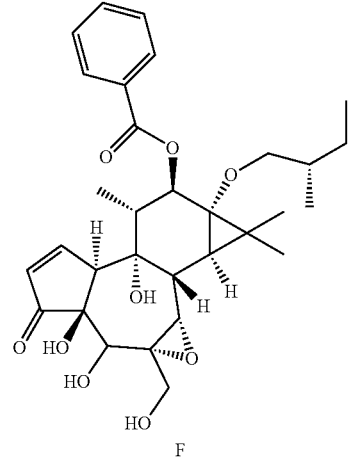

F

The 5,20-acetonide-12-benzoate-13-[(S)-(+)-2-methylbutyrate E (637 mg; 1.02 mMol) was added to a freshly prepared solution of $HClO_4$ in MeOH [1.5<pH<2.0]. After stirring for 6-24 hours, the reaction was neutralized with sodium acetate, filtered and evaporated to ca. 1/20 of the original volume. EtOAc (10 mL) was added, and the solution was washed with 2N $H_2SO_4$ (30 mL) and then with NaCl solution (30 mL). After drying ($Na_2SO_4$), filtration and evaporation, the residue was purified by gravity column chromatography on silica gel (PE/EtOAc-→4:6 as eluent) to afford the 12-benzoate-13-[(S)-(+)-2-methylbutyrate F (Compound 23) as white powder.

2.

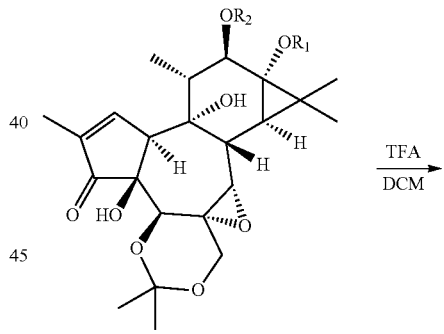

TFA / DCM

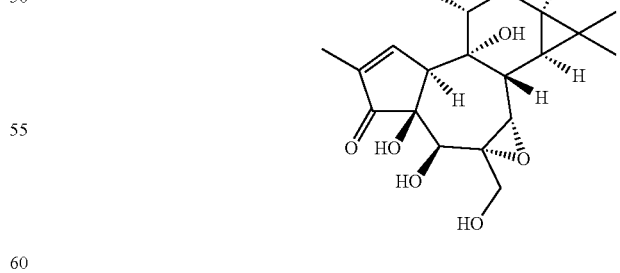

Reaction with 12-acetyl-13-N-methylanthranoyl-5,20-acetonide as representative: To a solution of 12-acetyl-13-N-methylanthranoyl-5,20-acetonide (100 mg; 0.16 mMol) in $CH_2Cl_2$ (10 mL), trifluoroacetic acid (TFA) (300 µL; 3% V/V) was added. After stirring about 12 hours, the reaction was worked up by washing with [$NaHCO_3$ (≈10 mL)+ brine (≈40 mL)] and next and brine (2×≈40 mL). After drying (Na₂SO₄), filtration and evaporation, the residue was purified by gravity column chromatography on silica gel (PE/EtOAc 8:2→2:8 as eluent) to afford 12-acetyl-13-(N-methylanthranoyl)-tigliane, 69 mg (75%) as a white powder.

Compounds 21, 22, 23, 28, 45, 47, 48, 50, 51, 52 and 53 were prepared by these methods.

Compound 21

$^1$H NMR (500 MHz, CDCl₃) δ ppm: 0.84 (3H, d, J=6.6 Hz), 0.93 (3H, t, J=7.4 Hz), 1.21 (3H, s), 1.23 (3H, s), 1.29 (1H, d, J=6.7 Hz), 1.64 (2H, sxt, J=7.6 Hz), 1.73 (3H, dd, J=2.9, 1.3 Hz), 1.77 (3H, dq, J=7.2, 1.2 Hz), 1.79-1.81 (3H, m), 1.95 (1H, dd, J=9.9, 6.5 Hz), 2.24-2.38 (2H, m), 3.16 (1H, d, J=6.7 Hz), 3.26 (1H, d, J=0.5 Hz), 3.65 (1H, s), 3.83 (2H, dd, J=13.3, 12.5 Hz), 3.94 (1H, d, J=3.1 Hz, OH), 4.06 (1H, t, J=2.6 Hz), 4.22 (1H, s), 5.41 (1H, d, J=9.9 Hz), 5.82-6.00 (1H, br.s., OH), 6.80 (1H, qq, J=7.1, 1.4 Hz), 7.71 (1H, dd, J=2.6, 1.3 Hz).

$^{13}$C NMR (125 MHz, CDCl₃) δ ppm: 9.72, 12.20, 13.62, 14.43, 15.07, 17.12, 18.03, 23.66, 26.35, 35.98, 36.03, 36.13, 45.76, 48.92, 61.77, 64.56, 65.23, 65.65, 71.36, 72.41, 76.74, 77.20, 128.38, 133.46, 137.73, 164.63, 167.62, 176.12, 209.88.

Compound 22

$^1$H NMR (500 MHz, CDCl₃) δ ppm: 0.85 (3H, d, J=7.3 Hz), 0.86 (3H, t, J=7.2 Hz), 1.20 (3H, s), 1.21 (3H, s), 1.20-1.40 (10H, m), 1.29 (1H, d, J=6.8 Hz), 1.67 (2H, d, J=13.7 Hz), 1.75 (3H, dd, J=2.9, 1.0 Hz), 1.88-1.92 (2H, m) 1.89-1.95 (1H, m), 3.07 (2H, dd, J=6.8, 1.5 Hz), 3.15 (1H, d, J=6.4 Hz), 3.26 (1H, s), 3.85 (2H, dd, J=12.7, 4.4 Hz), 4.04 (1H, d, J=2.9 Hz), 4.21 (1H, s), 5.13-5.15 (1H, m), 5.16-5.18 (1H, m), 5.35 (1H, d, J=9.8 Hz), 5.82-5.92 (1H, m), 7.70 (1H, dd, J=2.4, 1.0 Hz).

$^{13}$C NMR (125 MHz, CHLOROFORM-d) δ ppm: 9.74, 14.08, 15.12, 17.03, 22.63, 23.69, 24.48, 26.51, 29.07, 29.08, 29.19, 31.81, 34.25, 36.01, 36.04, 39.29, 45.50, 48.94, 61.69, 64.54, 65.21, 65.49, 71.58, 72.35, 77.17, 77.41, 118.62, 130.03, 133.55, 164.54, 171.11, 176.25, 209.86.

Compound 23

$^1$H NMR (500 MHz, CDCl₃) δ ppm: 0.90 (3H, d, J=6.5 Hz), 0.94 (3H, t, J=7.5 Hz), 1.14 (3H, d, J=7.1 Hz), 1.22 (3H, s), 1.32 (1H, d, J=6.6 Hz), 1.35 (3H, s), 1.41-1.51 (1H, m, J=14.1, 7.5, 7.0 Hz), 1.69-1.79 (1H, m), 1.73 (3H, dd, J=2.9, 1.3 Hz), 2.08 (1H, dq, J=9.9, 6.5 Hz), 2.39 (1H, sxt, J=7.0 Hz), 3.24 (1H, d, J=6.6 Hz), 3.29 (1H, s), 3.84 (2H, dd, J=12.8, 1.3 Hz), 4.10 (1H, t, J=2.5 Hz), 4.24 (1H, d, J=0.7 Hz), 5.62 (1H, d, J=9.9 Hz), 6.07 (1H, br.s., OH), 7.43 (2H, t, J=7.7 Hz), 7.55 (1H, tt, J=7.5, 1.3 Hz), 7.72 (1H, dd, J=2.6, 1.3 Hz), 7.99 (2H, dm, J=8.4, 1.3 Hz)

$^{13}$C NMR (125 MHz, CDCl₃) δ ppm: 9.73, 11.61, 15.14, 16.14, 17.32, 23.63, 26.18, 26.82, 36.03, 36.34, 41.22, 45.92, 48.92, 61.86, 64.59, 65.20, 65.48, 71.27, 72.46, 77.23, 77.60, 128.44 (2C), 129.70 (2C), 130.02, 133.07, 133.52, 164.54, 165.94, 179.00, 209.84.

Compound 27

$^1$H NMR (500 MHz, CDCl₃) δ ppm: 0.85 (3H, d, J=6.5 Hz), 0.93 (6H, t, J=7.4 Hz), 1.20 (6H, s), 1.28 (1H, d, J=6.6 Hz), 1.58-1.68 (4H, m), 1.74 (3H, d, J=1.8 Hz), 1.91 (1H, dq, J=10.0, 6.4 Hz), 2.20-2.36 (4H, m), 3.14 (1H, d, J=6.6 Hz), 3.25 (1H, s), 3.63 (1H, s, OH), 3.76-3.86 (1H, m), 3.93 (1H, d, J=3.1 Hz, OH), 4.05 (1H, d, J=2.4 Hz), 4.21 (1H, d, J=2.4 Hz), 5.36 (1H, d, J=10.0 Hz), 5.84 (1H, br.s., OH), 7.70 (1H, s).

$^{13}$C NMR (125 MHz, CHLOROFORM-d) δ ppm: 9.72, 13.46, 13.62, 15.04, 17.02, 18.01, 18.61, 23.66, 26.34, 35.90, 35.95, 36.14, 36.38, 45.42, 48.90, 61.79, 64.58, 65.21, 65.60, 71.34, 72.40, 76.59, 77.18, 133.49, 164.54, 173.30, 176.05, 209.85.

Compound 28

$^1$H NMR (500 MHz, CDCl₃) δ ppm: 0.91 (3H, d, J=6.6 Hz), 0.96 (3H, t, J=7.4 Hz), 1.21 (3H, s), 1.34 (3H, s), 1.36 (1H, d, J=3.4 Hz), 1.60-1.72 (2H, m), 1.74 (3H, d, J=2.1. Hz), 2.09 (1H, dd, J=9.8, 6.5 Hz), 2.31 (1H, t, J=15.9, 7.6 Hz), 2.38 (1H, t, J=15.9, 7.6 Hz), 3.24 (1H, d, J=6.7 Hz), 3.29 (1H, s), 3.80 (1H, d, J=12.4 Hz), 3.87 (1H, d, J=12.4 Hz), 4.09 (1H, d, J=2.7 Hz), 4.24 (1H, s), 5.62 (1H, d, J=9.9 Hz), 7.43 (2H, t, J=7.7 Hz), 7.56 (1H, t, J=7.4 Hz), 7.73 (1H, s), 7.99 (2H, d, J=7.3 Hz)

$^{13}$C NMR (125 MHz, CDCl₃) δ ppm: 9.73, 13.65, 15.16, 17.25, 18.07, 23.66, 26.59, 36.07, 36.18, 36.23, 45.80, 48.95, 61.74, 64.55, 65.23, 65.62, 71.54, 72.40, 77.21, 77.63, 128.46 (2C), 129.72 (2C), 129.98, 133.12, 133.56, 164.57, 166.15, 176.19, 209.88.

Compound 41

$^1$H NMR (500 MHz, CDCl₃) δ ppm: 0.85 (3H (18), d, J=7.3 Hz), 0.85 (3H (9'), t, J=7.3 Hz), 0.86 (3H (9"), t, J=6.8 Hz), 1.20 (3H (16), s), 1.20 (3H (17), s), 1.22-1.30 (10H (4', 5', 6', 7', 8'), m), 1.22-1.30 (10H, 4", 5", 6", 7", 8"), m), 1.28 (1H (14), d, J=6.8 Hz), 1.53-1.62 (2H (3"), m), 1.56-1.63 (2H (3'), m), 1.74 (3H (19), dd, J=2.9, 1.3 Hz), 1.90 (1H (11), dq, J=10.1, 6.5 Hz), 2.19 (1H (20-OH), t, J=6.8 Hz), 2.24-2.32 (2H (2'), m), 2.29-2.37 (2H (2"), m), 3.14 (1H (8), d, J=6.8 Hz), 3.26 (1H (7), s), 3.59 (1H (4-OH), s), 3.78 (1H (20), dd, J=12.5, 5.2 Hz), 3.82-3.87 (1H (20), m, J=12.5, 7.3 Hz), 3.89 (1H (5-OH), d, J=3.1 Hz), 4.05 (1H (10), dq), 4.21 (1H (5), d, J=2.6 Hz), 5.36 (1H (12), d, J=10.4 Hz), 5.86 (1H 9-OH), br.s.), 7.70 (1H (1), dd, J=2.6, 1.6 Hz).

$^{13}$C NMR (125 MHz, CDCl₃) δ ppm: 9.7 (19), 14.1 (9"), 14.1 (9'), 15.1 (18), 17.0 (16), 22.6 (8"), 22.6 (8'), 23.7 (17), 24.5 (3"), 25.2 (3'), 26.3 (15), 28.99 (4"), 29.07 (6'), 29.07 (6"), 29.15 (4'), 29.18. (5"), 29.2 (4'), 29.22 (5'), 31.78 (7"), 31.80 (7'), 34.3 (2"), 34.5 (2'), 35.9 (14), 36.0 (8), 45.4 (11), 48.9 (10), 61.7 (6), 64.5 (20), 65.2 (7), 65.6 (13), 71.5 (5), 72.4 (4), 76.5 (12), 77.2 (9), 133.5 (2), 164.6 (1), 173.5 (1'), 176.2 (1"), 209.9 (3).

Compound 42

$^1$H NMR (500 MHz, CDCl₃) δ ppm: 0.84 (3H (18), d, J=6.2 Hz), 0.87 (3H (6'), t, J=7.0 Hz), 0.88 (3H (6"), t, J=7.0 Hz), 1.20 (3H (17), s), 1.21 (3H (16), s), 1.25-1.31 (2H (4'), m), 1.25-1.31 (2H (4"), m), 1.26-1.32 (2H (5"), m), 1.26-1.32 (2H (5'), m), 1.27-1.29 (1H (14), m, J=6.8 Hz), 1.57-1.62 (2H (3"), m), 1.58-1.63 (2H (3'), m), 1.74 (3H (19), dd, J=2.9, 1.3 Hz), 1.91 (1H (11), dq, J=10.1, 6.5 Hz), 2.20 (1H (20-OH), t, J=6.8 Hz), 2.26-2.30 (2'), m), 2.29-2.34 (2H (2"), m), 3.14 (1H (8), d, J=6.8 Hz), 3.26 (1H (7), s), 3.59 (1H (4-OH), d, J=1.0 Hz), 3.78 (1H (20), dd, J=12.5, 5.2 Hz), 3.82-3.87 (1H, (20), m), 3.88 (1H (5-OH), d, J=3.1 Hz), 4.05 (1H (10), t, J=2.6 Hz), 4.21 (1H (5), d, J=3.6 Hz), 5.36 (1H (12), d, J=9.9 Hz), 5.86 (1H, (9-OH), br.s.), 7.70 (1H (1), dd, J=2.3, 1.3 Hz), ¹³C NMR (125 MHz, CDCl₃) δ ppm: 9.7 (19), 13.8 (6"), 13.9 (6'), 15.1 (18), 17.0 (16), 22.26 (5"), 22.3 (5'), 23.7 (17), 24.1 (3"), 24.8 (3'), 26.3 (15), 31.1 (4"), 31.2 (4'), 34.2 (2"), 34.5 (2'), 35.9 (14), 36.0 (8), 45.4 (11), 48.9 (10), 61.7 (6), 64.5 (20), 65.2 (7), 65.6 (13), 71.5 (5), 72.4 (4), 76.5 (12), 77.2 (9), 133.5 (2), 164.6 (1), 173.5 (1'), 176.2 (1"), 210.0 (3).

Compound 43

¹H NMR (500 MHz, CDCl₃) δ ppm: 0.85 (3H (18), d, J=6.5 Hz), 0.89 (3H (5'), t J=7.2 Hz), 0.90, (3H (5"), t, J=7.3 Hz), 1.21 (3H (16), s), 1.21 (3H (17), s), 1.28 (1H (14), d, J=6.6 Hz), 1.29-1.37 (2H (4"), m), 1.29-1.38 (2H (4'), m), 1.55-1.59 (2H (3"), m), 1.56-1.62 (2H (3'), m), 1.75 (3H (19), dd, J=2.9, 1.2 Hz), 1.91 (1H (11), dq, J=10.1, 6.5 Hz), 2.19 (1H (20-OH), t, J=6.6 Hz), 2.24-2.32 (2H (2'), m), 2.30-2.38 (2H (2"), m), 3.15 (1H (8), d, J=6.6 Hz), 3.25 (1H (7), s), 3.59 (1H (4-OH), s), 3.78 (1H (20), dd, J=12.6, 5.2 Hz), 3.85 (1H (20), dd, J=12.6, 7.4 Hz), 3.88 (1H (20-OH), d, J=3.1 Hz), 4.05 (1H (10), t, J=2.6 Hz), 4.21 (1H (5), d, J=2.3 Hz), 5.36 (1H (12), d, J=10.0 Hz), 5.85 (1H (9-OH), br.s.), 7.70 (1H (1), dd, J=2.3, 1.4 Hz).

¹³C NMR (125 MHz, CDCl₃) δ ppm: 9.7 (19), 13.65 (5"), 13.68 (5'), 15.1 (18), 17.0 (16), 22.1 (4"), 22.2 (4'), 23.7 (17), 26.4 (15), 26.5 (3"), 27.2 (3'), 34.0 (2"), 34.2 (2'), 35.9 (14), 36.0 (8), 45.5 (11), 48.9 (10), 61.7 (6), 64.6 (20), 65.2 (7), 65.6 (13), 71.5 (5), 72.4 (4), 76.6 (12), 77.2 (9), 133.5 (2), 164.6 (1), 173.5 (1'), 176.2 (1"), 209.9 (3).

Compound 44

¹H NMR (500 MHz, CDCl₃) δ ppm: 0.86 (3H (18), d, J=6.2 Hz), 1.24 (3H (16), s), 1.26 (3H (17), s), 1.33 (1H (14), d, J=6.8 Hz), 1.74 (3H (19), dd, J=2.9, 1.3 Hz), 1.76-1.78 (2H (4'), m), 1.77-1.79 (2H (4"), m), 1.78-1.79 (3H (5"), m), 1.80-1.81 (3H (5'), m), 1.97 (1H (11), dq, J=9.9, 6.4 Hz), 2.19 (1H (20-OH), br.s.), 3.18 (1H (8), d, J=6.8 Hz), 3.27 (1H (7), s), 3.60 (1H (4-OH), s), 3.74-3.81 (1H (20), m), 3.86 (1H (20), br.s.), 3.89 (1H (5-OH), br.s.), 4.04-4.11 (1H (10), m), 4.22 (1H (5), s), 5.45 (1H (12), d, J=9.9 Hz), 6.28 (1H (9-OH), br.s.), 6.75-6.83 (1H (3'), m), 6.85-6.94 (1H (3"), m), 7.72 (1H (1), dd, J=2.6, 1.6 Hz).

¹³C NMR (125 MHz, CDCl₃) δ ppm: 9.7 (19), 11.8 (5"), 12.2 (5'), 14.4 (4'), 14.7 (4"), 15.2 (18), 17.3 (16), 23.7 (17), 26.8 (15), 36.1 (8), 36.2 (14), 45.9 (11), 49.0 (10), 61.6 (6), 64.5 (20), 65.3 (7), 65.6 (13), 71.7 (5), 72.4 (4), 77.0 (12), 77.2 (9), 128.2 (2'), 128.5 (2"), 133.4 (2), 137.6 (3'), 139.8 (3"), 164.9 (1), 167.5 (1'), 169.7 (1"), 210.0 (3).

Compound 45

¹H NMR (500 MHz, CDCl₃) δ ppm: 0.79 (3H (18), d, J=6.6 Hz), 0.93 (3H (4'''), t, J=7.5 Hz), 1.13 (3H (5'''), d, J=7.0 Hz), 1.24 (3H (17), s), 1.28 (3H (16), s), 1.28 (1H (14), d, J=6.7 Hz), 1.45 (1H (3'''), dq, J=14.1, 7.3 Hz), 1.69-1.76 (1H (3'''), m), 1.71 (3H (19), dd, J=2.8, 1.4), 1.77 (3H (4"), dq, J=7.1, 1.1 Hz), 1.79-1.81 (3H (5"), m), 1.90 (1H (11), dq, J=9.8, 6.5 Hz), 2.01 (3H (2''''), s), 2.18 (3H (2'), s), 2.38 (1H (2'''), sxt, J=7.0 Hz), 2.99 (1H (4-OH), s), 3.15 (1H (7), s), 3.26 (1H (8), d, J=6.8 Hz), 3.54 (1H (20), d, J=12.1 Hz), 4.14-4.17, (1H (10), m), 4.69 (1H (20), d, J=12.1 Hz), 5.42 (1H (12), d, J=9.9 Hz), 5.52 (1H (5), s), 5.98 (1H (9-OH), br.s.), 6.80 (1H (3"), qq, J=7.1, 1.3 Hz), 7.62 (1H (1), dd, J=2.3, 1.2 Hz).

¹³C NMR (125 MHz, CDCl₃) δ ppm: 9.8 (19), 11.6 (4'''), 12.2 (5"), 14.4 (4"), 15.0 (18), 16.2 (5'''), 17.3 (16), 20.7 (2''''), 20.8 (2'), 23.7 (17), 26.2 (3'''), 26.7 (15), 36.0 (14), 36.1 (8), 41.2 (2'''), 45.8 (11), 49.4 (10), 60.4 (6), 65.4 (7), 65.6 (13), 66.3 (20), 68.1 (5), 71.8 (4), 76.7 (12), 76.9 (9), 128.5 (2"), 133.8 (2), 137.6 (3"), 162.5 (1), 167.4 (1"), 168.8 (1'), 170.6 (1''''), 178.9 (1'''), 206.3 (2).

Compound 46

¹H NMR (500 MHz, CDCl₃) δ ppm: 0.87 (3H (18), d, J=6.6 Hz), 1.23 (3H (16), s), 1.25 (3H (17), s), 1.34 (1H (14), d, J=6.8 Hz), 1.75 (3H (19), dd, J=2.6, 1.0 Hz), 1.82-1.85 (3H (6'), m), 1.82-1.85 (3H (6"), m), 1.93-1.99 (1H (11), m), 3.17 (1H (8), d, J=6.8 Hz), 3.27 (1H (7), br.s.), 3.78 (1H (20), d, J=12.6 Hz), 3.85 (1H (20), d, J=12.2 Hz), 4.05-4.08 (1H (10), m), 4.22 (1H (5), d, J=1.6 Hz), 5.47 (1H (12), d, J=9.9 Hz), 5.73 (1H (2'), d, J=15.2 Hz), 5.75 (1H (2"), d, J=15.1 Hz), 6.08-6.19 (1H (4'), m), 6.08-6.19 (1H (4"), m), 6.14-6.19 (1H (5'), m), 6.15-6.18 (1H (5"), m), 7.16-7.23 (1H (3'), m), 7.26-7.33 (1H (3"), m), 7.71-7.73, (1H (1), m).

¹³C NMR (125 MHz, CDCl₃) δ ppm: 9.7 (19), 15.2 (18), 17.2 (16), 18.7 (6'), 18.7 (6"), 23.6 (17), 26.7 (15), 36.1 (8), 36.2 (14), 45.9 (11), 49.0 (10), 61.6 (6), 64.6 (20), 65.3 (7), 65.6 (13), 71.7 (5), 72.4 (4), 77.0 (12), 77.1 (9), 117.7 (2"), 118.7 (2'), 129.7 (4'), 129.7 (4"), 133.4 (2), 139.7 (5'), 141.0 (5"), 145.5 (3'), 147.3 (3"), 164.8 (1), 166.8 (1'), 169.2 (1"), 210.0 (3).

Compound 47

¹H NMR (500 MHz, CDCl₃) δ ppm: 0.89 (3H (18), d, J=6.7 Hz), 0.90 (3H (6'), t, J=6.7 Hz), 1.28 (3H (16), s), 1.29-1.34 (2H (4'), m), 1.30-1.35 (2H (5'), m), 1.31 (3H (17), s), 1.40 (1H (14), d, J=6.6 Hz), 1.60-1.65 (2H (3'), m), 1.77 (3H (19), dd, J=2.7, 1.2 Hz), 1.97 (1H (11), dq, J=9.9, 6.5 Hz), 2.14 (1H (20-OH), dd, J=7.4, 6.4 Hz), 2.30 (2H, (2'), td, J=7.4, 7.3 Hz), 2.87 (3H (MeNH), d, J=4.8 Hz), 3.22 (1H (8), d, J=6.6 Hz), 3.29 (1H (7), s), 3.80 (1H (20), dd, J=12.5, 5.7 Hz), 3.86 (1H (20), dd, J=12.9, 7.8 Hz), 4.08-4.11 (1H (10), m), 4.24 (1H (5), d, J=2.5 Hz), 5.53 (1H (12), d, J=9.9 Hz), 6.30-6.37 (1H (9-OH), m), 6.52 (1H (6"), ddd, J=7.9, 7.0, 0.9 Hz), 6.64 (1H (4"), d, J=8.4 Hz), 7.36 (1H (5"), ddd, J=8.4, 7.1, 1.4 Hz), 7.56 (1H (3"NH), q, J=4.8 Hz), 7.75 (1H, 7"), dd, J=8.2, 1.6 Hz), 7.72-7.76 (1H (1), m).

¹³C NMR (125 MHz, CDCl₃) δ ppm: 9.8 (19), 14.0 (6'), 15.2 (18), 17.2 (16), 22.4 (5'), 23.9 (17), 24.9 (3'), 27.0 (15), 29.5 (MeNH), 31.2 (4'), 34.5 (2'), 36.1 (8), 36.2 (14), 45.7 (11), 49.0 (10), 61.8 (6), 64.6 (20), 65.4 (7), 65.5 (13), 71.6 (5), 72.4 (4), 76.8 (12), 77.4 (9), 108.6 (2"), 111.0 (4"), 114.5 (6"), 131.8 (7"), 133.6 (2), 135.6 (5"), 152.7 (3"), 164.4 (1), 170.2 (1"), 173.2 (1'), 209.9 (3).

Compound 48

¹H NMR (500 MHz, CDCl₃) δ ppm: 0.9 (3H (18), d, J=6.6 Hz), 1.27 (3H (16), s), 1.32 (3H (17), s), 1.4 (1H (14), d, J=6.6 Hz), 1.77 (3H (19), dd, J=2.7, 1.0 Hz), 1.98 (1H (11), dq, J=9.9, 6.5 Hz), 2.05 (3H (2'), s), 2.88 (3H (MeNH), d, J=5.1 Hz), 3.22 (1H (8), d, J=6.6 Hz), 3.29 (1H (7), s), 3.80 (1H (20), dd, J=12.2, 5.2 Hz), 3.83-3.88 (1H (20), m), 4.09 (1H (10), br.s.), 4.24 (1H (5), d, J=2.9 Hz), 5.49 (1H (12), d, J=9.9 Hz), 6.53 (1H (6"), t, J=7.6 Hz), 6.64 (1H (4"), d, J=8.6 Hz), 7.36 (1H (5"), ddd, J=8.4, 7.0, 1.6 Hz), 7.55 (1H (3"-NH), q, J=4.6 Hz), 7.73 (1H (1), s), 7.78 (1H (7"), dd, J=8.0, 1.6 Hz).

¹³C NMR (125 MHz, CDCl₃) δ ppm: 9.8 (19), 15.3 (18), 17.2 (16), 21.0 (2'), 23.9 (17), 27.1 (15), 29.5 (MeNH), 36.1 (8), 36.3 (14), 45.8 (11), 49.0 (10), 61.8 (6), 64.6 (20), 65.3

(7), 65.4 (13), 71.6 (5), 72.4 (4), 77.3 (9), 77.4 (12), 108.6 (2″), 111.0 (4″), 114.5 (6″), 131.9 (7″), 133.6 (2), 135.6 (5″), 152.7 (3″), 164.4 (1), 170.3 (1″), 170.4 (1′), 209.9 (3).

Compound 49

$^1$H NMR (500 MHz, CDCl$_3$) δ ppm: 0.84 (3H (18), d, J=6.8 Hz), 0.86 (3H (7′), t, J=6.7 Hz), 0.86 (3H (7″), t, J=6.7 Hz), 1.20 (3H (16), s), 1.20 (3H (17), s), 1.22-1.32 (12H, (4′, 5′, 6′, 4″, 5″, 6″), m), 1.28 (1H (14), d, J=6.7 Hz), 1.55-1.63 (4H (3′, 3″), m), 1.74 (3H (19), dd, J=2.6, 1.0 Hz), 1.90 (1H (11), m), 2.28 (2H (2″), m), 2.32 (2H (2′), m), 3.14 (1H (8), d, J=6.7 Hz), 3.25 (1H (7), s), 3.65 (1H (4-OH), s), 3.81 (2H (20), br.s.), 3.97 (1H (5-OH), br.s.), 4.05 (1H (10), t, J=2.6 Hz), 4.21 (1H (5), s), 5.35 (1H (12), d, J=9.9 Hz), 5.85 (1H (9-OH), br.s.), 7.70 (1H (1), dd, J=2.6, 1.6 Hz),
$^{13}$C NMR (125 MHz, CDCl$_3$) δ ppm: 9.7 (19), 14.0 (7′), 14.0 (7″), 15.0 (18), 17.0 (16), 22.4 (6″), 22.5 (6′), 23.7 (17), 24.4 (3′), 25.1 (3″), 26.3 (15), 28.7 (4′), 28.7 (4″), 31.4 (5′), 31.4 (5″), 34.3 (2′), 34.5 (2″), 35.9 (8), 35.9 (14), 45.4 (11), 48.9 (10), 61.8 (6), 64.6 (20), 65.2 (7), 65.6 (13), 71.3 (5), 72.4 (4), 76.5 (9), 77.2 (9), 133.5 (2), 164.5 (1), 173.5 (1′), 176.2 (1″), 209.8 (2).

Compound 50

$^1$H NMR (500 MHz, CDCl$_3$) δ ppm: 0.84 (3H (18), d, J=6.8 Hz), 0.85 (3H (14′), t, J=6.8 Hz), 1.20 (3H (16), s), 1.20 (3H (17), s), 1.21-1.28 (20H (4′, 5′, 6′, 7′, 8′, 9′, 10′, 11′, 12′, 13′), m), 1.30 (1H (14), d, J=6.8 Hz), 1.60 (2H (3′), quin, J=7.3 Hz), 1.74 (3H (19), dd, J=2.9, 1.3 Hz), 1.91 (1H (11), dq, J=10.1, 6.5 Hz), 2.07 (3H, (2″), s), 2.23-2.34 (2H (2′), m), 3.14 (1H (8), d, J=6.8 Hz), 3.24 (1H (7), s), 3.46 (1H (5-OH), s), 3.65 (1H (4-OH), s), 3.77-3.83 (2H (20), m, J=3.1 Hz), 3.97 (1H (20-OH), d, J=3.1 Hz), 4.04 (1H (10), t, J=2.6 Hz), 4.21 (1H (5), d, J=2.1 Hz), 5.36 (1H (12), d, J=10.4 Hz), 5.70 (1H (9-OH), br.s.), 7.69 (1H (1), dd, J=2.6, 1.6 Hz).
$^{13}$C NMR (125 MHz, CDCl$_3$) δ ppm: 9.7 (19), 14.1 (14′), 15.0 (18), 17.0 (16), 21.0 (2″), 22.7 (13′), 23.6 (17), 25.1 (3′), 26.2 (15), 29.0 (4′), 29.2 (5′), 29.3 (6′), 29.5 (7′), 29.6 (8′), 29.6 (8′), 29.6 (9′), 29.6 (10′), 29.6 (11′), 31.9 (12′), 34.5 (2′), 35.8 (14), 35.9 (8), 45.3 (11), 48.9 (10), 61.8 (6), 64.6 (20), 65.2 (7), 65.8 (13), 71.2 (5), 72.4 (4), 76.5 (12), 77.2 (9), 133.5 (2), 164.4 (1), 173.6 (1′), 173.6 (1″), 209.8 (3).

Compound 51

$^1$H NMR (500 MHz, CDCl$_3$) δ ppm: 0.84 (3H (18), d, J=6.8 Hz), 0.86 (3H (14′), t, J=7.0 Hz), 0.92 (3H (4″), t, J=7.5 Hz), 1.12 (3H (5″), d, J=6.8 Hz), 1.21 (3H (16), s), 1.22 (3H (17), s), 1.21-1.31 (20H (4′, 5′, 6′, 7′, 8′, 9′, 10′, 11′, 12′, 13′), m), 1.25 (1H (14), d, J=6.2 Hz), 1.44 (1H (3″), ddq, J=14.0, 7.1, 7.1 Hz), 1.60 (2H (3′), m), 1.71 (1H (3″), ddq, J=14.0, 7.5, 7.5 Hz), 1.75 (3H (19), dd, J=2.9, 1.3 Hz), 1.90 (3H (11), dq, J=10.1, 6.5 Hz), 2.18 (1H (20-OH), m, J=6.8, 4.7 Hz), 2.28 (2H (2′), m, J=11.4, 7.4 Hz), 2.36 (2H (2″), sxt, J=7.3 Hz), 3.15 (1H (8), d, J=6.8 Hz), 3.26 (1H (7), s), 3.57 (1H (4-OH), d, J=1.0 Hz), 3.78 (1H (20), dd, J=12.5, 4.2 Hz), 3.86 (1H (20), dd, J=12.5, 6.8 Hz), 3.87 (1H (5-OH), d, J=3.1 Hz), 4.05 (1H (10), m, J=2.6 Hz), 4.21 (1H (5), d, J=2.6 Hz), 5.37 (1H (12), d, J=9.9 Hz), 5.98 (1H (9-OH), br.s.), 7.71 (1H (1), dd, J=2.6, 1.6 Hz).
$^{13}$C NMR (125 MHz, CDCl$_3$) δ ppm: 9.7 (19), 11.6 (4″), 14.1 (14′), 15.1 (18), 16.1 (5″), 17.2 (16), 22.7 (13′), 23.7 (17), 25.2 (2′), 26.2 (3″), 26.6 (15), 29.0 (5′), 29.3 (4′), 29.3 (4′), 29.5 (6′), 29.6 (8′), 29.6 (9′), 29.6 (10′), 29.7 (11′), 31.9 (12′), 34.6 (2′), 36.0 (8), 36.1 (14), 41.2 (2″), 45.6 (11), 48.9 (10), 61.7 (6), 64.5 (20), 65.2 (7), 65.5 (13), 71.6 (5), 72.4 (4), 76.5 (12), 77.2 (9), 133.5 (2), 164.7 (1), 173.3 (1′), 178.8 (1″), 209.9 (3).

Compound 52

$^1$H NMR (500 MHz, CDCl$_3$) δ ppm: 0.85 (3H (18), d, J=6.8 Hz), 0.90 (3H (4′), t, J=7.5 Hz), 1.11 (3H (5′), d, J=7.3 Hz), 1.19 (3H (16), s), 1.21 (3H (17), s), 1.31 (1H (14), d, J=6.8 Hz), 1.44-1.56 (1H (3′), m), 1.58-1.67 (1H (3), m), 1.74 (3H (19), dd, J=2.9, 1.3 Hz), 1.88-1.96 (1H (11), m), 2.08 (3H (2″), s), 2.33-2.43 (2H (2′), m), 3.15 (1H (8), d, J=6.2 Hz), 3.25 (1H (7), s), 3.59 (1H (4-OH), br.s.), 3.78 (1H (20), d, J=13.0 Hz), 3.85 (1H (20), d, J=12.5 Hz), 4.05 (1H (10), t, J=2.9 Hz), 4.21 (1H (5), s), 5.38 (1H (12), d, J=10.4 Hz), 5.74 (1H (9-OH), br.s.), 7.71 (1H (1), dd, J=2.3, 1.3 Hz).
$^{13}$C NMR (125 MHz, CDCl$_3$) δ ppm: 9.7 (19), 11.3 (4′), 15.0 (18), 16.5 (5′), 17.0 (16), 21.0 (2″), 23.6 (17), 26.1 (15), 26.9 (3′), 35.7 (14), 35.9 (8), 41.2 (2′), 45.3 (11), 48.9 (10), 61.7 (6), 64.5 (20), 65.2 (7), 65.8 (13), 71.5 (5), 72.4 (4), 76.2 (12), 76.9 (9), 133.5 (2), 164.6 (1), 173.6 (1″), 176.4 (1′), 209.9 (3).

Compound 53

$^1$H NMR (500 MHz, CDCl$_3$) δ ppm: 0.88 (3H (6′), m, J=7.3 Hz), 1.06 (3H (18), d, J=6.2 Hz), 1.18 (3H (16), s), 1.25 (3H (17), s), 1.25 (1H (14), d, J=7.3 Hz), 1.27-1.33 (4H (4′, 5′), m), 1.59-1.65 (2H (3′), m), 1.74-1.80 (1H (11), m), 1.76 (3H (19), dd, J=2.9, 1.3 Hz), 2.23 (1H (20-OH), t, J=6.2), 2.35 (2H (2′), td, J=7.5, 1.6 Hz), 3.06 (1H (8), d, J=7.3 Hz), 3.26 (1H (7), s), 3.57 (1H (4-OH), s), 3.77 (1H (10), t, J=2.6 Hz), 3.81 (2H (20), dd, J=7.3, 4.7 Hz), 3.94 (1H (12), dd, J=9.1, 1.3 Hz), 4.2 (1H (5), s), 7.69, (1H (1), dd, J=2.3, 1.3 Hz).
$^{13}$C NMR (125 MHz, CDCl$_3$) δ ppm: 9.8 (19), 13.9 (6′), 16.3 (18), 17.2 (16), 22.3 (5′), 23.3 (17), 24.5 (3′), 28.0 (15), 31.3 (4′), 34.0 (2′), 34.8 (14), 36.5 (8), 47.2 (11), 50.8 (10), 62.5 (6), 65.0 (20), 66.0 (7), 68.6 (13), 71.4 (5), 72.1 (4), 77.7 (9), 78.2 (12), 134.0 (2), 163.7 (1), 177.3 (1′), 209.6 (3).

Compound 60

HPLC: Kinetex CIS column 4.6 mm, 0.8 mL/min, methanol-water (70:30). Retention time: 10.9 minutes.

Examples of In Vitro Effects on Cell Types Involved in Wound Healing

Example 4: Scratch Closure and Fibroblast Migration In Vitro

The ability of early passage neonatal foreskin fibroblasts (NFF) cultured in RPMI 1640—10% foetal calf serum to migrate across a scratch wound made in a confluent monolayer following treatment with purified compounds or plant extracts was determined using one or more of the following three methods.

Method 1

Cells were seeded in 16-mm diameter wells (24-well plates), allowed to become confluent and 2 scratches made in each well using a sterile plastic pipette tip. The medium was removed, the wells washed with phosphate-buffered saline pH 7.2 (PBS) to remove dislodged cells, fresh medium added followed by serial 10-fold dilutions of pure compound or plant extract (2 µL). Incubation was continued for 16 to 30 hr. The experiment was terminated when the scratch edges of untreated cultures had closed approximately 25% of the initial gap. The monolayers were washed with PBS, fixed with ethanol and stained with 0.05% crystal violet. Photomicrographs of each well (EVOS microscope) were printed and each scratch measured at 3 places to determine the mean width. Accelerated wound closure was considered to be significant if the remaining gap was <40% of the gap of the untreated controls.

Method 2

Cells were seeded in 6 mm wells (96-well plates) or 16 mm (24-well plates), with 2 to 6 replicate wells/dilution, and treated as in Method 1. Immediately after treatment the scratch edges were outlined on the underside of the well with a fine point felt pen. After fixing and staining, migration was assessed under the microscope with the aid of a graticule, scoring migration as 0, 25, 50, 75 or 100% (total closure) of the initial width. Accelerated wound closure was considered to be significant if mean quartile of replicates was less than that of untreated controls ($p<0.05$, t-test). In addition, "wound" areas were created by seeding cells in the presence of 3 mm stainless steel pins (96-well plate), or by inserting flat-edged Teflon rings. These devices were removed after overnight incubation of the NFF cells.

Method 3

Cells were seeded and treated in 96-well plates as in Method 2 (5 replicate wells per dilution), except that the scratches were made in one action with a tool having 96, 1 mm thick teflon coated pins (Essen Bioscience Woundmaker). The plate was then placed in a 37° C. 5% $CO_2$ humidified atmosphere in an IncuCyte FLR instrument programmed to photograph each well under phase contrast at 3 hr intervals for 42 hours. The software determined the initial scratch boundaries and their rate of closure. Accelerated wound closure was considered to be significant if the initial rate of closure was >10% of the untreated controls.

The results are shown in Tables 7 to 9.

TABLE 7

Rates of Scratch Closure in human neonatal fibroblasts following treatment with pure compounds.

| | Method 1 | | Method 2 | | Method 3 | |
| --- | --- | --- | --- | --- | --- | --- |
| Compound | Test Conc (ng/mL) | % closure compared to control | Test Conc (ng/mL) | % closure compared to control | Test Conc (ng/mL) | % closure compared to control |
| 1 | 30 | 166 | 200 | 180 | 30 | 150 |
| 1 | 100 | 146 | | | 100 | 160 |
| 2 | 30 | 130 | | | 30 | 147 |
| 2 | 100 | 129 | | | | |
| 3 | | | | | 200 | 270 |
| 5 | | | | | 30 | 209 |
| 5 | | | | | 200 | 300 |
| 8 | | | 200 | 190 | | |
| 11 | | | | | 200 | 270 |
| 18 | | | | | 200 | 220 |
| 27 | | | 1000 | 158 | 2000 | 130 |
| 28 | | | | | 200 | 140 |
| 21 | | | | | 200 | 200 |
| 22 | | | | | 200 | 400 |
| 23 | | | | | 200 | 130 |

Grey shading with bold indicates scratch closure rate is significantly higher than control treatment All pure compounds were demonstrated to have significantly enhanced rates of scratch closure compared to vehicle-only control treatments.

TABLE 8

Rates of Scratch Closure in human neonatal fibroblasts following treatment with unfractionated ethanolic extracts of different plant parts of Fontainea picrosperma

| | Method 1 | | Method 2 | | Method 3 | |
| --- | --- | --- | --- | --- | --- | --- |
| Plant Part | Extract dilution | % closure compared to control | Extract dilution | % closure compared to control | Extract dilution | % closure compared to control |
| leaf | 5000 | 268 | 5000 | 300 | 5000 | 220 |
| stem | 5000 | 367 | | | | |
| bark | 500 | 397 | 500 | 200 | | |
| endosperm | 500 | 128 | 500 | 270 | | |
| exocarp | 500 | 167 | | | | |
| Immature fruit | $5 \times 10^4$ | 300 | | | | |

Grey shading with bold indicates scratch closure rate is significantly higher than control treatment Ethanolic crude extracts of all plant parts of Fontainea picrosperma that were tested had significantly enhanced rates of scratch closure compared to vehicle-only control treatment.

TABLE 9

Rates of Scratch Closure in human neonatal fibroblasts following treatment with unfractionated ethanolic extracts of different plant parts of three different plant species

| | Method 1 | | Method 2 | | Method 3 | |
| --- | --- | --- | --- | --- | --- | --- |
| Plant part | Extract dilution | % closure compared to control | Extract dilution | % closure compared to control | Extract dilution | % closure compared to control |
| *Fontainea australis* | | | | | | |
| leaf | | | | | 500 | 163 |
| stem | | | | | 5000 | 203 |
| *Fontainea rostrata* | | | | | | |
| leaf | 500 | 101 | | | 500 | 141 |
| *Hylandia dockrillii* | | | | | | |
| leaf | 5000 | 187 | | | | |
| stem | 500 | 390 | | | 500 | 129 |
| bark | 500 | 192 | 5000 | 121 | | |
| fruit | 500 | 385 | | | | |

Grey shading with bold indicates scratch closure rate is significantly higher than control treatment Extracts from plant parts of two other species of Fontainea, F. australis and F. rostrata, and the closely related species Hylandia dockrillii demonstrated significantly increased rates of scratch closure compared to the vehicle-only control treatment.

Figure 2:
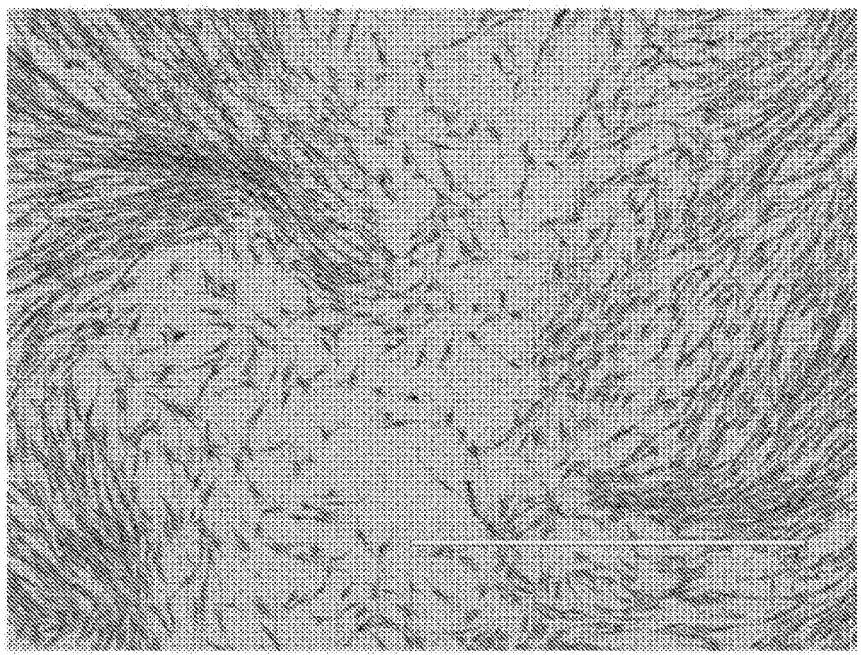
FIG. 2 is a photographic representation of scratch closure in human neonatal fibroblast cells treated with 30 ng/mL Compound 1, 24 hours post scratch.

Additionally, observations of test plates under the microscope (Method 1) suggested that the fibroblasts displayed a gross difference in staining pattern following treatment with Compound 1. Closer investigation revealed this was due to the cells apparently growing in a muitilayered fashion, potentially indicating a loss of contact inhibition, an increase in proliferation, or remodelling capability. Examples of scratch closure in the control and Compound 1 treatment at 24 hours post scratch are illustrated in FIGS. 1 and 2 respectively.

Example 5: Matrigel Invasion Assay for Migratory Ability of Human Neonatal Fibroblasts Matrigel invasion chambers provide cells with the conditions that allow assessment of their invasive property in vitro. The Matrigel invasion chambers consists of a cell culture companion plate with cell culture inserts containing an 8 micron pore size PET membrane with a thin layer of Matrigel Basement Membrane Matrix. The Matrigel matrix serves as a reconstituted basement membrane in vitro. The layer occludes the pores of the membrane, blocking non-invasive cells from migrating through the membrane. In contrast, invasive cells are able to detach themselves from and invade through the Matrigel matrix and the 8 micron membrane pores. The membrane may be processed for light and electron microscopy and can be easily removed after staining.

The chambers were used according to the manufacturer's instructions, as described below in two studies, to assess the effects of Compounds 1, 2, 5 and 42 on migration of human neonatal fibroblasts. The first study assessed effects of three concentrations (0, 10 and 30 ng/mL) of Compound 1 on neonatal fibroblasts in wells containing media with 10% foetal calf serum. The second study used two concentrations (0 and 30 ng/mL) for each of Compounds 1, 2, 5 and 42 to examine effects on migration of neonatal fibroblasts starved for 2 days prior to treatment and then transferred to media with 1% foetal calf serum.

Rehydration

The package containing the chambers was removed from −20° C. storage and allowed to come to room temperature. Warm (37° C.) bicarbonate based culture medium was added to the interior of the inserts (500 µL) and bottom of wells (750 µL). The chambers containing the Matrigel were allowed to rehydrate for 2 hours in humidified tissue culture incubator, 37° C., 5% $CO_2$ atmosphere. After rehydration, the medium was carefully removed by aspiration without disturbing the layer of Matrigel™ Matrix on the membrane.

Invasion Studies

Cells were harvested, and resuspended at 20,000 cells per mL. A total of 250 µL of the cell suspension was placed into the interior of the insert (5,000 cells). An extra 250 µL media containing the respective Compounds was then added to the interior of the insert to give the desired final concentrations for each of the two studies. A total of 750 µL of media containing appropriate concentrations of each compound in each treatment were placed in the well under the appropriate insert. The Matrigel chambers were then incubated for 24 hours in a humidified tissue culture incubator, at 37° C., 5% $CO_2$ atmosphere.

Measurement of Cell Invasion

Non-invading cells were removed from the upper surface of the membrane by "scrubbing". A cotton tipped swab was dipped into the insert after removal of the media, and firm pressure applied while the tip was moved over the membrane surface. The scrubbing was repeated with a second swab moistened with PBS. Cells that had invaded to the external surface of the insert were then fixed by placing in 500 µL of 100% methanol for at least 5 mins. Inserts were then transferred to a companion plate containing 500 µL of 0.1% crystal violet in methanol, and stained for at least 15 mins. Inserts were destained by passage through 3 companion plates containing 500 µL water, before being air dried.

The following day, the membrane was removed from the insert housing by inverting the insert and inserting the tip of a sharp scalpel blade through the membrane at the edge adjacent to the housing wall. The insert housing was rotated against the stationary blade and the membrane was released. The membrane was picked out of the housing with forceps, and placed face down on 10 µL of Kaiser's glycerol solution and covered with a coverslip. Slides were allowed to dry overnight, before counting of the invading cells.

Results

Figure 3:
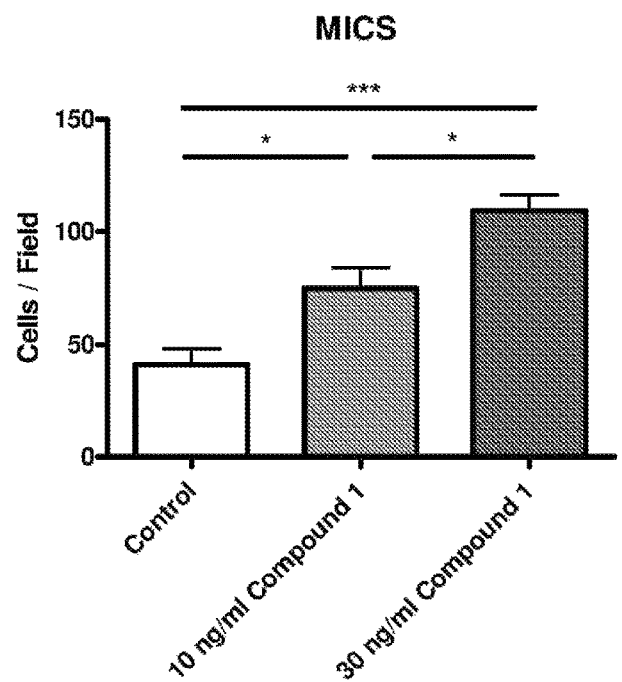
FIG. 3 is a graphical representation of matrigel invasion assay of human neonatal fibroblast cells treated with 10 ng/mL or 30 ng/mL Compound 1 compared to vehicle-only control. Cells were counted after 24 hours incubation. *$p<0.05$; ***$p<0.001$.
Figure 4:
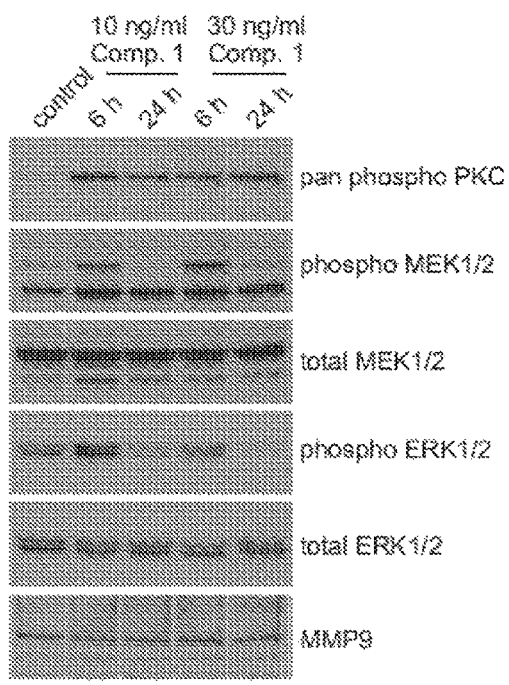
FIG. 4 is a Western blot analysis of human neonatal fibroblast cells treated with Compound 1 and shows activation and subsequent downregulation of key signalling molecules involved in wound repair and healing.

In the first study, fibroblasts treated with either 10 or 30 ng/mL Compound 1 showed increased migratory ability in the Matrigel invasion chamber system compared to cells treated with vehicle alone (FIG. 3). The second study confirmed the results of the first study with Compound 1 and demonstrated similar levels of enhanced in migratory ability for Compounds 2, 5 and 42 (Table 10).

TABLE 10

Matrigel invasion assay of human neonatal fibroblast cells treated with 30 ng/mL of each compound. Data are expressed as a % increase in membrane invasion compared to vehicle-only control, plus or minus standard deviations from two replicate experiments. Cells were counted after 24 hrs incubation.

| Compound | Cell count as % of control (Control = no compounds added) |
|---|---|
| 1 | 356 ± 141 |
| 2 | 366 ± 122 |
| 5 | 218 ± 21 |
| 42 | 350 ± 101 |

Example 6: Scratch Repopulation and Closure with Immortalised Human Keratinocytes (HaCaT) In Vitro The ability of immortalised human keratinocyte cells (HaCaT) to migrate across a scratch wound made in a confluent monolayer following treatment with either Compound 1 or Compound 37 was determined by the following method.

Trypsinised HaCaT cells were seeded at a cell density of $7.4 \times 10^4$ cells/mL in 24-well BD Falcon flat-bottomed, tissue culture plates (VWR International, UK) in 1 mL Dulbecco's Modified Eagle Medium (DMEM), supplemented with L-glutamine (2 mM), antibiotics (100 U/mL penicillin G sodium, 100 µg/mL streptomycin sulphate and 0.25 µg/mL amphotericin B); and 10% foetal calf serum (all Invitrogen Ltd., UK) to give a cell density of $7.4 \times 10^4$ cells seeded in each well. The cells were then maintained at 37° C. in a 5% $CO_2$/95% air atmosphere overnight. The following morning, the 10% foetal calf serum-containing DMEM was replaced with serum-tree DMEM and the HaCaT cells were subsequently serum-starved in DMEM for 48 hr.

After 48 hr, the serum-free DMEM was removed and a single scratch 'wound' made with a sterile pipette across each cell layer. Following washing twice in 1 mL PBS, Compound 1- or Compound 37-containing medium (1 mL) was added to each well. This medium consisted of DMEM, supplemented with L-glutamine (2 mM), antibiotics (as above) and 1% foetal calf serum, in addition to Compound 1 or Compound 37 at final concentrations of 0, 0.001, 0.01, 0.1, 1.0, 10 or 100 µg/mL. There were three replicate wells per concentration for each compound.

The HaCaT cultures were maintained at 37° C. in a 5% $CO_2$/95% air atmosphere and the repopulation of the denuded 'wound' areas monitored by Time-Lapse Confocal Microscopy (Leica TCS SP5 Confocal Microscope, Leica Microsystems UK Ltd., UK) at 100× magnification, with digital images captured at fixed positions every 20 min over a 48 h period. The digital image sequences were exported and prepared as .avi movie files, using LAS AF Software (Leica Microsystems). The rates of HaCaT wound closure in vitro were quantified using ImageJ Software (ImageJ 1.37v; http://rsb.info.nih.gov/ij/). The data was analysed by One Way Analysis of Variance with post-test Tukey analysis. Each experiment was performed on 3 separate occasions.

At 48 hrs after application, Compound 1 significantly increased the rate of scratch closure (p<0.01) compared to the control treatment at concentrations of 0.001, 0.01 and 0.1 ng/ml (Table 11). At 48 hours Compound 37 also increased the rate of scratch closure (p<0.01) compared to the control treatment at concentrations of 0.001, 0.01, 0.1 and 1.0 µg/ml (Table 11).

TABLE 11

Extent of scratch repopulation and closure by immortalised human keratinocyte (HaCaT) cells at 48 hours after treatment over a range of concentrations of Compound 1 and Compound 37. Data are for % of scratch wound area remaining open after treatment (±standard errors).

| Compound | Concentration of compound (µg compound/ml growth medium) | | | | | |
|---|---|---|---|---|---|---|
| | 0 | 0.001 | 0.01 | 0.1 | 1.0 | 10 |
| 1 | 43.8 ± 3.6 | 8.6 ± 9.4 | 19.7 ± 9.3 | 21.4 ± 5.8 | 35.4 ± 7.9 | 45.5 ± 7.3 |
| 37 | 49.5 ± 5.4 | 4.3 ± 4.1 | 0.9 ± 1.5 | 2.2 ± 3.4 | 30.0 ± 5.3 | 37.1 ± 7.1 |

To determine whether the effects of Compound 1 and Compound 37 in enhancing scratch repopulation and closure as shown in Table 11 were mediated by cell proliferation or migration two further experiments were conducted. The first of these experiments addressed migration aspects and repeated the scratch repopulation study but with the addition of 1 µg/mL of Mitomycin C to the medium at the same time that the compounds were applied. Mitomycin C is known to inhibit cellular proliferation, including that of HaCaT cells; and was determined to not be cytotoxic in the culture system at the 1 µg/mL concentration. The results of this migration study found enhanced (p<0.05) scratch repopulation and closure at concentrations between 0.001 and 1.0 µg/mL for both Compound 1 and Compound 37.

The proliferation experiment assessed the effects of the two compounds on HaCaT proliferation (as measured by MTT) in the culture system at 4 time periods (24, 48, 120 and 168 hr). Both Compounds 1 and 37 had a significant effect (p<0.01) in increasing proliferation of HaCaT cell across a range concentrations between 0.001 and 10 µg/mL in comparison to the control treatment with no compound added.

These results demonstrate that both proliferation and enhanced cell migration are involved in the scratch repopulation and closure process with Compounds 1 and 37.

Example 7: Differentiation of Monocytes into Macrophages by the Compounds

Macrophages play numerous roles in wound healing, including clearing cellular debris and necrotic tissue in the early, inflammatory stage followed by the support of cell proliferation and tissue restoration during the later stages of healing. The M1 phenotype is considered to be associated with the early inflammatory stage and the M2 phenotype with the healing stage.

To determine potential effects of of Compound 1 and Fifteen other epoxy-tigliane compounds in the array on monocyte differentiation, human peripheral blood mononuclear cells (PBMCs) were isolated by Ficoll-Paque sedimentation of heparinised blood from a 72-year old male human donor, and plated at 100,000 cells/well in RPMI-1640 10% FCS. Duplicate wells were treated with 10-fold dilutions of the compounds and incubated at 37° C. for 4 days. The wells were scored visually for cell attachment and morphology, then washed twice with PBS, stained with sulfurhodamine and the incorporate stain quantitated in an ELISA reader. The plates were then washed with water and stained with 1% crystal violet in methanol for photography and scoring of adherent cell morphology.

The results from a dose-response experiment with human PBMCs (Table 12) showed that all sixteen epoxy-tigliane compounds tested differentiated peripheral blood monocytes into macrophages at ng concentrations, as judged by adherence and morphology which was a mixture of dendritic cells typical of the M2 phenotype, and rounded cells typical of the M1 phenotype.

TABLE 12

Endpoint concentrations in dilution series for induction of macrophage phenotype in human peripheral blood monocytes by epoxy-tigliane compounds in the array.

| Compound | Differentiation endpoint (ng/mL) |
|---|---|
| 1 | 1 |
| 2 | 1 |
| 3 | 10 |
| 5 | 1 |
| 8 | 10 |
| 21 | 10 |
| 22 | 100 |
| 23 | 1 |
| 24 | 1 |
| 41 | 0.1 |
| 42 | 1 |
| 49 | 1 |
| 50 | 1 |
| 51 | 1 |
| 52 | 10 |
| 53 | 100 |

Example 8: Effects of Compounds 1 and 37 on Differentiation of Adult Dermal Fibroblasts into Myofibroblasts Fibroblasts play a central in the wound healing process and when activated, they differentiate into a myofibroblastic phenotype which is characterised by the expression of α-smooth muscle actin (α-SMA). While myofibroblasts contribute to tissue repair and closure of wounds, their over-expression is associated with impaired healing and excessive scarring.

The effects of Compounds 1 and 37 on dermal fibroblast differentiation to myofibroblasts was examined by the extent of α-SMA expression by TGF-$\beta_1$-stimulated dermal fibroblasts.

Methods

Following trypsinization, fibroblasts were seeded in 8-well, Permanoxchamber slides (VWR International) in DMEM medium, containing antibiotics, 2 mM L-glutamine and 10% foetal calf serum (250 µL, all purchased from Invitrogen); at a cell density of $2.5 \times 10^4$ cells/well and maintained at 37° C. in 5% $CO_2$/95% air for 48 h.

At 48 hr, fibroblasts were growth-arrested in serum-free DMEM for 48 hr and then replaced with serum-free DMEM (250 µL), containing Compounds 1 or 37 at concentrations of 0, 0.001, 0.01, 0.1, 1.0 and 10.0 µg/mL (3 wells/concentration/compound) and TGF-$\beta_1$ (10 ng/ml, Peprotech). Fibroblasts were maintained at 37° C. in 5% $CO_2$/95% air for 72 hr.

At 72 hr, chamber slide wells were washed with PBS (×1, 250 µL) and fixed in 4% paraformaldehyde (100 µL/well) for 10 min. The chamber slide wells were then washed again with PBS (×1, 250 µl), treated with 0.1% Triton X-100 in PBS (100 µL, Sigma) for 5 min and re-washed with PBS (×1, 250 µL). Wells were blocked with 1% BSA in PBS (250 µL, Sigma) for 1 h and washed (×3) in 0.1% BSA/PBS.

Wells were incubated with monoclonal mouse anti-human α-SMA, clone 1A4 (1:100, 150 ul, Sigma) at 4° C. overnight, washed (×6) in 0.1% BSA/PBS and incubated with Alexa Fluor 488 goat anti-mouse IgG antibody (1:1000, 250 µL, Invitrogen), at room temperature for 1 h, under darkness. Chamber slides were washed (×6) in 0.1% BSA/PBS and counterstained with Hoescht 33258 solution for 30 min. under darkness (1:2000, 250 µL, Sigma). Chamber were subsequently removed for slides and treated with Fluorsave (Santa Cruz) for 10 min under darkness. Slides were viewed by fluorescence microscopy (Leica Microsystem), with digital images being captured at ×200 magnification. Digital images were processed using HC Image J Software.

Results

Figure 5:
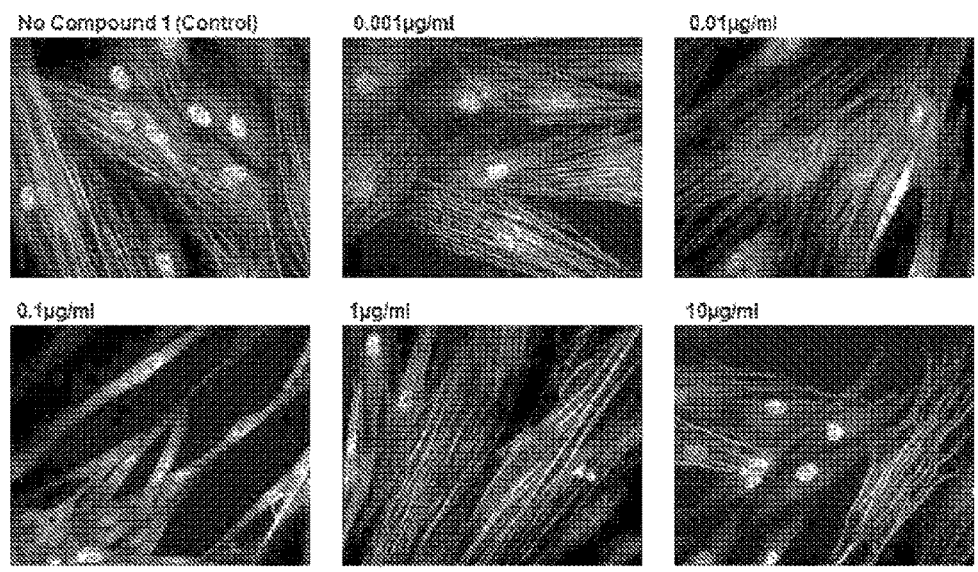
FIG. 5 is a photographic representation of the effects of exposure of fibroblasts (cultured in the presence of TGF-β1) to a range of concentrations of Compound 1 on the differentiation to myofibroblasts, characterised by the increased expression of α-smooth muscle actin and stress fibre formation.

In the control treatment with TGF-$\mu_1$ but no Compounds added, the adult dermal fibroblasts differentiated into myofibroblasts, typically characterized by increased α-SMA expression, α-SMA stress fibre assembly and the overall development of an enlarged, polygonal cellular morphology. In contrast, exposure of adult dermal fibroblasts treated with TGF-$\beta_1$ to Compound 1 and Compound 37 affected differentiation into myofibroblasts in a concentration-dependent manner. In the case of Compound 1 at a concentration of 0.1 µg/mL, the fibroblast cultures lacked the α-SMA stress fibre formation and the typical polygonal cellular morphology, representative of myofibroblast differentiation (FIG. 5). With Compound 37 there was a disruptive effect on α-SMA stress fibre formation and polygonal morphology development at a 10 µg/mL concentration (FIG. 6).

Figure 6:
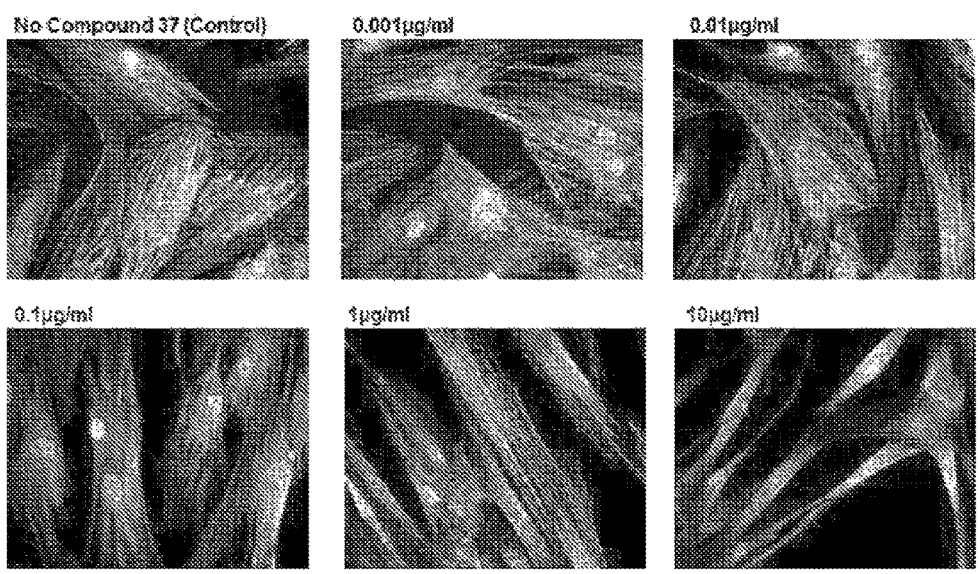
FIG. 6 is a photographic representation of the effects of exposure of fibroblasts (cultured in the presence of TGF-β1) to a range of concentrations of Compound 37 on the differentiation to myofibroblasts, characterised by the increased expression of α-smooth muscle actin and stress fibre formation.

Furthermore, there appear to be other subtle alterations in myofibroblast morphology across the range of concentrations between 1 and 10 µg/mL of Compound 1 and between 0.1 to 1.0 µg/mL for Compound 37 (FIGS. 5 and 6).

Specific effects of the compounds on fibroblast/myofibroblast differentiation may be relevant to the minimal scar formation observed in wounds treated in vivo with Compound 1 (Examples 16 and 17).

Example 9: Induction of Reactive Oxygen Burst by Neutrophils in Response to Compound 1

Neutrophils are dedicated phagocytic cells of the innate immune system and their influx and activation is essential for the clearance of bacteria, fungi and cellular debris during early stages of wound healing. The broad antimicrobial activity of neutrophils is based on several strategies including bursts of reactive oxygen species (ROS).

A study was undertaken to assess the potential effects of Compound 1 in inducing reactive oxygen burst by neutrophils.

Neutrophils were isolated from fresh blood of a healthy human donor by lysis of a red blood cell pellet that had been obtained by Ficoll-Paque sedimentation. The neutrophils (~$4 \times 10^6$ cells/ml) were incubated with 10 µg/ml dihydroethidium (DHE) (Sigma-Aldrich) in complete culture medium at 37° C. for 15 min alongside an aliquot of unstained cells to be tested as unstained control. This incubation was followed by treatment with Compound 1 at a range of concentrations (0, 1 ng/ml, 10 ng/ml, 100 ng/ml, 1 µg/ml, 10 µg/ml, 100 µg/ml) for 15 min. The generation of reactive oxygen species following incubation was determined using a FACS Canto flow cytometer to measure fluorescence due to oxidation of DHE to the ethidium ion.

This study found no production of ROS in the control treatment without Compound 1 present. In contrast, Compound 1 induced the significant production of reactive oxygen species (ROS) in a dose-dependent manner, with ROS production increasing with concentrations of Compound 1.

Examples of Effects of Compounds on Proteins, Genes and Cytokines Relevant to Improved Wound Healing Outcomes Example 10: Molecular Analysis of Human Neonatal Fibroblasts Treated with Compounds 1 and 42

The Western Blot method was used to identify effects of Compounds 1 and 42 on proteins relevant to would repair and healing in human neonatal fibroblast cells (NFFs). Two studies were conducted. In the first study, NFFs were treated with either 10 or 30 ng Compound 1/mL for 6 or 24 hours, before harvesting and protein extraction. In the second study NFFs were treated individually with 30 ng/mL concentrations of Compounds 1 and 42 respectively for 6 hours. The resulting lysates from both studies were subjected to western blot analysis, and probing with specific antibodies to key signalling molecules involved in wound repair and healing.

Preparation of Protein Samples for Western Blotting

The medium from adherent human neonatal fibroblasts grown in 75 $cm^2$ plates was removed and the cells were washed twice in ice cold PBS. The attached cells were harvested in 10 mL of ice cold PBS using a cell scraper (Costar®, Corning) pelleted by centrifugation for 5 min (1,500 rpm, RTemp), resuspended in 1 mL of ice-cold PBS, and transferred to a 1.5 mL microfuge tube. The cells were collected by centrifugation (13,200 rpm. RTemp, 2 s), the PBS removed and the pellets stored at −20° C. until required.

The frozen pellets were thawed on ice, and resuspended in a volume of cell lysis buffer 3-4 times the volume of the pellet by pipetting up and down. The cell suspension was sonicated 60 s at 4° C. and centrifuged for 20 min (13,200 rpm, 4° C.) and the interphase containing the protein transferred to a fresh 1.5 ml microfuge tube. The protein was stored at −20° C.

Determination of Protein Concentration

Protein concentrations were determined using the BCA Protein Assay kit (Pierce). This method is based on the reduction of $Cu^{2+}$ to $Cu^{1+}$ by protein in an alkaline solution. The $Cu^{1+}$ formed is subsequently chelated with bicinchronic acid (BCA) forming a purple reaction product.

Protein samples were diluted 1/10 and 1/20 (v/v) in MilliQ water and 10 µL was plated out in duplicate in a flat-bottomed 96-well plate (Costar®, Corning). Stock solutions of bovine serum albumin (BSA) were prepared at 100, 200, 400, 600, 1,000, and 1,200 µg/mL and 10 µL/well plated out in duplicate and assayed alongside the samples. The BCA working reagent was prepared by mixing 50 parts of reagent A with 1 part of reagent B and aliquoting 100 µL to each well. The plate was incubated at 37° C. for 30-45 min to allow the reaction to occur. The raw absorbances were read at A590 nm on a microplate reader (VERSAmax, Molecular Devices) and a standard curve produced using SOFTmax PRO software (Molecular Devices). Concentrations of unknown samples were estimated from the curve.

SDS Polyacrylamide Gel Electrophoresis (SDS-PAGE)

Protein samples were prepared by mixing with an appropriate volume of 2×SDS loading buffer and denatured by heating for 10 min at 70° C. The SDS-PAGE gel was performed using the Mini-Protean II dual slab gel apparatus (Bio-Rad Laboratories) as described by Laemmli (6). The resolving gel consisted of 0.275 M Tris-HCl (pH 8.8), 0.1% (w/v) SDS, 0.05% (w/v) freshly made-up ammonium persulphate, 1% (v/v) TEMED and between 7.5-12% (w/v) acrylamide/bisacrylamide (29:1). The solution was made up to 5 mL in MilliQ $H_2O$, and allowed to set for at least 30 min (RTemp) while overlayed with water-saturated butanol. Before pouring the stacking gel, the water-saturated butanol was tipped off. The stacking gel consisted of 0.125 M Tris-HCl (pH 6.8), 0.1% (w/v) SDS, 0.05% (w/v) freshly made-up ammonium persulphate, 0.1% (v/v) TEMED and 4% (w/v) acrylamide/bisacrylamide (29:1). The solution was made to 2.5 mL per gel in MilliQ $H_2O$, poured on top of the resolving gel and allowed set with a 10-well comb (Bio-Rad Laboratories) for at least 30 min. Electrophoresis was performed for approximately 1 h or until the dye from had run off the bottom of the gel (200 V, RTemp) in 1×SDS running buffer.

Western Transfer

Following SDS-PAGE electrophoresis the gel plates were carefully separated, the stacking gel cut off and transferred to the Mini Trans-Blot Cell (Bio-Rad Laboratories). A "transfer sandwich" was assembled as follows: a porous sponge, two sheets of blotting (Whatmann) paper, nitrocellulose membrane, the gel, two more pieces of blotting of blotting paper and another porous sponge and inserted into the transfer apparatus. The sponges, membrane and blotting paper were pre-wet in cold electroblot buffer and care was taken to prevent any air bubbles to form as this would result in inconsistent transfer of proteins. The proteins were transferred at 100 V for 1 h (constant voltage) in ice-cold transfer buffer at 4° C. with the nitrocellulose membrane (Hybond™-C, Amersham Biosciences) closer to the anionic side, and an ice pack and magnetic stirrer added.

Probing Protein Membranes

Once transferred, the membrane was incubated in 5% (w/v) Blotto in 0.1% (v/v) Tween 20/TBS at RTemp for at least 30 min with gentle orbital shaking to block non-specific binding sites. The primary antibody was diluted in 5% (w/v) BSA as recommended by the manufacturer (see Table 13 below) to a final volume of 2 mL. A plastic envelope containing the membrane and antibody was made and heat-sealed, removing as many air-bubbles possible. The envelopes were rotated on a custom made rotor overnight (approximately 16 h) at 4° C.

The membrane was removed from the bag, placed in a plastic tray with 0.1% (v/v) Tween 20/TBS and washed four times at room temperature with vigorous orbital shaking for 15 min per wash. The appropriate secondary antibody conjugated to horseradish peroxidase (HRP) was probed to the membrane by diluting it 1/1,000 in 5% (w/v) Blotto in 0.1% (v/v) Tween 20/TBS and placing it in a fresh plastic envelope which was rotated at room temperature for 2 hr.

Immuno-Detection of Proteins

In order to remove any unbound or non-specifically bound antibody, the membrane was washed in 0.1%) (v/v) Tween 20/TBS/ at room temperature four times for 15 min each. The Western Lighting™ Chemiluminescence Reagent Plus (PerkinElmer Life Sciences) was used to generate detectable signal from secondary antibodies labelled with HRP. The reagent relies on the oxidative degradation of luminal catalysed by HRP, resulting in the emission of light which is detectable 420 nm and can be captured on film. Equal volumes from bottle 1 and bottle 2 were mixed just prior to detection. A total volume of 2 mL per membrane was applied and incubated at room temperature for 1 min. Care was taken to ensure that the whole membrane was equally exposed. The membrane was removed, dried quickly on some blotting paper, inserted between two pieces of polypropylene sheet protectors into a film cassette (Hypercassette™, Amersham Biosciences) and exposed to piece of film (SuperRX, Fujifilm). An initial exposure of 2 min was used to judge optimal detection time. The film was developed in a Kodak Image Station (Kodak).

TABLE 13

Antibodies used in this study were:

| Antibody | Host | Dilution Used | Manufacturer |
|---|---|---|---|
| Anti-pan phospho PKC | Rabbit | 1:1,000 | Cell Signalling |
| Anti-Phospho-ERK (Thr202/Tyr204) | Rabbit | 1:1,000 | Cell Signalling |
| Anti-ERK | Rabbit | 1:1,000 | Cell Signalling |
| Anti-Phospho-MEK1/2 (Ser217/221) | Rabbit | 1:1,000 | Cell Signalling |
| Anti-MEK1/2 | Rabbit | 1:1,000 | Cell Signalling |
| Anti-MMP9 | Rabbit | 1:1,000 | Cell Signalling |
| Anti-Rabbit Ig HRP-Conjugated | Sheep | 1:1,000 | Cell Signalling |

In the first study with Compound 1, Western blot analysis a transient activation of both MEK1/2 and ERK1/2 following 6 hours of treatment with either 10 or 30 ng/mL of Compound 1, and a subsequent down-regulation of activation following 24 hours treatment. Activation of the MEK/ERK branch of the MAP Kinase pathway in known to influence the migratory phenotype of many cellular types, including fibroblasts. No difference in levels of MMP9 was detected.

Similar patterns of phosphorylation of phospho-ERK were found on Western Blots in the second study with 30 ng/mL concentrations of Compounds 1 and 42 on the NFFs.

Example 11: Effect of Compound 1 on Expression of Genes Involved in Wound Healing The effects of Compound 1 on expression of genes associated with wound healing were examined in two situations (a) human PBMCs and (b) mouse stroma of human tumour xenografts.

Materials and Methods

Human peripheral blood mononuclear cells (PBMCs) were isolated by Ficoll-Paque sedimentation of heparinised blood from a 68-year old male human donor, and cultured in RPMI-1640 10% PCS. Following treatment with Compound 1 at 30 ng/mL, the monolayer was washed once with phosphate buffered saline (PBS) and the cells harvested with sterile scrapers and stored as pellets at −80° C.

Mouse stroma in human tumour xenografts were obtained from mice in which the Sk-Mel-28 human melanoma cell line was injected subcutaneously into 2 sites on the flanks of each BALB/c Foxnlnu mouse ($2\times10^6$ cells/site) and allowed to grow to approximately 7 mm diameter. Each tumour was then injected with 50 µL of 20% propylene glycol containing 30 µg Compound 1 or with 50 µL of 20% propylene glycol. At different times after injection a mouse was euthanased and the tumours harvested, the skin covering removed, and the intact tumours stored at −80° C.

RNA was extracted from 30 mg of frozen tumour or $1\times107$ cells using the QiagenRNeasyPlus Mini Kit, according to manufacturer's instructions, then quantitated with a NanoDrop instrument and integrity confirmed on denaturing agarose gels bearing a 1 kb DNA marker and stained with ethidium bromide.

RNA Amplification and Labelling.

Approximately 500 ng of total unlabelled RNA was adjusted to a final volume of 11 µL with nuclease-free water. The RNA was incubated with 9 µL of the reverse transcriptase master mix (1 µL of T7 Oligo (dT) Primer, 2 µL of 10× first strand buffer, 4 µL of dNTP mix, 1 µL of RNase inhibitor and 1 µL of ArrayScript) at 42° C. for 2 hr. This was followed by the second strand cDNA synthesis step which involved a further incubation at 16° C. for 2 hr with 80 µL of the second strand master mix (63 µL nuclease-free water, 10 µL 10× second strand buffer. 4 µL dNTP mix, 2 µL DNA polymerase and 1 µL RNase H). The cDNA was purified by filtering through a cDNA Filter Cartridge with 250 µL of cDNA binding buffer and washing with 500 µL of the wash buffer provided in the kit. Purified cDNA was eluted with 20 µL of 55° C. nuclease-free water. Each cDNA sample was incubated with 7.5 µL of the IVT master mix (2.5 µL of T7 10× reaction buffer, 2.5 µL of T7 enzyme mix and 2.5 µL biotin-NTP mix) at 37° C. for 16 hr. The reaction was stopped with the addition of 75 µL of nuclease-free water to each cRNA sample. The biotinylated, amplified RNA was purified by filtering the cRNA samples through cRNA Filter Cartridges with 350 µL of cRNA binding buffer and 250 µL of 100% ethanol mixed together prior to loading onto the filters. The cRNA filter cartridges with attached RNA were then washed with 650 µL of wash buffer before eluting purified cRNA with 200 µL of 55° C. nuclear-free water.

Illumina Expression BeadChip Hybridization. The cRNA samples were heated at 65° C. for 5 min and collected by pulse centrifugation. After heating at 65 degrees for 5 min, approximately 750 ng of the cRNA sample was aliquoted into separate tubes to which were added ~5 µL of RNase-free water and 10 µL of Hyb Mix. Approximately 15 µL of the prepared cRNA mix was loaded onto the Illumina Expression BeadChips. Subsequent steps of hybridisation and washing were carried out according to the Whole-Genome Gene Expression Direct Hybridization Assay Guide supplied by Illumina.

The Human HT-12 v4 Expression BeadChips cover more than 47,000 transcripts and known splice variants across the human transcriptome. The MouseRef-8 v2.0 Expression BeadChips cover approximately 25,600 well-annotated RefSeq (Reference Sequence) transcripts, comprising over 19,000 unique genes.

Data analysis. BeadChips were read by the iScan System, and transferred via GenomeStudio into GeneSpring GX v12.5 (Agilent Technologies, Santa Clara, Calif., USA). The expression values were normalized using quantile normalization with default settings. The entities were filtered based on the detection score calculated by GenomeStudio where p≤0.05 was considered significant.

Wound Healing-Relevant Gene Expression Changes Induced in Human Pbmcs by Compound 1.

Human peripheral blood mononuclear cells (PBMCs) are rich in lymphocytes and macrophage precursors (monocytes) involved in the production of cytokines and tissue remodelling enzymes relevant to the wound healing process. Table 14 lists gene expression changes induced by 30 ng/mL Compound 1 that were >2 times higher or >2 times lower than control, untreated PBMCs, and had a known link with wound healing. Wound healing is a complex, multistage sequence in which processes such as inflammation subsequently need to be down-regulated. It should therefore be noted that the genes shown in Table 14 illustrate the range of relevant molecules regulated by Compound 1 in a mixed lymphoid population in vitro, without specifying the order of tissue-specific expression in vivo.

The genes included pro-inflammatory cytokines (IL-1α, IL-1β and IL-6) involved in protection from infection, cytokines to moderate the inflammatory response (IL-10 and IL-24), growth factors (GMCSF, CSF1 and HBEGF), and a range of chemokines and matrix metallopeptidases for tissue remodelling (the latter facilitated by down-regulation of TIMP2). Down regulation of THBS1, which suppresses granulation tissue formation, is also a positive factor in wound healing. Up-regulation of KLF10 should facilitate angiogenesis and is indicative of induction of TGF-β. Transglutaminases (TGM) stabilise proteins by cross linking them and have other beneficial effects in wound healing.

TABLE 14

Changes in expression of genes relevant to improved wound healing outcomes that are induced in human PBMCs by Compound 1

| Gene | Gene Name (*Homo sapiens*) | Time (h) | Fold change in expression | Direction of regulation |
|---|---|---|---|---|
| IL1α | Interleukin 1, alpha (IL1α), mRNA. | 24 | 14.6 | Up |
| IL1β | Interleukin 1, beta (IL1β), mRNA. | 24 | 15.4 | Up |
| IL6 | Interleukin 6 (Interferon 2, beta) (IL6), mRNA. | 24 | 33.1 | Up |
| IL10 | Interleukin 10 (IL10), mRNA. | 24 | 2.1 | Up |
| IL24 | Interleukin 24 (IL24), transcript variant 1, mRNA. | 24 | 4.6 | Up |
| GM-CSF | GM colony-stimulating factor (GM-CSF), mRNA | 4 | 4.3 | Up |
| | | 24 | 34.6 | Up |
| | | 96 | 6 | Up |

TABLE 14-continued

Changes in expression of genes relevant to improved wound healing outcomes that are induced in human PBMCs by Compound 1

| Gene | Gene Name (*Homo sapiens*) | Time (h) | Fold change in expression | Direction of regulation |
|---|---|---|---|---|
| CSF1 | Colony stimulating factor, transcript variant 4, mRNA. | 24 | 5.1 | Up |
| HBEGF | Heparin-binding EGF-like growth factor (HBEGF), mRNA. | 4 | 2.7 | Up |
| | | 24 | 5.1 | Up |
| CXCL1 | Chemokine (C—X—C motif) ligand 1 (CXCL1), mRNA. | 24 | 15.5 | Up |
| CXCL2 | Chemokine (C—X—C motif) ligand 2 (CXCL2), mRNA. | 4 | 3.5 | Up |
| | | 24 | 73.5 | Up |
| CXCL5 | Chemokine (C—X—C motif) ligand 5 (CXCL5), mRNA. | 24 | 8.1 | Up |
| | | 96 | 15.1 | Up |
| CXCL7 | Chemokine (C—X—C motif) ligand 7 (CXCL7), mRNA. | 24 | 17.5 | Up |
| | | 96 | 37.4 | Up |
| CXCL13 | Chemokine (C—X—C motif) ligand 13 (CXCL13), mRNA. | 24 | 2.2 | Up |
| | | 96 | 23.5 | Up |
| CCL1 | Chemokine (C-C motif) ligand 1 (CCL1), mRNA. | 24 | 39.8 | Up |
| | | 96 | 42.6 | Up |
| CCL3 | Chemokine (C-C motif) ligand 3 (CCL3), mRNA. | 24 | 56.9 | Up |
| CCL7 | Chemokine (C-C motif) ligand 7 (CCL7), mRNA. | 4 | 9.4 | Up |
| | | 24 | 54.5 | Up |
| | | 96 | 4.8 | Up |
| CCL3L1 | Chemokine (C-C motif) ligand 3-like 1 (CCL3L1), mRNA. | 4 | 5.3 | Up |
| | | 24 | 72.3 | Up |
| | | 96 | 4.2 | Up |
| MMP1 | Matrix metallopeptidase1 (MMP1), mRNA. | 4 | 3.1 | Up |
| | | 24 | 4.2 | Up |
| MMP7 | Matrix metallopeptidase7 (MMP7), mRNA. | 4 | 3.5 | Up |
| | | 24 | 7.4 | Up |
| | | 96 | 117.3 | Up |
| MMP9 | Matrix metallopeptidase 9 (MMP9), mRNA. | 24 | −22.9 | Down |
| MMP10 | Matrix metallopeptidase 10 (stromelysin 2) (MMP10), mRNA. | 4 | 3.2 | Up |
| | | 24 | 52 | Up |
| MMP19 | Matrix metallopeptidase19, transcript var. 1, mRNA. | 4 | 11.6 | Up |
| | | 24 | 2.6 | Up |
| TIMP2 | TIMP metallopeptidase inhibitor 2 (TIMP2), mRNA. | 24 | −10.9 | Down |
| THBS1 | Thrombospondin 1 (THBS1), mRNA. | 4 | −47.8 | Down |
| | | 24 | −101.5 | Down |
| KLF10 | Kruppel-like factor 10 (KLF10), transcript variant 1, mRNA. | 4 | 5.9 | Up |
| | | 24 | 9.3 | Up |
| TGM3 | Transglutaminase3 (TGM3), mRNA. | 4 | 2.3 | Up |
| | | 24 | 28.4 | Up |
| TGM2 | Transglutaminase 2 (TGM2), transcript variant 1, mRNA. | 24 | 12.2 | Up |
| | | 96 | 4.4 | Up |
| TGM5 | Transglutaminase 5 (TGM5), transcript variant 2, mRNA. | 24 | −3.3 | Down |

Wound Healing-Relevant Gene Expression Changes Induced in the Mouse Stroma of Human Tumour Xenografts by Compound 1

Excellent healing of tumour sites in mice and companion animals, evidenced by restoration of hair and hair color as well as minimal scarring, is a notable feature of Compound 1 treatment by intratumoural injection (Examples 16 and 17). Changes in gene expression relevant to wound healing were therefore assayed in the mouse-derived stroma of human tumour xenografts at early times after injection while the tumour was still intact.

Expression data using mouse gene-specific microarrays were performed for 2-3 individual human SK-Mel-28 xenografts treated by intratumoural injection with 30 μg of Compound 1, along with 3 vehicle-only sites, the data combined. Only those mouse genes for which expression in the Compound 1 treated site was >2 times higher or >2 times lower than in the vehicle-injected site were examined for relevance to wound healing.

Table 15 lists genes selected by the above criteria and with known links to wound healing.

A number of genes with known favourable outcomes for wound healing were up-regulated by at least 2-fold by Compound 1. These were genes involved in muscle contraction (ACTA1), growth (EGR1), modulation of inflammation (CXCL1), keratins for renewal of keratinocytes (krt5, 10, 14, 15, 17, 71, krtdap), keratinocyte migration (Col17a1), epidermal differentiation and cell communication (lor, Tgm2, Itga7).

One wound healing related gene, Thrombospondin 2 (Thbs2), was down-regulated. Down-regulation of this gene is associated with increased vascular density and increase in fibronectin in early stages of wound healing.

(IL-1β, IL-6, IL-8 and TNFα) known to be critical in early stages of the wound healing process were investigated in human peripheral blood mononuclear cells (PBMCs).

PBMCs were isolated by Ficoll-Paque sedimentation of heparinised blood acquired from both a 72-year old male (Donor 1) and 34-year old (Donor 2) male human donor. All cells were cultured in 10% FCS, RPMI as detailed previously.

PBMCs were seeded at a density of $1.5 \times 10^5$ cells per well in 10% FCS, RPMI. Stimulation of these cells with the four compounds was performed at four concentrations (0 ng/mL, 3 ng/mL, 30 ng/mL, 300 ng/mL) in duplicate for 24 h in a

TABLE 15

Changes in expression of genes relevant to improved wound healing outcomes that are induced in mouse stroma of human tumour xenografts by Compound 1

| Gene code | Gene name (*Mus musculus*) | Time (h) | Fold change in expression | Direction of regulation |
|---|---|---|---|---|
| Acta1 | actin, alpha 1, skeletal muscle (Acta1), mRNA. | 0.5 | 9.3 | Up |
| | | 4 | 30.3 | Up |
| | | 8 | 8.5 | Up |
| Egr1 | early growth response 1 (Egr1), mRNA. | 4 | 4.7 | Up |
| | | 8 | 5.34 | Up |
| CXCL1 | chemokine (C—X—C motif) ligand 1 (Cxcl1), mRNA. | 4 | 12.1 | Up |
| krt14 | keratin 14 (Krt14), mRNA. | 1 | 9.4 | Up |
| | | 2 | 5.6 | Up |
| | | 4 | 9.7 | Up |
| Krt10 | keratin 10 (Krt10), mRNA. | 1 | 7 | Up |
| | | 2 | 2.4 | Up |
| | | 4 | 8.6 | Up |
| | | 8 | 2.1 | Down |
| Krt17 | keratin 17 (Krt17), mRNA. | 1 | 2.9 | Up |
| | | 4 | 10 | Up |
| | | 8 | 2 | Down |
| Krt15 | keratin 15 (Krt15), mRNA. | 1 | 2.3 | Up |
| Krt5 | keratin 5 (Krt5), mRNA. | 1 | 2.8 | Up |
| Krt71 | keratin 71 (Krt71), mRNA. | 4 | 3.2 | Up |
| Col17a1 | collagen, type XVII, alpha 1 (Col17a1), mRNA. | 1 | 2.7 | Up |
| | | 2 | 2 | Up |
| | | 4 | 3.2 | Up |
| Krtdap | keratinocyte differentiation assoc. (Krtdap), mRNA. | 1 | 7 | Up |
| | | 4 | 3.8 | Up |
| Lce1m | latecornified envelope 1M (Lce1m), mRNA. | 1 | 4.9 | Up |
| Lce1b | latecornified envelope 1B (Lce1b), mRNA. | 1 | 4.8 | Up |
| Lce1d | latecornified envelope ID (Lce1d), mRNA. | 1 | 3.3 | Up |
| LCe1a1 | latecornified envelope 1A1 (Lce1a1), mRNA. | 1 | 2.7 | Up |
| | | 4 | 2.8 | Up |
| Lce1a2 | latecornified envelope 1A2 (Lce1a2), mRNA. | 1 | 3 | Up |
| Lor | loricrin (Lor), mRNA. | 1 | 11.6 | Up |
| | | 2 | 2.8 | Up |
| Tgm2 | transglutaminase 2, C polypeptide (Tgm2), mRNA. | 0.5 | 2.67 | Up |
| | | 4 | 2 | Down |
| Thbs2 | thrombospondin 2 (Thbs2), mRNA. | 0.5 | 3.98 | Down |
| Itga7 | integrin alpha 7 (Itga7), mRNA. | 1 | 2.1 | Up |

Example 12: Effect of Compounds on Cytokine Production

Specific cytokines play critical roles in wound healing processes, and agents that modulate these substances may be useful in treating wounds and/or improving the cosmetic outcomes of healing (e.g. reduced scarring). The effects of Compounds 1, 2, 5 and 42 on regulation of four cytokines humidified incubator at 37° C., 5% $CO_2$. Media samples were taken from each of the required wells and frozen at −80° C. until use.

Cytometric Bead Array (CBA) assays were used to measure the results. CBA assays provide a method for capturing a soluble analyte or set of analytes using antibody coated beads of known sizes and fluorescence. Detection is then performed using another fluorescently labelled secondary antibody to form a sandwich complex. Each media sample was assayed for the presence of soluble IL-1β, IL-6, IL-8, IL-10, IL-12p70 and TNFα using a BD (Becton Dickinson) CBA Human Inflammatory Cytokine Detection Kit according to manufacturers' instructions. Mean fluorescence intensity values from each sample were compared against a standard curve to determine cytokine concentrations (pg/mL).

The results of the CBA assay for each compound are shown in Table 16.

All four compounds significantly increased levels of the four cytokines (TNFα, IL-1β, IL-6, IL-8) that were detected in supernatants assayed from the treated PBMCs, with trends consistent between PBMCs from the two donors. Highest cytokine levels generally occurred at the two highest concentrations (30 and 300 ng/mL) of the compounds.

consistent with the observed direct effects of the compounds on pro-inflammatory cells (Examples 7 and 9) and on gene expression and cytokine profiles in PBMCs (Examples 11 and 12). Such a robust but transient pro-inflammatory response has often been associated with good in vivo wound healing outcomes.

Example 14: Gel Formulation of Compound 1

Either 30 mg or 50 mg of Compound 1 (>97% purity by HPLC) was dissolved in 5 mL of 99.5% isopropyl alcohol (Biotech Pharmaceuticals) and allowed to stand overnight. A solution of 0.6% Carbomer 940 (Snowdrift Farms) was prepared as the gelling agent in 5 mL of sterile water. The Compound 1 concentrate and the 0.6% Carbomer 940 solution were then added together in a 20 mL syringe and

TABLE 16

Production of cytokines from PBMCs after incubation for 24 hr at concentrations of 0, 3, 30 and 300 ng compound/ml for Compounds 1, 2, 5 and 42. Cytokine levels are expressed in pg/ml ± standard deviation and are presented for each of two donors.

| Cytokine | 0 | 3 | 30 | 300 | 0 | 3 | 30 | 300 |
|---|---|---|---|---|---|---|---|---|
| | | | | [Compound 1] ng/mL | | | | |
| TNFα | 3.7 ± 1.1 | 24.3 ± 1.4 | 324.4 ± 0.0 | 355.0 ± 4.3 | 5.3 ± 0.5 | 11.2 ± 0.3 | 209.6 ± 7.5 | 592.2 ± 24.7 |
| IL-1β | 0.8 ± 0.1 | 1.2 ± 0.2 | 11.9 ± 0.8 | 39 ± 0.2 | 1.3 ± 0.9 | 3.1 ± 0.9 | 43.9 ± 1.7 | 121.6 ± 5.6 |
| IL-6 | 4.5 ± 0.8 | 9.7 ± 1.2 | 34.2 ± 1.1 | 89.5 ± 13.8 | 10.5 ± 1.1 | 8.3 ± 0.4 | 12.6 ± 0.9 | 38.8 ± 9.0 |
| IL-8 | 425 ± 41 | 1720 ± 157 | 16920 ± 1198 | 16419 ± 40 | 855 ± 83 | 1493 ± 2 | 24078 ± 815 | 32021 ± 1156 |
| | | | Donor 1 | | | | Donor 2 | |
| | | | | [Compound 2] ng/mL | | | | |
| TNFα | 3.8 ± 0.7 | 31.15 ± 6.9 | 314.07 ± 37.9 | 330.0 ± 28.7 | 26.2 ± 23.9 | 27.3 ± 8.3 | 211.5 ± 12.4 | 618.1 ± 63.7 |
| IL-1β | 0.9 ± 0.1 | 1.4 ± 1.2 | 12.1 ± 0.4 | 37.7 ± 4.6 | 5.5 ± 3.2 | 6.7 ± 1.5 | 52.6 ± 5.0 | 123.9 ± 1.0 |
| IL-6 | 3.8 ± 0.3 | 9.1 ± 0.2 | 38 ± 3.9 | 84.1 ± 3.6 | 13.7 ± 4.9 | 14.9 ± 1.1 | 14.5 ± 3.3 | 41.4 ± 2.3 |
| IL-8 | 430 ± 66 | 2099 ± 585 | 18229 ± 2592 | 16634 ± 625 | 4073 ± 3881 | 2608 ± 309 | 26401 ± 271 | 34117 ± 630 |
| | | | Donor 1 | | | | Donor 2 | |
| | | | | [Compound 5] ng/mL | | | | |
| TNFα | 4.3 ± 0.6 | 85.8 ± 8.4 | 289.9 ± 18.6 | 306.4 ± 9.0 | 15.4 ± 4.2 | 53.9 ± 9.0 | 223 ± 11.2 | 620.9 ± 66.5 |
| IL-1β | 0.6 ± 0.1 | 2.1 ± 0.1 | 15.7 ± 0.9 | 44 ± 1.6 | 4.6 ± 0.1 | 8.1 ± 2.8 | 43.6 ± 6.1 | 114.9 ± 2.4 |
| IL-6 | 3.7 ± 1.0 | 12.4 ± 0.2 | 33.6 ± 0.6 | 77.5 ± 9.1 | 9.5 ± 2.1 | 14.9 ± 1.1 | 12.5 ± 1.2 | 51.9 ± 1.3 |
| IL-8 | 360 ± 22 | 4924 ± 366 | 17190 ± 55 | 17275 ± 40 | 2026 ± 206 | 4765 ± 999 | 26288 ± 260 | 33876 ± 2532 |
| | | | Donor 1 | | | | Donor 2 | |
| | | | | [Compound 42] ng/mL | | | | |
| TNFα | 5.0 ± 1.0 | 45.8 ± 55.2 | 271.9 ± 22.4 | 267.5 ± 11.9 | 12.6 ± 7.7 | 109.5 ± 29.3 | 354.2 ± 6.3 | 631.6 ± 16.9 |
| IL-1β | 2.7 ± 0.4 | 2.6 ± 0.6 | 16.8 ± 1.2 | 41.3 ± 1.2 | 1.9 ± 1.3 | 21.7 ± 7.5 | 71.2 ± 6.0 | 137.8 ± 10.9 |
| IL-6 | 5.1 ± 2.5 | 8.1 ± 6.4 | 32.1 ± 6.7 | 71 ± 4.6 | 10.1 ± 1.7 | 30.4 ± 11.8 | 23.6 ± 0.8 | 69.3 ± 1.8 |
| IL-8 | 403 ± 86 | 3013 ± 377 | 16389 ± 884 | 17425 ± 680 | 1224 ± 887 | 7885 ± 2516 | 28176 ± 37 | 32925 ± 552 |
| | | | Donor 1 | | | | Donor 2 | |

Examples of In Vivo Activity

Example 13: Acute Inflammatory-Response in Mouse Skin

An acute inflammatory response is an important initial phase of the wound healing process. Pro-inflammatory cells, primarily neutrophils and macrophages, migrate to the site and protect it from infection and release cytokines and chemokines involved in the initiation and regulation of subsequent tissue repair.

Male nude mice were injected subcutaneously on each flank with 50 μL of solutions of 100 μg/mL of Compounds 1, 2, 5 and 42 respectively in 20% propylene glycol. Each site reddened within 4 hr and by 24 hr the affected area covered approximately 1 cm diameter of skin. Induration formed over the next 6 days and by 14 days the site had completely healed with minimal scarring.

The acute inflammatory response initiated by the compounds in mouse skin, followed by rapid resolution, is thoroughly mixed. 20 μL of 100% triethanolamine (Sigma-Aldrich) was then added and mixed rapidly. The resulting Compound 1 gel was then dispensed into individual 1 mL insulin syringes to produce doses of 3 mg Compound 1/mL and 5 mg Compound 1/mL.

Example 15: Injectable Formulation of Compound 1

20 mg of Compound 1 (>97% purity by HPLC) was dissolved in 8 mL of 1.2 propanediol (Sigma-Aldrich) in a 20 mL capacity glass scintillation vial and allowed to stand overnight at room temperature. 12 mL of either 30 mM acetate buffer at pH 4.2 or saline (sodium chloride for injection BP 0.9%—AstraZeneca) was then added to the solution and thoroughly mixed. The solution was then filter sterilised and dispensed into 1 mL dose of 1 mg/mL concentration of Compound 1.

Example 16: Veterinary Clinical Treatment of Non-Healing WoundsaAnd Wounds that do not Respond to Current Standards of Care Compound 1 has been used to treat to heal difficult wounds in 10 pet (i.e. privately owned and cared for) animals with the aim of improving second intention wound healing.

Seven dogs (*Canis lupus familiaris*) and one tree kangaroo (*Dendrolagus lumholtzii*) with chronic, non-healing wounds that were unresponsive to current veterinary standards-of-care for these indications were treated with Compound 1 by independent veterinarians. A second tree kangaroo and a spectacled flying fox (*Pteropus conspicillatus*) with wounds unsuited for initial treatment with current standards-of-care were also treated with Compound 1. All cases were managed as open wounds without the use of dressings or other bandaging during the course of treatment with Compound 1 and the subsequent period of wound resolution. Unless stated in individual case studies, no concomitant medications were used over the course of treatments with Compound 1.

Case and treatment notes for each of these patients are summarised below. Note that the return presentation of these animals to the treating veterinarians was often irregular and wound healing outcomes may have occurred well before the return assessment visits.

Treatment with Compound 1 resulted in effective wound resolution with minimal scarring in the eight completed cases. Wound resolution was well progressed in the two on-going case studies that were most recently treated (Case studies 8 and 10).

Case Studies 1 to 8: Non-Healing Wounds
Case Study 1: Non-Healing Deep Necrosing Facial Wound, 3 Year Old Bernese Mountain Dog
Case Notes:
- Large, oval shaped facial wound 7 cm long×4 cm wide× up to 2 cm deep on the left hand side of the patient's nuzzle.
- Wound was crusted with patches of necrotic pustulant discharge.
- Histopathology: deep necrosing injury possibly associated with a spider bite and characterised by the presence of coccoid bacteria and suppurative inflammation.
- Wound had not responded to standard wound treatment protocols involving antibiotics (cephalexin, amoxyclav, gentamicin) and anti-inflammatories (macrolone) over a period of 3 months.
- Wound was gradually increasing in size, causing eye closure and significantly affecting patient's vision and general demeanour. The patient's mandibullar lymph nodes had become enlarged.
- Remaining standard-of-care option was for aggressive facial surgery and reconstruction.
- Initial treatment involved 5 applications (totalling 5.3 mL) of Compound 1 gel (3 mg/mL) over an initial 14 day period (Compound 1 applied on days 1, 2, 6, 10 and 14).
- After partial resolution of the wound at 28 days, the patient was treated with a single 1 mL dose of Compound 1 (0.5 mg/mL) injected just under the surface at multiple locations throughout the wound area.
- At 35 days following injection with Compound 1 the wound had infilled with healthy differentiating granulation tissue and there was no evidence of infection.
- Concomitant medications over the course of the treatment with Compound 1 were temgesic and lignocaine at time of the first treatment with gel formulation, temgesic and tramadol at the time of and on the day immediately after the injection treatment (i.e. days 28 and 29) and then a supportive cover of low dose oral corticosteroid (macrolone) daily from day 42.
- At 76 days following the final treatment the wound had healed and was infilled with normal tissue minimal scarring and also hair regrowth covering greater than 95% of the original wound area.

Case Study 2: Burst, Infected Abdominal Cyst, 13 Year Old Boxer
Case Notes:
- Frail patient with severe osteoarthritis, considered a high anaesthetic risk for any surgical intervention.
- Patient had persistent infected cyst on the back proximal to the tail that had not responded to regular draining and injection of the cyst with antibiotics (gentamycin, enrofloxacin, norocillin) over a 5 month period.
- Patient presented with the burst cyst and elevated temperature. The cyst was cleaned to remove dead skin and then flushed with saline and chlorhexidene. The patient was treated with antibiotics (clindamycin and norocillin) and anti-inflammatories (metacam).
- After 5 days the wound associated with the burst cyst showed no signs of resolving and was surrounded by significant local inflammation. The exposed area of the wound (approximately 5 cm long×3 cm wide by up to 2.5 cm deep) was then flushed with saline and 0.5 mL of Compound 1 gel (3 mg/mL) was applied evenly over the wound area.
- By 5 days post treatment with the Compound 1 gel the wound had significantly contracted to less than 30% of the area of the original wound (approximate dimensions 3 cm long×1.5 cm wide×1 cm deep) and was comprised of healthy granulation tissue.
- At 30 days the wound had resolved with normal tissue and greater than 70% hair regrowth over the original wound area.
- Concomitant medications for this patient over the course of the treatment with Compound 1 were an injectable non-steroidal anti-inflammatory (metacam) at time treatment.

Case Study 3: Non-Healing Infected Puncture Wounds, 11 Year Old Chow Chow
Case Notes:
- The patient presented with two large bite wounds (each approximately 4 cm long×1.5 cm wide×2 cm deep) on the ramp from a dog fight.
- Wounds were washed and the patient treated with antibiotics (amoxyclav tablets and injectable norocillin)
- After 8 days the wounds were persistent, not closing up and infected.
- The wounds were cleaned and 0.4 mL of Compound 1 gel (3 mg/mL) applied evenly to each wound.
- By 15 days post treatment with Compound 1 the wounds had significantly contracted to less than 40% of their original size, formed eschars and there was no evidence of infection.
- At 46 days following treatment with Compound 1 the wounds had completely resolved with normal tissue, no scarring and complete hair regrowth over the wound area.
- No concomitant medications were with this patient over the treatment with Compound 1.

Case Study 4: Non-Healing Infected Wounds on the Face and Metatarsals of a Canine (11 Year Old Boxer)
  Case Notes:
    The patient presented with two areas of non-healing infected and inflamed wounds, one on the left hand side of the face and one on the left hind metatarsals that had not responded to a prolonged 8 week course of antibiotics (cephalexin, doxycycline) and corticosteroids (macrolone).
    A single treatment of a 5 mg/mL gel formulation of Compound 1 was applied to wound on the face (0.4 mL) and to the wound on the leg (0.6 mL).
    The facial wound responded rapidly to treatment with Compound 1 with a small eschar present at 7 days and complete wound closure, including significant hair regrowth evident by 14 days after treatment. The wound area was fully healed by 63 days after treatment.
    The wound on leg also responded quickly with eschar present in localised areas. By 14 days the eschar had largely shed and healthy underlying granulation tissue was observed. The wound area had completely closed and had greater than 95% hair cover at 63 days after treatment.
    Concomitant medications for this patient over the course of the treatment with Compound 1 were an on-going daily course of low dose corticosteroids (macrolone) for treatment of canine atopic dermatitis syndrome.
Case Study 5: Non-Healing Infected Wound on the Ear of a Canine (4 Year Old Bull Arab)
  Case Notes:
    Patient presented with a non-healing laceration due to a hunting accident that had been present on the left ear for more than 6 weeks.
    Three treatments, each of 0.1 mL of 5 mg/mL gel formulation of Compound 1, were applied to the affected area at 8 day intervals. No concomitant medications were used during the course of treatment of the patient with Compound 1.
    By 41 days after the first treatment with Compound 1 the wound had fully closed. A further assessment at 152 days after the initial treatment showed complete wound resolution, minimal scarring with greater than 80% hair coverage over the original wound site.
Case Study 6: Non-Healing Infected Wound on Ear of a Canine (11 Year Old Boxer)
  Case Notes:
    The patient presented with non-healing (infected and inflamed) sore on upper part of left ear and was treated for 10 weeks with standard-of-care protocols involving regular application of (i) a topical dermatological formulation (Neotopic) combining antibacterial (neomycin sulphate), anti-inflammatory (hydrocortisone) and anti-pruritic (lignocaine) agents, and (b) a commercial suspension (Auracol) with anti-inflammatory (prednisolone), antifungal (miconazole nitrate) and antibacterial (polymixin B sulphate) components. Prior to these treatments the patient was on an on-going course of low dose oral corticosteroids (macrolone) for treatment of chronic canine atopic dermatitis syndrome.
    After 10 weeks of the standard-of-care protocol there was no sign of wound resolution.
    A single treatment of 3 mL of a 5 mg/mL gel formulation of Compound 1 was applied to the affected area and within 15 minutes of application of Compound 1 there was discernable reddening of the treated area.
    From 4 days after treatment with Compound 1 the patient recommenced low dose daily corticosteroids (macrolone) for treatment of the severe atopic dermatitis. This treatment continued through the full course of wound healing and resolution.
    At 17 days after treatment with Compound 1 there was no sign of infection or inflammation and a well granulated wound bed had developed at the treated site.
    At 83 days after treatment, there was complete wound closure and hair regrowth had occurred over more than 90% of the original wound area.
    By 139 days after treatment it was not possible to discern the site of the original wound, there was no evidence of scarring and or differences in skin pigmentation or apparent thickness in and surrounding the treated area.
Case Study 7: Non-Healing Infected Wounds on the Ears and Face of a Canine (8 Year Old Jack Russell Terrier)
  Case Notes:
    The patient presented with two non-healing wounds at the tip and base of the right ear and a non-healing wound on the snout that owner had observed present for more than 4 weeks. Possible origin was infected spider or other insect bites.
    Two treatments, each of 0.1 mL of 5 mg/mL gel formulation of Compound 1, were applied to both affected areas on the ears at a 5 day interval. A single treatment of 0.1 mL of 5 mg/mL gel formulation of Compound 1 was applied to the facial lesion.
    By 13 days after the first treatment with Compound 1 both wounds on the ear had contracted significantly and had formed eschars. By 29 days the wound had fully closed and with complete cover of hair growth
    At 16 days after treatment, the wound on the snout had fully resolved.
    Concomitant medication for this patient was a 5 day course of the oral antibiotics amoxicillin, and clavulanic acid (amoxyclav) at the time of the initial treatment.
Case Study 8: Infected Bone Wound on the Leg of a Tree Kangaroo (Marsupialia, *Dendrolagus lumholtzi*)
  Case Notes:
    The patient presented as a wild tree kangaroo injured in a dog attack that resulted in lacrosacral luxation and osteomyelitis. The patient was treated for 1 month with injectable antibiotics ceftazidime (Fortum) and trimethoprim sulphamethoxazole (TMS). While inflammation had been reduced bacterial swab revealed Gram negative bacteria and *Serratia marcesens* were still present. The affected limb was not weight bearing.
    Treatment with ceftazidime for a further 2 weeks resulted in no improvement in condition and veterinarian advised poor prognosis for clearing of infection from the bone and likely significant mechanical disruption to bone structure which would comprise future gait. A new bacterial swab taken from discharging sinuses on the hock and pad at that time revealed mixed anaerobe species and Gram positive *Actinomyces* species so a single slow IV infusion of sodium iodide (Sodide) was delivered.
    Because of the lack of response to other treatments and the overall poor prognosis with these standards of care, rescue treatment involving 4 applications of 5 mg/mL gel formulation of Compound 1 was commenced 2 weeks later.
    For the first application 0.1 mL of the Compound 1 gel was applied to each of three lesions on the right hock (one over the ankle joint, one underneath the foot pad and a small lesion at the base of the heal) and a slow IV infusion of sodium iodide commenced. Within 10 minutes of the application of Compound 1 gel there was a purulent discharge from the treated area.

On presentation 8 days after the first treatment a purulent discharge was oozing from 2 of the 3 wounds on the leg. The other wound (smallest lesion on the heal) had contracted and commenced healing. A further treatment of 0.15 mL of 5 mg/mL gel formulation of Compound 1 was used to treat each of the two open wounds (one over the ankle joint, the other on the base of the foot pad). A slow IV infusion of sodium iodide was also given.

A further 15 days later (23 days after initial treatment) several mLs of thick purulent pus was squeezed from the wound on the pad of the foot before forcing 0.15 mL of 5 mg/mL gel formulation of Compound 1 into the drained wound sinus.

One week later there was significant improvement in the infection. A small piece of bone was removed from the hole in the foot pad. There was no pus evident but there was a serous discharge. A further 0.2 mL of the Compound 1 gel was applied to each of lesions, one over the ankle, the other underneath the foot. A slow IV infusion of sodium iodide was also delivered. Limb is now weight bearing, but the heal and foot pad is still very firm with inflammation and the animal's gait is very uneven and strongly favouring the undamaged hind leg.

A further 15 days later the wound over the ankle joint had fully closed and hair was growing back. The wound on the heal of the foot pad had contracted to less than 50% of its size at the previous visit and the surrounding skin and tissue is soft, pliable and normal. The limb was now fully weight bearing and there is no unevenness in the animal's gait.

Other than the injectable sodium iodide, no other concomitant medications were administered to the patient over the course of treatment with Compound 1.

Case Studies of Difficult Wounds not Suited to Current Standards of Care

Case Study 9: Infectious Vasculitis in the Ear of a Tree Kangaroo (Marsupialia, *Dendrolagus lumholtzi*)

Case Notes:

The patient presented as a young injured animal found in the wild.

Patient was very weak, dehydrated and anaemic. Urine sample revealed blood and bacterial infection, likely septicaemia. Patient was placed on fluid therapy and medicated with anti-nausea drug maropitant citrate (cerenia) and two injectable antibiotic formulations Tribacteral (trimethoprim, sulfadiazine) and ceftazidime (fortum).

After 9 days on a fluid drip the patient's condition had improved but there was trauma to the right ear and likely infectious vasculitis and gangrene. Surgery was not possible because of significant anaesthetic risk due to the patient's highly compromised condition. Instead, treatment with a gel formulation of Compound 1 was initiated.

Three treatments of 0.1 mL of 5 mg/mL strength Compound 1 gel were applied to the affected area at 7 day intervals. The only concurrent medication during this time was the cephalosporin antibiotics ceftazidime (fortum).

At 7 days after the first treatment of Compound 1 gel, a tightly adhering eschar covered the wound surface. This eschar lifted at 10 days to reveal a well-developed, pink granulation bed.

By the time of the third and final treatment application at 14 days after initial treatment the wound area had reduced by approximately 50% and at 25 days healthy tissue was present over the entire area of the wound.

At 67 days the lesion had totally resolved and there was full hair coverage over the ear.

Case Study 10: Severe Lacerated Wound on the Head of a Spectacled Flying Fox (Mammalia, *Pteropus conspicillatus*)

Case notes;

The patient presented as a 4 month old flying fox with a deep penetrating wound on the head of a 4-month old flying fox caused by entanglement in barbed wire.

In the opinion of the treating veterinarian who had extensive experience in wildlife injuries (including flying foxes) normal standard of care treatments were likely to be highly problematic in causing the right eye to lose shape and not be able to close, either due to excessive scar tissue formation associated with surgery or the extent of granulation required if wound healing dressings were applied.

Compound 1 was applied to the wound in 3 applications of 0.1 mL of 5 mg/mL gel formulation over a 28 day period (Days 1, 10 and 28). No other concomitant medications or interventions were used during the course of treatment.

At 14 days after the initial treatment there was significant tissue infill and remodeling and by 28 days the eye was capable of fully closing. By 38 days an eschar covered the entire wound area and this began to slough at 49 days to reveal a good granulation bed.

By 55 days after the initial treatment there was good tissue infill over the entire area of the original wound and the right eye was returning to its original position. A very healthy granulation bed was present.

Example 17: Resolution and Cosmetic Outcome of Wounds Generated Following Necrosis and Sloughing of Spontaneous Tumours in Companion Animals Treated with Compound 1

Veterinary clinical data on speed of resolution of wounds that formed following necrosis and sloughing of spontaneous tumours that had been treated by intratumoural injection of Compound 1 (30% 1.2 propanediol formulation at either 0.5 or 1.0 mg/mL concentration) in twenty-four companion animals are summarised in Table 17.

Note that all wounds were managed as open wounds and no bandaging, dressings, lotions or concomitant medications were used in any of these cases.

TABLE 17

Wound size and speed of resolution (time to closure) in companion animals followed sloughing of spontaneous tumours that had been treated with an injectable formulation of Compound 1.

| Wound size class | Number of cases | Average wound area ($cm^2$) | Average wound depth (mm) | Average days from tumour slough to wound closure |
|---|---|---|---|---|
| Canine | | | | |
| 0.25 to 9 $cm^2$ | 7 | 3.6 ± 2.7 | 6.7 ± 2.8 | 24 ± 16 |
| 9 to 50 $cm^2$ | 5 | 30.4 ± 16.1 | 14.0 ± 5.5 | 40 ± 15 |
| >50 to 130 $cm^2$ | 3 | 95.3 ± 35.0 | 13.3 ± 5.8 | 62 ± 18 |
| Equine | | | | |
| 0.25 to 9 $cm^2$ | 4 | 2.9 ± 1.4 | 7.5 ± 2.9 | 20 ± 12 |
| 9 to 50 $cm^2$ | 2 | 19.5 ± 14.5 | 10.0 ± 0 | 53 ± 22 |
| Feline | | | | |
| 0.25 to 12 $cm^2$ | 3 | 4.8 ± 6.3 | 5.0 ± 4.3 | 17 ± 10 |

The data from these cases also show good cosmetic outcomes for wound resolution with minimal scarring and normal hair regrowth in the majority of patients (Table 18). In the few cases where scarring did occur, these usually coincided with areas of normally thin skin (e.g. on limbs of horses and dogs).

TABLE 18

Tissue, skin and hair features of healed wound sites in companion animals following sloughing of spontaneous tumours that had been treated with an injectable formulation of Compound 1. Tissue, skin and hair features of wound site following resolution

| Wound site feature and outcome category | | No. of dogs | No. of horses | No. of cats |
|---|---|---|---|---|
| Tissue deficit at wound site[1] | Nil or minimal | 15 | 6 | 3 |
| | Minor | 0 | 0 | 0 |
| | Substantial | 0 | 0 | 0 |
| Scarring & skin thickening[2] | Nil or minimal | 13 | 4 | 3 |
| | Minor | 1 | 1 | 0 |
| | Substantial | 1 | 1 | 0 |
| Hair regrowth on wound area[3] | Full | 12 | 5 | 2 |
| | Partial | 1 | 1 | 1 |
| | Sparse | 2 | 0 | 0 |
| Change in hair colour | No | 15 | 3 | 2 |
| | Yes | 0 | 3 | 1 |
| Skin pigmentation | Normal | 11 | 3 | 3 |
| | Patchy | 1 | 1 | 0 |
| | Hypopigmentation | 3 | 1 | 0 |
| | Hyperpigmentation | 0 | 1 | 0 |

[1]Tissue deficit categories Nil or minimal: <5% tissue deficit across the original Wound area Minor: 5 to 10% tissue deficit across the original wound area Substantial: >10% tissue deficit across the original wound area
[2]Scarring and skin thickening categories: Nil or minimal: Scarring not obvious visually or by touch Minor: Localised scar covering <10% of original wound area Substantial: Scarring covering >10% of original wound area
[3]Hair regrowth on wound area categories Full: Hair covers >95% of original wound area Partial: Hair covers >50% of original wound area Sparse: Hair covers <50% of original wound area The claims defining the invention are as follows:

1. A method of promoting wound healing in a subject comprising administering to a wound an epoxy-tigliane compound, wherein the wound is an acute wound, or is a chronic wound that has failed to heal at a normal rate, wherein the compound promotes wound healing by restoring tissue integrity of the wound, and wherein the epoxy-tigliane compound is a compound of formula (II) or a geometric isomer or stereoisomer or a pharmaceutically acceptable salt thereof:

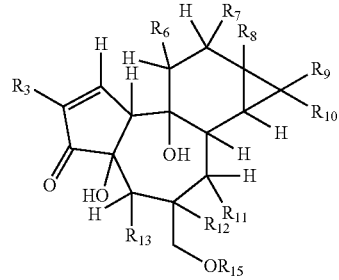

(II)

wherein
$R_3$ is hydrogen or $C_{1-6}$alkyl;
$R_6$ is hydrogen or $C_{1-6}$alkyl;
$R_7$ is —OH or —$OR_{18}$;
$R_8$ is —OH or —$OR_{18}$;
provided that $R_7$ and $R_8$ are not both OH;
$R_9$ and $R_{10}$ are independently selected from hydrogen and $C_{1-6}$alkyl;
$R_{11}$ and $R_{12}$ or $R_{12}$ and $R_{13}$ together form an epoxide and the remaining group of $R_{11}$ and $R_{13}$ is hydrogen, —OH or —$OR_{17}$;
$R_{15}$ is hydrogen or —$R_{17}$;
$R_{17}$ is hydrogen, —$C_{1-6}$alkyl, —$C_{2-6}$alkenyl, —$C_{2-6}$alkynyl, —C(O)$C_{1-6}$alkyl, —C(O)$C_{2-6}$alkenyl or —C(O)$C_{2-6}$alkynyl;
$R_{18}$ is $C_{1-20}$alkyl, —$C_{2-20}$alkenyl, —$C_{2-20}$alkynyl, —C(O)$C_{1-20}$alkyl, —C(O)$C_{2-20}$alkenyl, —C(O)$C_{2-20}$alkynyl, —C(O)cycloalkyl, —C(O)$C_{1-10}$alkylcycloalkyl; —C(O)$C_{2-10}$alkenylcycloalkyl, —C(O)$C_{2-10}$alkynylcycloalkyl, —C(O)aryl, —C(O)$C_{1-10}$alkylaryl, —C(O)$C_{2-10}$alkenylaryl, —C(O)$C_{2-10}$alkynylaryl, —C(O)$C_{1-10}$alkylC(O)$R_{19}$, —C(O)$C_{2-10}$alkenylC(O)$R_{19}$, —C(O)$C_{2-10}$alkynylC(O)$R_{19}$, —C(O)$C_{1-10}$alkylCH($OR_{19}$)($OR_{19}$), —C(O)$C_{2-10}$alkenylCH($OR_{19}$)($OR_{19}$), —C(O)$C_{2-10}$alkynylCH($OR_{19}$)($OR_{19}$), —C(O)$C_{1-10}$alkylS$R_{19}$, —C(O)$C_{2-10}$alkenylS$R_{19}$, —C(O)$C_{2-10}$alkynylS$R_{19}$—C(O)$C_{1-10}$alkylC(O)$OR_{19}$, —C(O)$C_{2-10}$alkenylC(O)$OR_{19}$, —C(O)$C_{2-10}$alkynylC(O)$OR_{19}$, —C(O)$C_{1-}$alkylC(O)$SR_{19}$, —C(O)$C_{2-10}$alkenylC(O)$SR_{19}$, —C(O)$C_{2-10}$alkynylC(O)$SR_{19}$,

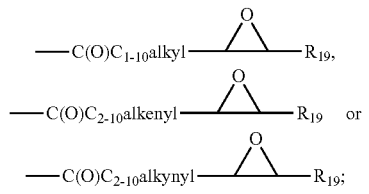

and
$R_{19}$ is hydrogen, —$C_{1-10}$alkyl, —$C_{2-10}$alkenyl, —$C_{2-10}$alkynyl, cycloalkyl or aryl; and
wherein each alkyl, alkenyl, alkynyl, cycloalkyl or aryl group is optionally substituted.

2. The method according to claim 1 wherein the wound is an acute wound.

3. The method according to claim 1 wherein the wound is a chronic wound.

4. The method according to claim 1 wherein the epoxy-tigliane compound is in the form of a plant extract.

5. The method according to claim 4 wherein the plant extract is obtainable from a plant which is a *Fontainea* species or a *Hylandia* species.

6. The method according to claim 1 wherein the compound of formula (II) is a compound of formula (III) or a geometric isomer or stereoisomer or a pharmaceutically acceptable salt thereof:

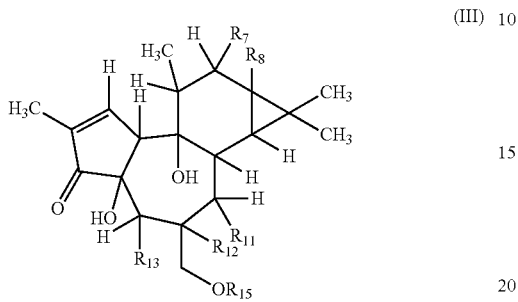

(III)

wherein $R_7$, $R_8$, $R_{11}$, $R_{12}$, $R_{13}$ and $R_{15}$ are as defined for formula (II).

7. The method according to claim 1 wherein $R_3$ is hydrogen or —$C_{1-3}$alkyl.

8. The method according to claim 1 wherein $R_6$ is hydrogen or —$C_{1-3}$alkyl.

9. The method according to claim 1 wherein $R_7$ is —OH, —OC(O)$C_{1-15}$alkyl, —OC(O)$C_{2-15}$alkenyl, —OC(O)$C_{2-15}$alkynyl, —OC(O)aryl wherein the aryl group is optionally substituted, —OC(O)$C_{1-15}$alkylaryl, —OC(O)$C_{1-10}$alkylC(O)H, —OC(O)$C_{2-10}$alkenylC(O)H, —OC(O)$C_{1-10}$alkylC(O)$C_{1-6}$alkyl, —OC(O)$C_{2-10}$alkenylC(O)$C_{1-6}$alkyl, —OC(O)$C_{1-10}$alkylCH(O$C_{1-3}$alkyl)(O$C_{1-3}$alkyl), —OC(O)$C_{2-10}$alkenylCH(O$C_{1-3}$alkyl)(O$C_{1-3}$alkyl), —OC(O)$C_{1-10}$alkylS$C_{1-6}$alkyl, —OC(O)$C_{2-10}$alkenylS$C_{1-6}$alkyl, —OC(O)$C_{1-10}$alkylC(O)O$C_{1-6}$alkyl or —OC(O)$C_{2-10}$alkylC(O)O$C_{1-6}$alkyl.

10. The method according to claim 1 wherein $R_8$ is —OC(O)$C_{1-15}$alkyl, —OC(O)$C_{2-15}$alkenyl, —OC(O)$C_{2-15}$alkynyl or —C(O)aryl where the aryl group is optionally substituted.

11. The method according to claim 1 wherein $R_9$ and $R_{10}$ are independently —$C_{1-3}$alkyl.

12. The method according to claim 1 wherein $R_{11}$ and $R_{12}$ form an epoxide and $R_{13}$ is —OH, —OC(O)$C_{1-6}$alkyl, —OC(O)$C_{2-6}$alkenyl or —OC(O)$C_{2-6}$alkynyl or wherein $R_{12}$ and $R_{13}$ form an epoxide and $R_{11}$ is —OH, —OC(O)$C_{1-6}$alkyl, —OC(O)$C_{2-6}$alkenyl or —OC(O)$C_{2-6}$alkynyl.

13. The method according to claim 1 wherein $R_{15}$ is hydrogen, —C(O)$C_{1-6}$alkyl, —C(O)$C_{2-6}$alkenyl or —C(O)$C_{2-6}$alkynyl.

14. A method of reducing excessive scarring of a healing wound comprising applying to the healing wound an epoxy-tigliane compound, wherein the wound is an acute wound, or is a chronic wound that has failed to heal at a normal rate, wherein the compound promotes wound healing by restoring tissue integrity of the wound, and wherein the epoxy-tigliane compound is a compound of formula (II) or a geometric isomer or stereoisomer or a pharmaceutically acceptable salt thereof:

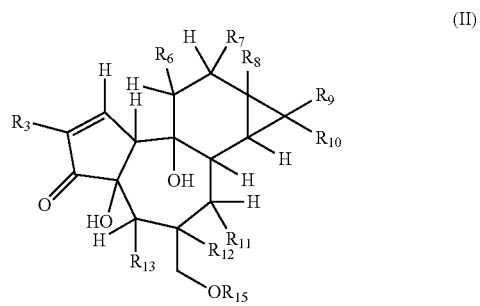

(II)

wherein
$R_3$ is hydrogen or $C_{1-6}$alkyl;
$R_6$ is hydrogen or $C_{1-6}$alkyl;
$R_7$ is —OH or —O$R_{18}$;
$R_8$ is —OH or —O$R_{18}$;
provided that $R_7$ and $R_8$ are not both OH;
$R_9$ and $R_{10}$ are independently selected from hydrogen and $C_{1-6}$alkyl;
$R_{11}$ and $R_{12}$ or $R_{12}$ and $R_{13}$ together form an epoxide and the remaining group of $R_{11}$ and $R_{13}$ is hydrogen, —OH or —O$R_{17}$;
$R_{15}$ is hydrogen or —$R_{17}$;
$R_{17}$ is hydrogen, —$C_{1-6}$alkyl, —$C_{2-6}$alkenyl, —$C_{2-6}$alkynyl, —C(O)$C_{1-6}$alkyl, —C(O)$C_{2-6}$alkenyl or —C(O)$C_{2-6}$alkynyl;
$R_{18}$ is $C_{1-20}$alkyl, —$C_{2-20}$alkenyl, —$C_{2-20}$alkynyl, —C(O)$C_{1-20}$alkyl, —C(O)$C_{2-20}$alkenyl, —C(O)$C_{2-20}$alkynyl, —C(O)cycloalkyl, —C(O)$C_{1-10}$alkylcycloalkyl; —C(O)$C_{2-10}$alkenylcycloalkyl, —C(O)$C_{2-10}$alkynylcycloalkyl; —C(O)aryl, —C(O)$C_{1-10}$alkylaryl, —C(O)$C_{2-10}$alkenylaryl, —C(O)$C_{2-10}$alkynylaryl, —C(O)$C_{1-10}$alkylC(O)$R_{19}$, —C(O)$C_{2-10}$alkenylC(O)$R_{19}$, —C(O)$C_{2-10}$alkynylC(O)$R_{19}$, —C(O)$C_{1-10}$alkylCH(O$R_{19}$)(O$R_{19}$), —C(O)$C_{2-10}$alkenylCH(O$R_{19}$)(O$R_{19}$), —C(O)$C_{2-10}$alkynylCH(O$R_{19}$)(O$R_{19}$), —C(O)$C_{1-10}$alkylS$R_{19}$, —C(O)$C_{2-10}$alkenylS$R_{19}$, —C(O)$C_{2-10}$alkynylS$R_{19}$, —C(O)$C_{1-10}$alkylC(O)O$R_{19}$, —C(O)$C_{2-10}$alkenylC(O)O$R_{19}$, —C(O)$C_{2-10}$alkynylC(O)O$R_{19}$, —C(O)$C_{1-10}$alkylC(O)S$R_{19}$, —C(O)$C_{2-10}$alkenylC(O)S$R_{19}$, —C(O)$C_{2-10}$alkynylC(O)S$R_{19}$,

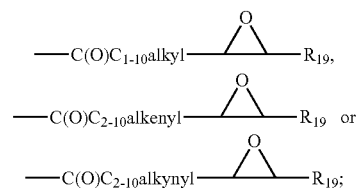

and
$R_{19}$ is hydrogen, —$C_{1-10}$alkyl, —$C_{2-10}$alkenyl, —$C_{2-10}$alkynyl, cycloalkyl or aryl; and
wherein each alkyl, alkenyl, alkynyl, cycloalkyl or aryl group is optionally substituted.

* * * * *